US011578362B2

(12) United States Patent
Smith et al.

(10) Patent No.: US 11,578,362 B2
(45) Date of Patent: Feb. 14, 2023

(54) METHODS OF PRODUCING RIBOSOMAL RIBONUCLEIC ACID COMPLEXES

(71) Applicant: The Regents of the University of California, Oakland, CA (US)

(72) Inventors: Andrew M. Smith, Santa Cruz, CA (US); Miten Jain, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 244 days.

(21) Appl. No.: 16/607,646

(22) PCT Filed: Apr. 26, 2018

(86) PCT No.: PCT/US2018/029613
§ 371 (c)(1),
(2) Date: Oct. 23, 2019

(87) PCT Pub. No.: WO2018/200847
PCT Pub. Date: Nov. 1, 2018

(65) Prior Publication Data

US 2020/0140940 A1 May 7, 2020

Related U.S. Application Data

(60) Provisional application No. 62/490,992, filed on Apr. 27, 2017.

(51) Int. Cl.
*C12Q 1/68* (2018.01)
*C12Q 1/6869* (2018.01)
*C12Q 1/689* (2018.01)

(52) U.S. Cl.
CPC ........... *C12Q 1/6869* (2013.01); *C12Q 1/689* (2013.01); *C12Q 2535/122* (2013.01); *C12Q 2565/631* (2013.01)

(58) Field of Classification Search
CPC .................................................... C12Q 1/6869
See application file for complete search history.

(56) References Cited

U.S. PATENT DOCUMENTS 10,480,026 B2 * 11/2019 Garalde ........... G01N 27/44791
11,021,747 B2 * 6/2021 Garalde .................. C12N 9/14
(Continued)

FOREIGN PATENT DOCUMENTS

WO 2018045109 3/2018

OTHER PUBLICATIONS

Altschul et al. (1997) "Gapped BLAST and PSI-BLAST: a new generation of protein database search programs" Nucleic Acids Res. 25(17):3389-3402.
(Continued)

*Primary Examiner* — Kenneth R Horlick
(74) *Attorney, Agent, or Firm* — Brian E. Davy; Bozicevic, Field & Francis LLP

(57) ABSTRACT

Provided are methods of producing a nucleic acid complex. In certain aspects, the methods include combining a sample including ribosomal RNA (rRNA) and a probe complement oligonucleotide with an oligonucleotide probe. The oligonucleotide probe includes a 3' region complementary to a 3' region of a rRNA, and a 5' region complementary to the probe complement oligonucleotide. The combining is under conditions in which the 3' region of the oligonucleotide probe hybridizes to the 3' region of the rRNA and the 5' region of the oligonucleotide probe hybridizes to the probe complement oligonucleotide, thereby producing a nucleic acid complex. In certain aspects, the methods find use in producing rRNA libraries that find use, e.g., in rRNA sequencing applications. Oligonucleotide probes, libraries
(Continued)

thereof, compositions, and kits that find use, e.g., in practicing the methods of the present disclosure, are also provided.

20 Claims, 23 Drawing Sheets

Specification includes a Sequence Listing.

(56) References Cited

U.S. PATENT DOCUMENTS

| | | | | |
|---|---|---|---|---|
| 2014/0128291 | A1* | 5/2014 | Gu | C12Q 1/6806 506/26 |
| 2017/0253923 | A1* | 9/2017 | Garalde | C12Y 306/04012 |
| 2020/0024654 | A1* | 1/2020 | Heron | C12Q 1/6874 |

OTHER PUBLICATIONS

Burke and Darling (2016) "A method for high precision sequencing of near full-length 16S rRNA genes on an Illumina Mi Seq" PeerJ, 4:e2492, https://doi.org/10.7717/peerj.2492.

Feng et al. (2015) "Nanopore-based Fourth-generation DNA Sequencing Technology" Genomics, Proteomics & Bioinformatics 13(1):4-16.

Karlin and Altschul (1993) "Applications and statistics for multiple high-scoring segments in molecular sequences" Proc. Natl. Acad. Sci. USA 90:5873-5877.

Kerkhof et al (2017) "Profiling bacterial communities by MinION sequencing of ribosomal operons" Microbiome, 5:116.

Kozich et al (2013) "Development of a Dual-Index Sequencing Strategy and Curation Pipeline for Analyzing Amplicon Sequence Data on the MiSeq Illumina Sequencing Platform" Applied and Environmental Microbiology, 79 (17):5112-5120.

Metzker (2010) "Sequencing technologies—the next generation" Nat. Rev. Genet. 11:31-46.

Morey et al. (2013) "A glimpse into past, present, and future DNA sequencing" Mol. Genet. Metab. 110:3-24.

Quast et al. (2013) "The SILVA ribosomal RNA gene database project: improved data processing and web-based tools" Nucleic Acids Res. 41(D1): D590-D596.

Reuter et al. (2015) "High-Throughput Sequencing Technologies" Molecular Cell 58(4):586-597.

Shin et al (2016) "Analysis of the mouse gut microbiome using full-length 16S rRNA amplicon sequencing" Scientific Reports, 6:29681.

Walker et al. (2008) "RNA Affinity Tags for the Rapid Purification and Investigation of RNAs and RNA-Protein Complexes" Methods Mol Biol. 488:23-40.

Wilson and Szostak (1999) "In Vitro Selection of Functional Nucleic Acids" Annu Rev Biochem. 68:611-647.

Yilmaz et al. (2014) "The SILVA and "All-species Living Tree Project (LTP)" taxonomic frameworks" Nucleic Acids Res. 42 (D1): D643-D648.

Caporaso et al. (2012) "Ultra-high-throughput microbial community analysis on the Illumina HiSeq and MiSeq platforms" The ISME Journal, 6:1621-1624.

Caporaso et al. (2012) "Ultra-high-throughput microbial community analysis on the Illumina HiSeq and MiSeq platforms—Supplementary Methods" 6 pages.

Smith et al. (2019) "Reading canonical and modified nucleobases in 16S ribosomal RNA using nanopore native RNA sequencing" PLoS ONE, 14(5):e0216709.

* cited by examiner

B

A

B

C

B

B m7G527 (*E. coli* MRE600 wild type)

| Ref: | 522 | 523 | 524 | 525 | 526 | 527 | 528 | 529 | 530 | 531 |
|------|-----|-----|-----|-----|-----|-----|-----|-----|-----|-----|
|      | C   | A   | G   | C   | C   | G   | C   | G   | G   | U   | A |
|      |     | G   |     |     |     | C   |     |     |     |     |   |
|      |     | U   |     |     |     |     |     | A   |     |     | G |
|      |     | G   |     |     |     |     |     |     |     |     |   |
|      |     | G   |     |     |     |     |     | A   |     | C   |   |
|      |     | G   |     |     |     | C   |     |     |     |     |   |
|      |     |     |     |     |     | C   |     |     |     |     |   |
|      |     |     |     |     |     | C   |     |     |     |     |   |
|      |     | G   |     |     |     | C   |     | A   |     |     |   |
|      |     | G   |     |     |     | C   |     |     |     |     |   |
|      |     | G   |     |     |     | C   |     | A   |     |     | G |
|      |     | G   |     |     |     | C   | A   |     |     |     |   |
|      |     |     |     |     |     |     |     | A   |     |     | G |
|      |     |     |     |     |     | C   |     |     |     |     |   |
|      |     |     |     |     |     |     |     |     |     |     |   |
|      |     |     |     |     |     | C   |     |     |     |     |   |
|      |     | U   |     |     |     | C   |     |     |     |     |   |
|      |     | G   |     |     |     | C   |     | A   |     |     |   |
|      |     |     |     |     |     | C   |     |     |     |     |   |
|      |     |     |     |     |     | C   |     |     |     |     |   |
|      |     | U   |     |     |     | C   |     |     |     |     |   |
|      |     | G   |     |     |     | C   |     |     |     |     |   |
|      |     | G   |     |     |     | C   |     | A   |     |     |   |
|      |     |     |     |     |     | C   |     | A   |     |     |   |
|      |     | U   |     |     |     | C   |     | A   |     |     |   |

B (Cont.)

C

D m7G1405 (*E. coli* BL21 RmtB+)

D (Cont.)

G1405 (*E. coli* BL21 wild type)

A

A

Ψ516 (*E. coli* MRE600 wild type)

| Ref: | 511 | 512 | 513 | 514 | 515 | 516 | 517 | 518 | 519 | 520 |
|---|---|---|---|---|---|---|---|---|---|---|
| | C | T | C | C | G | T | G | C | C | A | G |
| | | | | | | C | | | | |
| | | | | | | C | | | | |
| | | | | | | C | | | | |
| | | | | | | C | | | | |
| | | | | | | C | | | | |
| | | | | | | C | | | | |
| | | A | | | | | | | | |
| | | | | | | C | | | | |
| | | | | | | C | | | | |
| | | | | | | C | | | | |
| | | | | | | C | | | | |
| | | | | | | C | | | | |
| | U | | | | | C | | | | |
| | | A | | | | C | | | | |
| | A | C | | | | C | | | | |
| | | A | | | | C | | | | |
| | | A | | | | C | | | | |
| | | | | | | C | | | | |
| | | | | | | C | | | | |
| | | | | | | C | | | | |
| | | | | | | C | | | | |
| | | | | | | C | | | | |
| | | | | | | C | | | | |
| | | | | | | C | | | | A |
| | | | | | | C | | A | | |

A (Cont.)

u516 (*E. coli JW2171* RsuA mutant)

C

D

SEQUENCE LISTING

```
<160> NUMBER OF SEQ ID NOS: 488

<210> SEQ ID NO 1
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 1

taatgatcct tcc                                                          13


<210> SEQ ID NO 2
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 2

aaggttaagc ctc                                                          13


<210> SEQ ID NO 3
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (1)..(1)
<223> OTHER INFORMATION: N is A,C,G, T, or Z, where Z is the absence of
      a base at that position
<220> FEATURE:
<221> NAME/KEY: Misc_feature
<222> LOCATION: (2)..(2)
<223> OTHER INFORMATION: N is  A, C, G, T or Z, where Z is the absence
      of a base at that position
<220> FEATURE:
<221> NAME/KEY: Misc_feature
<222> LOCATION: (3)..(3)
<223> OTHER INFORMATION: N is A, T or G
<220> FEATURE:
<221> NAME/KEY: Misc_feature
<222> LOCATION: (4)..(4)
<223> OTHER INFORMATION: N is G or T
<220> FEATURE:
<221> NAME/KEY: Misc_feature
<222> LOCATION: (10)..(10)
<223> OTHER INFORMATION: N is G or A
<220> FEATURE:
<221> NAME/KEY: Misc_feature
<222> LOCATION: (11)..(11)
<223> OTHER INFORMATION: N is A or T

<400> SEQUENCE: 3

nnnngaggtn ntc                                                          13
```

-continued

<210> SEQ ID NO 4
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 4
ccatgaggtg ttc 13

<210> SEQ ID NO 5
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 5
taaggaggta ttc 13

<210> SEQ ID NO 6
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 6
aatgaggtgt tc 12

<210> SEQ ID NO 7
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 7
gcatgaggta atc 13

<210> SEQ ID NO 8
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 8
tcaggaggta atc 13

<210> SEQ ID NO 9
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 9
tagggaggta atc 13

<210> SEQ ID NO 10
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 10
cgatgaggtg atc 13

<210> SEQ ID NO 11
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 11
cggtgaggtg ttc 13

<210> SEQ ID NO 12
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 12
gtgggaggtg atc 13

<210> SEQ ID NO 13
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 13
cgtgaggtaa tc 12

<210> SEQ ID NO 14
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 14
agtggaggta ttc 13

<210> SEQ ID NO 15
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 15
ccgggaggtg ttc 13

<210> SEQ ID NO 16
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 16
cggtgaggta ttc 13

<210> SEQ ID NO 17

<211> LENGTH: 13
<212> TYPE: DNA
<213> ORGANISM: Artificial Sequence
<220> FEATURE:
<223> OTHER INFORMATION: Synthetic Sequence

<400> SEQUENCE: 17
tcatgaggta ttc 13

<210> SEQ ID NO 18
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 18
tgtgaggtat tc 12

<210> SEQ ID NO 19
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 19
cgggaggtgt tc 12

<210> SEQ ID NO 20
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 20
ctttgaggta atc 13

<210> SEQ ID NO 21
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 21
caaggaggta ttc 13

<210> SEQ ID NO 22
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 22
gtttgaggta ttc 13

<210> SEQ ID NO 23
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 23
agatgaggtg atc 13

<210> SEQ ID NO 24
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 24
ggtgaggtga tc 12

<210> SEQ ID NO 25
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 25
tttgaggtgt tc 12

<210> SEQ ID NO 26
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 26
agaggaggta atc 13

<210> SEQ ID NO 27
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 27
gtgtgaggtg atc 13

<210> SEQ ID NO 28
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 28
cggtgaggta atc 13

<210> SEQ ID NO 29
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 29
ctgggaggta atc 13

<210> SEQ ID NO 30
<211> LENGTH: 13
<212> TYPE: DNA

-continued

<213> ORGANISM: Artificial Sequence
<220> FEATURE:
<223> OTHER INFORMATION: Synthetic Sequence

<400> SEQUENCE: 30
aggtgaggtg atc 13

<210> SEQ ID NO 31
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 31
gaggaggtat tc 12

<210> SEQ ID NO 32
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 32
aattgaggtg ttc 13

<210> SEQ ID NO 33
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 33
atgtgaggtg atc 13

<210> SEQ ID NO 34
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 34
caggaggtga tc 12

<210> SEQ ID NO 35
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 35
gatgaggtga tc 12

<210> SEQ ID NO 36
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 36
ttgtgaggtg atc 13

<210> SEQ ID NO 37
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 37
cggggaggtg ttc 13

<210> SEQ ID NO 38
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 38
cgggaggtga tc 12

<210> SEQ ID NO 39
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 39
ctttgaggta ttc 13

<210> SEQ ID NO 40
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 40
ttatgaggtg atc 13

<210> SEQ ID NO 41
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 41
ggtggaggta ttc 13

<210> SEQ ID NO 42
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 42
ggatgaggtg ttc 13

<210> SEQ ID NO 43
<211> LENGTH: 13
<212> TYPE: DNA
<213> ORGANISM: Artificial Sequence
<220> FEATURE:

<223> OTHER INFORMATION: Synthetic Sequence

<400> SEQUENCE: 43
tcgtgaggtg ttc 13

<210> SEQ ID NO 44
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 44
agggaggtga tc 12

<210> SEQ ID NO 45
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 45
tatggaggta ttc 13

<210> SEQ ID NO 46
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 46
gttggaggtg ttc 13

<210> SEQ ID NO 47
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 47
gatggaggtg atc 13

<210> SEQ ID NO 48
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 48
gggggaggtg atc 13

<210> SEQ ID NO 49
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 49
acgggaggtg atc 13

<210> SEQ ID NO 50
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 50
gggtgaggta atc 13

<210> SEQ ID NO 51
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 51
aagggaggtg atc 13

<210> SEQ ID NO 52
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 52
gttggaggta atc 13

<210> SEQ ID NO 53
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 53
acgtgaggta ttc 13

<210> SEQ ID NO 54
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 54
ggtgaggtgt tc 12

<210> SEQ ID NO 55
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 55
caggaggtat tc 12

<210> SEQ ID NO 56
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 56
aagtgaggtg ttc 13

<210> SEQ ID NO 57
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 57
ggaggaggtg atc 13

<210> SEQ ID NO 58
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 58
aaggaggtaa tc 12

<210> SEQ ID NO 59
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 59
gattgaggta ttc 13

<210> SEQ ID NO 60
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 60
agaggaggtg atc 13

<210> SEQ ID NO 61
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 61
tagtgaggtg atc 13

<210> SEQ ID NO 62
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 62
gtgggaggtg ttc 13

<210> SEQ ID NO 63
<211> LENGTH: 13

<212> TYPE: DNA
<213> ORGANISM: Artificial Sequence
<220> FEATURE:
<223> OTHER INFORMATION: Synthetic Sequence

<400> SEQUENCE: 63
atgggaggta ttc 13

<210> SEQ ID NO 64
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 64
cagtgaggta ttc 13

<210> SEQ ID NO 65
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 65
tagggaggtg ttc 13

<210> SEQ ID NO 66
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 66
tttggaggtg ttc 13

<210> SEQ ID NO 67
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 67
ttgggaggta ttc 13

<210> SEQ ID NO 68
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 68
gtgggaggta ttc 13

<210> SEQ ID NO 69
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 69
aatgaggtaa tc 12

<210> SEQ ID NO 70
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 70
aaaggaggtg atc 13

<210> SEQ ID NO 71
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 71
acgggaggta ttc 13

<210> SEQ ID NO 72
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 72
ctaggaggta atc 13

<210> SEQ ID NO 73
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 73
gggtgaggta ttc 13

<210> SEQ ID NO 74
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 74
cgtgaggtat tc 12

<210> SEQ ID NO 75
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 75
atggaggtaa tc 12

<210> SEQ ID NO 76
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 76
cgtggaggta ttc 13

<210> SEQ ID NO 77
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 77
aaatgaggta ttc 13

<210> SEQ ID NO 78
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 78
cctggaggtg ttc 13

<210> SEQ ID NO 79
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 79
taggaggtaa tc 12

<210> SEQ ID NO 80
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 80
gttgaggtga tc 12

<210> SEQ ID NO 81
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 81
cgtggaggtg ttc 13

<210> SEQ ID NO 82
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 82
cttggaggta atc 13

-continued

<210> SEQ ID NO 83
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 83
atttgaggtg ttc 13

<210> SEQ ID NO 84
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 84
aatggaggtg ttc 13

<210> SEQ ID NO 85
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 85
tctggaggtg ttc 13

<210> SEQ ID NO 86
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 86
gtaggaggtg ttc 13

<210> SEQ ID NO 87
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 87
acgggaggtg ttc 13

<210> SEQ ID NO 88
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 88
tatggaggta atc 13

<210> SEQ ID NO 89
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 89
agggaggtgt tc 12

<210> SEQ ID NO 90
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 90
cgaggaggta atc 13

<210> SEQ ID NO 91
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 91
tgttgaggtg atc 13

<210> SEQ ID NO 92
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 92
ctatgaggtg atc 13

<210> SEQ ID NO 93
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 93
tattgaggta ttc 13

<210> SEQ ID NO 94
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 94
ctggaggtat tc 12

<210> SEQ ID NO 95
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 95
cttgaggtga tc 12

<210> SEQ ID NO 96

<211> LENGTH: 13
<212> TYPE: DNA
<213> ORGANISM: Artificial Sequence
<220> FEATURE:
<223> OTHER INFORMATION: Synthetic Sequence

<400> SEQUENCE: 96
tgtggaggtg ttc 13

<210> SEQ ID NO 97
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 97
tttggaggta atc 13

<210> SEQ ID NO 98
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 98
cgtggaggtg atc 13

<210> SEQ ID NO 99
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 99
tattgaggtg ttc 13

<210> SEQ ID NO 100
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 100
aattgaggta atc 13

<210> SEQ ID NO 101
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 101
ggttgaggtg ttc 13

<210> SEQ ID NO 102
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 102

-continued ttaggaggtg ttc 13

<210> SEQ ID NO 103
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 103
catggaggtg atc 13

<210> SEQ ID NO 104
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 104
tttggaggta ttc 13

<210> SEQ ID NO 105
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 105
ctggaggtaa tc 12

<210> SEQ ID NO 106
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 106
catggaggtg ttc 13

<210> SEQ ID NO 107
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 107
gaggaggtga tc 12

<210> SEQ ID NO 108
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 108
atatgaggta atc 13

<210> SEQ ID NO 109
<211> LENGTH: 12
<212> TYPE: DNA

<213> ORGANISM: Artificial Sequence
<220> FEATURE:
<223> OTHER INFORMATION: Synthetic Sequence

<400> SEQUENCE: 109
gtggaggtat tc 12

<210> SEQ ID NO 110
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 110
cattgaggtg ttc 13

<210> SEQ ID NO 111
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 111
agggaggtaa tc 12

<210> SEQ ID NO 112
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 112
atttgaggta ttc 13

<210> SEQ ID NO 113
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 113
aggggaggta atc 13

<210> SEQ ID NO 114
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 114
tctggaggtg atc 13

<210> SEQ ID NO 115
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 115
tggggaggtg ttc 13

<210> SEQ ID NO 116
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 116
cgaggaggtg ttc 13

<210> SEQ ID NO 117
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 117
ttggaggtat tc 12

<210> SEQ ID NO 118
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 118
ggatgaggta ttc 13

<210> SEQ ID NO 119
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 119
ctatgaggta ttc 13

<210> SEQ ID NO 120
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 120
ttttgaggta atc 13

<210> SEQ ID NO 121
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 121
tttgaggtga tc 12

<210> SEQ ID NO 122
<211> LENGTH: 13
<212> TYPE: DNA
<213> ORGANISM: Artificial Sequence
<220> FEATURE:

<223> OTHER INFORMATION: Synthetic Sequence

<400> SEQUENCE: 122
acatgaggta ttc 13

<210> SEQ ID NO 123
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 123
gtggaggtaa tc 12

<210> SEQ ID NO 124
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 124
tcaggaggtg ttc 13

<210> SEQ ID NO 125
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 125
tgggaggtaa tc 12

<210> SEQ ID NO 126
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 126
tgttgaggta ttc 13

<210> SEQ ID NO 127
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 127
tgtggaggta ttc 13

<210> SEQ ID NO 128
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 128
ggttgaggta atc 13

<210> SEQ ID NO 129
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 129
ataggaggta atc 13

<210> SEQ ID NO 130
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 130
catggaggta ttc 13

<210> SEQ ID NO 131
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 131
caatgaggtg ttc 13

<210> SEQ ID NO 132
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 132
gttggaggta ttc 13

<210> SEQ ID NO 133
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 133
ggggaggtgt tc 12

<210> SEQ ID NO 134
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 134
gtatgaggtg atc 13

<210> SEQ ID NO 135
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 135
cgttgaggta ttc 13

<210> SEQ ID NO 136
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 136
tagtgaggta atc 13

<210> SEQ ID NO 137
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 137
cagggaggta atc 13

<210> SEQ ID NO 138
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 138
gtgtgaggtg ttc 13

<210> SEQ ID NO 139
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 139
atgggaggtg ttc 13

<210> SEQ ID NO 140
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 140
ctaggaggtg atc 13

<210> SEQ ID NO 141
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 141
agtgaggtaa tc 12

<210> SEQ ID NO 142
<211> LENGTH: 13

<212> TYPE: DNA
<213> ORGANISM: Artificial Sequence
<220> FEATURE:
<223> OTHER INFORMATION: Synthetic Sequence

<400> SEQUENCE: 142
gtaggaggta ttc 13

<210> SEQ ID NO 143
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 143
acaggaggta ttc 13

<210> SEQ ID NO 144
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 144
tattgaggtg atc 13

<210> SEQ ID NO 145
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 145
agttgaggtg ttc 13

<210> SEQ ID NO 146
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 146
gcaggaggtg ttc 13

<210> SEQ ID NO 147
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 147
ttgggaggta atc 13

<210> SEQ ID NO 148
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 148
tggggaggta atc 13

<210> SEQ ID NO 149
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 149
ggtggaggtg ttc 13

<210> SEQ ID NO 150
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 150
tgaggaggtg atc 13

<210> SEQ ID NO 151
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 151
ccgggaggta atc 13

<210> SEQ ID NO 152
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 152
taatgaggtg ttc 13

<210> SEQ ID NO 153
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 153
taatgaggtg atc 13

<210> SEQ ID NO 154
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 154
gctggaggtg atc 13

<210> SEQ ID NO 155
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 155
tcaggaggta ttc 13

<210> SEQ ID NO 156
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 156
cgatgaggta atc 13

<210> SEQ ID NO 157
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 157
ctgggaggta ttc 13

<210> SEQ ID NO 158
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 158
ctatgaggta atc 13

<210> SEQ ID NO 159
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 159
ccttgaggta ttc 13

<210> SEQ ID NO 160
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 160
gcgggaggta ttc 13

<210> SEQ ID NO 161
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 161
acgggaggta atc 13

<210> SEQ ID NO 162
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 162
acaggaggta atc 13

<210> SEQ ID NO 163
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 163
gcttgaggta ttc 13

<210> SEQ ID NO 164
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 164
aaatgaggtg ttc 13

<210> SEQ ID NO 165
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 165
cgatgaggta ttc 13

<210> SEQ ID NO 166
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 166
aagggaggtg ttc 13

<210> SEQ ID NO 167
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 167
gattgaggta atc 13

<210> SEQ ID NO 168
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 168
atatgaggta ttc 13

<210> SEQ ID NO 169
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 169
gatggaggtg ttc 13

<210> SEQ ID NO 170
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 170
gatgaggtgt tc 12

<210> SEQ ID NO 171
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 171
cggggaggta atc 13

<210> SEQ ID NO 172
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 172
taatgaggta atc 13

<210> SEQ ID NO 173
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 173
agtggaggtg atc 13

<210> SEQ ID NO 174
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 174
gagggaggtg atc 13

<210> SEQ ID NO 175

<211> LENGTH: 13
<212> TYPE: DNA
<213> ORGANISM: Artificial Sequence
<220> FEATURE:
<223> OTHER INFORMATION: Synthetic Sequence

<400> SEQUENCE: 175
atatgaggtg atc 13

<210> SEQ ID NO 176
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 176
actggaggtg ttc 13

<210> SEQ ID NO 177
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 177
actggaggtg atc 13

<210> SEQ ID NO 178
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 178
acttgaggtg ttc 13

<210> SEQ ID NO 179
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 179
ccgggaggta ttc 13

<210> SEQ ID NO 180
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 180
attgaggtat tc 12

<210> SEQ ID NO 181
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 181

-continued gaaggaggta atc 13

<210> SEQ ID NO 182
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 182
agatgaggta atc 13

<210> SEQ ID NO 183
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 183
tcgtgaggta ttc 13

<210> SEQ ID NO 184
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 184
agtgaggtga tc 12

<210> SEQ ID NO 185
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 185
tcttgaggtg ttc 13

<210> SEQ ID NO 186
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 186
ttaggaggta ttc 13

<210> SEQ ID NO 187
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 187
ttgtgaggta atc 13

<210> SEQ ID NO 188
<211> LENGTH: 13
<212> TYPE: DNA

<213> ORGANISM: Artificial Sequence
<220> FEATURE:
<223> OTHER INFORMATION: Synthetic Sequence

<400> SEQUENCE: 188
acgtgaggtg atc 13

<210> SEQ ID NO 189
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 189
tttgaggtaa tc 12

<210> SEQ ID NO 190
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 190
ttggaggtgt tc 12

<210> SEQ ID NO 191
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 191
cgttgaggta atc 13

<210> SEQ ID NO 192
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 192
aattgaggta ttc 13

<210> SEQ ID NO 193
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 193
tttggaggtg atc 13

<210> SEQ ID NO 194
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 194
tgatgaggta ttc 13

<210> SEQ ID NO 195
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 195
agatgaggtg ttc 13

<210> SEQ ID NO 196
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 196
ctgtgaggtg atc 13

<210> SEQ ID NO 197
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 197
caatgaggta ttc 13

<210> SEQ ID NO 198
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 198
ggttgaggta ttc 13

<210> SEQ ID NO 199
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 199
cttggaggtg atc 13

<210> SEQ ID NO 200
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 200
gagtgaggtg atc 13

<210> SEQ ID NO 201
<211> LENGTH: 13
<212> TYPE: DNA
<213> ORGANISM: Artificial Sequence
<220> FEATURE:

<223> OTHER INFORMATION: Synthetic Sequence

<400> SEQUENCE: 201
cctggaggta ttc 13

<210> SEQ ID NO 202
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 202
tgggaggtga tc 12

<210> SEQ ID NO 203
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 203
gggggaggta atc 13

<210> SEQ ID NO 204
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 204
cggggaggta ttc 13

<210> SEQ ID NO 205
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 205
attggaggtg ttc 13

<210> SEQ ID NO 206
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 206
tatggaggtg ttc 13

<210> SEQ ID NO 207
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 207
agtggaggta atc 13

<210> SEQ ID NO 208
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 208
gttgaggtat tc 12

<210> SEQ ID NO 209
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 209
ggggaggtga tc 12

<210> SEQ ID NO 210
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 210
actggaggta ttc 13

<210> SEQ ID NO 211
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 211
acttgaggta ttc 13

<210> SEQ ID NO 212
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 212
gaaggaggtg ttc 13

<210> SEQ ID NO 213
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 213
tcttgaggta atc 13

<210> SEQ ID NO 214
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 214
cttgaggtat tc 12

<210> SEQ ID NO 215
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 215
tcttgaggta ttc 13

<210> SEQ ID NO 216
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 216
gcatgaggta ttc 13

<210> SEQ ID NO 217
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 217
gaatgaggta atc 13

<210> SEQ ID NO 218
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 218
catgaggtat tc 12

<210> SEQ ID NO 219
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 219
ccatgaggta ttc 13

<210> SEQ ID NO 220
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 220
tgtgaggtga tc 12

<210> SEQ ID NO 221
<211> LENGTH: 12

-continued

<212> TYPE: DNA
<213> ORGANISM: Artificial Sequence
<220> FEATURE:
<223> OTHER INFORMATION: Synthetic Sequence

<400> SEQUENCE: 221
agggaggtat tc 12

<210> SEQ ID NO 222
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 222
gatggaggta ttc 13

<210> SEQ ID NO 223
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 223
aaaggaggta ttc 13

<210> SEQ ID NO 224
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 224
ggggaggtat tc 12

<210> SEQ ID NO 225
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 225
aatggaggta atc 13

<210> SEQ ID NO 226
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 226
tcgggaggta atc 13

<210> SEQ ID NO 227
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 227
gattgaggtg atc 13

<210> SEQ ID NO 228
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 228
ataggaggtg ttc 13

<210> SEQ ID NO 229
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 229
cctggaggta atc 13

<210> SEQ ID NO 230
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 230
cgtgaggtgt tc 12

<210> SEQ ID NO 231
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 231
ggatgaggtg atc 13

<210> SEQ ID NO 232
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 232
gagggaggta atc 13

<210> SEQ ID NO 233
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 233
agtggaggtg ttc 13

<210> SEQ ID NO 234
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 234
agtgaggtgt tc 12

<210> SEQ ID NO 235
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 235
gggggaggta ttc 13

<210> SEQ ID NO 236
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 236
tgtggaggtg atc 13

<210> SEQ ID NO 237
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 237
cttgaggtgt tc 12

<210> SEQ ID NO 238
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 238
ataggaggta ttc 13

<210> SEQ ID NO 239
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 239
tatgaggtaa tc 12

<210> SEQ ID NO 240
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 240
caatgaggta atc 13

<210> SEQ ID NO 241
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 241
gtatgaggta atc 13

<210> SEQ ID NO 242
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 242
cgtggaggta atc 13

<210> SEQ ID NO 243
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 243
ctgggaggtg ttc 13

<210> SEQ ID NO 244
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 244
aaggaggtgt tc 12

<210> SEQ ID NO 245
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 245
cagggaggta ttc 13

<210> SEQ ID NO 246
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 246
aaaggaggtg ttc 13

<210> SEQ ID NO 247
<211> LENGTH: 13
<212> TYPE: DNA
<213> ORGANISM: Artificial Sequence
<220> FEATURE:
<223> OTHER INFORMATION: Synthetic Sequence -continued

<400> SEQUENCE: 247
ctgtgaggta atc 13

<210> SEQ ID NO 248
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 248
ctaggaggtg ttc 13

<210> SEQ ID NO 249
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 249
aggggaggta ttc 13

<210> SEQ ID NO 250
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 250
ggttgaggtg atc 13

<210> SEQ ID NO 251
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 251
gatggaggta atc 13

<210> SEQ ID NO 252
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 252
tgggaggtat tc 12

<210> SEQ ID NO 253
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 253
tcaggaggtg atc 13

<210> SEQ ID NO 254

<211> LENGTH: 12
<212> TYPE: DNA
<213> ORGANISM: Artificial Sequence
<220> FEATURE:
<223> OTHER INFORMATION: Synthetic Sequence

<400> SEQUENCE: 254
taggaggtga tc 12

<210> SEQ ID NO 255
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 255
gttgaggtaa tc 12

<210> SEQ ID NO 256
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 256
atggaggtgt tc 12

<210> SEQ ID NO 257
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 257
caggaggtaa tc 12

<210> SEQ ID NO 258
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 258
aggggaggtg atc 13

<210> SEQ ID NO 259
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 259
ggaggaggta ttc 13

<210> SEQ ID NO 260
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 260
caggaggtgt tc 12

<210> SEQ ID NO 261
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 261
ccttgaggta atc 13

<210> SEQ ID NO 262
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 262
acgtgaggta atc 13

<210> SEQ ID NO 263
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 263
tctggaggta atc 13

<210> SEQ ID NO 264
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 264
tatgaggtgt tc 12

<210> SEQ ID NO 265
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 265
tattgaggta atc 13

<210> SEQ ID NO 266
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 266
gtaggaggtg atc 13

<210> SEQ ID NO 267
<211> LENGTH: 13
<212> TYPE: DNA

<213> ORGANISM: Artificial Sequence
<220> FEATURE:
<223> OTHER INFORMATION: Synthetic Sequence

<400> SEQUENCE: 267
gctggaggta atc 13

<210> SEQ ID NO 268
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 268
ttaggaggta atc 13

<210> SEQ ID NO 269
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 269
ttatgaggtg ttc 13

<210> SEQ ID NO 270
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 270
gcttgaggtg atc 13

<210> SEQ ID NO 271
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 271
tgaggaggta ttc 13

<210> SEQ ID NO 272
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 272
ttggaggtaa tc 12

<210> SEQ ID NO 273
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 273
tctggaggta ttc 13

<210> SEQ ID NO 274
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 274
cattgaggta ttc 13

<210> SEQ ID NO 275
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 275
acatgaggtg atc 13

<210> SEQ ID NO 276
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 276
caaggaggtg atc 13

<210> SEQ ID NO 277
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 277
ttgtgaggtg ttc 13

<210> SEQ ID NO 278
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 278
tgttgaggta atc 13

<210> SEQ ID NO 279
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 279
gctggaggtg ttc 13

<210> SEQ ID NO 280
<211> LENGTH: 13
<212> TYPE: DNA
<213> ORGANISM: Artificial Sequence
<220> FEATURE:

<223> OTHER INFORMATION: Synthetic Sequence

<400> SEQUENCE: 280
taaggaggtg ttc 13

<210> SEQ ID NO 281
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 281
tcatgaggta atc 13

<210> SEQ ID NO 282
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 282
atgggaggta atc 13

<210> SEQ ID NO 283
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 283
aggtgaggtg ttc 13

<210> SEQ ID NO 284
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 284
tgatgaggtg ttc 13

<210> SEQ ID NO 285
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 285
ctatgaggtg ttc 13

<210> SEQ ID NO 286
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 286
aggtgaggta atc 13

-continued

<210> SEQ ID NO 287
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 287
aagtgaggta ttc 13

<210> SEQ ID NO 288
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 288
ggtggaggta atc 13

<210> SEQ ID NO 289
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 289
gcgtgaggta atc 13

<210> SEQ ID NO 290
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 290
tggtgaggta ttc 13

<210> SEQ ID NO 291
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 291
gcaggaggtg atc 13

<210> SEQ ID NO 292
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 292
ccgtgaggtg ttc 13

<210> SEQ ID NO 293
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 293
catgaggtga tc 12

<210> SEQ ID NO 294
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 294
atggaggtat tc 12

<210> SEQ ID NO 295
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 295
gtttgaggtg atc 13

<210> SEQ ID NO 296
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 296
aaatgaggta atc 13

<210> SEQ ID NO 297
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 297
acttgaggta atc 13

<210> SEQ ID NO 298
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 298
gaggaggtgt tc 12

<210> SEQ ID NO 299
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 299
aaggaggtga tc 12

<210> SEQ ID NO 300
<211> LENGTH: 12

<212> TYPE: DNA
<213> ORGANISM: Artificial Sequence
<220> FEATURE:
<223> OTHER INFORMATION: Synthetic Sequence

<400> SEQUENCE: 300
gtggaggtga tc 12

<210> SEQ ID NO 301
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 301
gcatgaggtg ttc 13

<210> SEQ ID NO 302
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 302
attggaggtg atc 13

<210> SEQ ID NO 303
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 303
tagggaggta ttc 13

<210> SEQ ID NO 304
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 304
atttgaggta atc 13

<210> SEQ ID NO 305
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 305
aatgaggtga tc 12

<210> SEQ ID NO 306
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 306
gatgaggtaa tc 12

<210> SEQ ID NO 307
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 307
gtatgaggta ttc 13

<210> SEQ ID NO 308
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 308
cgttgaggtg ttc 13

<210> SEQ ID NO 309
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 309
ccaggaggta atc 13

<210> SEQ ID NO 310
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 310
ctgggaggtg atc 13

<210> SEQ ID NO 311
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 311
gtgtgaggta ttc 13

<210> SEQ ID NO 312
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 312
aaggaggtat tc 12

<210> SEQ ID NO 313
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 313
aagggaggta ttc 13

<210> SEQ ID NO 314
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 314
gggggaggtg ttc 13

<210> SEQ ID NO 315
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 315
cagtgaggta atc 13

<210> SEQ ID NO 316
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 316
cgatgaggtg ttc 13

<210> SEQ ID NO 317
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 317
taaggaggta atc 13

<210> SEQ ID NO 318
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 318
tggggaggtg atc 13

<210> SEQ ID NO 319
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 319
acttgaggtg atc 13

<210> SEQ ID NO 320
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 320
tagggaggtg atc 13

<210> SEQ ID NO 321
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 321
acatgaggta atc 13

<210> SEQ ID NO 322
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 322
tcgggaggta ttc 13

<210> SEQ ID NO 323
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 323
aagggaggta atc 13

<210> SEQ ID NO 324
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 324
aatggaggta ttc 13

<210> SEQ ID NO 325
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 325
cggtgaggtg atc 13

<210> SEQ ID NO 326
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 326
gcttgaggtg ttc 13

<210> SEQ ID NO 327
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 327
cagtgaggtg ttc 13

<210> SEQ ID NO 328
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 328
gtatgaggtg ttc 13

<210> SEQ ID NO 329
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 329
cttgaggtaa tc 12

<210> SEQ ID NO 330
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 330
tggggaggta ttc 13

<210> SEQ ID NO 331
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 331
gatgaggtat tc 12

<210> SEQ ID NO 332
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 332
cggggaggtg atc 13

<210> SEQ ID NO 333

<211> LENGTH: 13
<212> TYPE: DNA
<213> ORGANISM: Artificial Sequence
<220> FEATURE:
<223> OTHER INFORMATION: Synthetic Sequence

<400> SEQUENCE: 333
gaatgaggta ttc 13

<210> SEQ ID NO 334
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 334
catgaggtaa tc 12

<210> SEQ ID NO 335
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 335
ggtgaggtaa tc 12

<210> SEQ ID NO 336
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 336
tgaggaggta atc 13

<210> SEQ ID NO 337
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 337
gcttgaggta atc 13

<210> SEQ ID NO 338
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 338
ctgtgaggtg ttc 13

<210> SEQ ID NO 339
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 339
tcatgaggtg atc 13

<210> SEQ ID NO 340
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 340
cgggaggtat tc 12

<210> SEQ ID NO 341
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 341
cgttgaggtg atc 13

<210> SEQ ID NO 342
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 342
agtgaggtat tc 12

<210> SEQ ID NO 343
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 343
cgggaggtaa tc 12

<210> SEQ ID NO 344
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 344
tcatgaggtg ttc 13

<210> SEQ ID NO 345
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 345
caaggaggtg ttc 13

<210> SEQ ID NO 346
<211> LENGTH: 13
<212> TYPE: DNA

<213> ORGANISM: Artificial Sequence
<220> FEATURE:
<223> OTHER INFORMATION: Synthetic Sequence

<400> SEQUENCE: 346
ccatgaggta atc 13

<210> SEQ ID NO 347
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 347
tcgtgaggtg atc 13

<210> SEQ ID NO 348
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 348
gcatgaggtg atc 13

<210> SEQ ID NO 349
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 349
aaatgaggtg atc 13

<210> SEQ ID NO 350
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 350
cagtgaggtg atc 13

<210> SEQ ID NO 351
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 351
agaggaggtg ttc 13

<210> SEQ ID NO 352
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 352
caatgaggtg atc 13

<210> SEQ ID NO 353
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 353
tagtgaggta ttc 13

<210> SEQ ID NO 354
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 354
cttggaggta ttc 13

<210> SEQ ID NO 355
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 355
ccgtgaggta ttc 13

<210> SEQ ID NO 356
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 356
tatgaggtat tc 12

<210> SEQ ID NO 357
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 357
gagggaggta ttc 13

<210> SEQ ID NO 358
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 358
ggaggaggta atc 13

<210> SEQ ID NO 359
<211> LENGTH: 12
<212> TYPE: DNA
<213> ORGANISM: Artificial Sequence
<220> FEATURE:

-continued

<223> OTHER INFORMATION: Synthetic Sequence

<400> SEQUENCE: 359
ctggaggtgt tc 12

<210> SEQ ID NO 360
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 360
actggaggta atc 13

<210> SEQ ID NO 361
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 361
gaaggaggtg atc 13

<210> SEQ ID NO 362
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 362
gggtgaggtg atc 13

<210> SEQ ID NO 363
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 363
ttatgaggta ttc 13

<210> SEQ ID NO 364
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 364
acaggaggtg atc 13

<210> SEQ ID NO 365
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 365
tatggaggtg atc 13

-continued

<210> SEQ ID NO 366
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 366
attggaggta ttc 13

<210> SEQ ID NO 367
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 367
gtggaggtgt tc 12

<210> SEQ ID NO 368
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 368
atgtgaggta ttc 13

<210> SEQ ID NO 369
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 369
ttaggaggtg atc 13

<210> SEQ ID NO 370
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 370
attgaggtgt tc 12

<210> SEQ ID NO 371
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 371
ggtgaggtat tc 12

<210> SEQ ID NO 372
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 372
gcgtgaggta ttc 13

<210> SEQ ID NO 373
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 373
gaaggaggta ttc 13

<210> SEQ ID NO 374
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 374
acatgaggtg ttc 13

<210> SEQ ID NO 375
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 375
gcgtgaggtg atc 13

<210> SEQ ID NO 376
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 376
gaggaggtaa tc 12

<210> SEQ ID NO 377
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 377
tgtgaggtgt tc 12

<210> SEQ ID NO 378
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 378
gtaggaggta atc 13

<210> SEQ ID NO 379
<211> LENGTH: 13

<212> TYPE: DNA
<213> ORGANISM: Artificial Sequence
<220> FEATURE:
<223> OTHER INFORMATION: Synthetic Sequence

<400> SEQUENCE: 379
tgtggaggta atc 13

<210> SEQ ID NO 380
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 380
tgatgaggtg atc 13

<210> SEQ ID NO 381
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 381
ggatgaggta atc 13

<210> SEQ ID NO 382
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 382
ccatgaggtg atc 13

<210> SEQ ID NO 383
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 383
catgaggtgt tc 12

<210> SEQ ID NO 384
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 384
ccgtgaggtg atc 13

<210> SEQ ID NO 385
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 385

-continued agaggaggta ttc 13

<210> SEQ ID NO 386
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 386
ttatgaggta atc 13

<210> SEQ ID NO 387
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 387
agttgaggtg atc 13

<210> SEQ ID NO 388
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 388
cttggaggtg ttc 13

<210> SEQ ID NO 389
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 389
tgaggaggtg ttc 13

<210> SEQ ID NO 390
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 390
gagggaggtg ttc 13

<210> SEQ ID NO 391
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 391
gtttgaggtg ttc 13

<210> SEQ ID NO 392
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 392
cagggaggtg ttc 13

<210> SEQ ID NO 393
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 393
cgaggaggtg atc 13

<210> SEQ ID NO 394
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 394
gcgtgaggtg ttc 13

<210> SEQ ID NO 395
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 395
taggaggtat tc 12

<210> SEQ ID NO 396
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 396
taggaggtgt tc 12

<210> SEQ ID NO 397
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 397
ccgtgaggta atc 13

<210> SEQ ID NO 398
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 398
ataggaggtg atc 13

<210> SEQ ID NO 399
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 399
gttggaggtg atc 13

<210> SEQ ID NO 400
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 400
cagggaggtg atc 13

<210> SEQ ID NO 401
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 401
ccaggaggta ttc 13

<210> SEQ ID NO 402
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 402
cgtgaggtga tc 12

<210> SEQ ID NO 403
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 403
atttgaggtg atc 13

<210> SEQ ID NO 404
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 404
aggggaggtg ttc 13

<210> SEQ ID NO 405
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 405
tcgtgaggta atc 13

<210> SEQ ID NO 406
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 406
gtttgaggta atc 13

<210> SEQ ID NO 407
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 407
tgggaggtgt tc 12

<210> SEQ ID NO 408
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 408
ttggaggtga tc 12

<210> SEQ ID NO 409
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 409
gaatgaggtg atc 13

<210> SEQ ID NO 410
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 410
cctggaggtg atc 13

<210> SEQ ID NO 411
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 411
ttgtgaggta ttc 13

<210> SEQ ID NO 412

<211> LENGTH: 13
<212> TYPE: DNA
<213> ORGANISM: Artificial Sequence
<220> FEATURE:
<223> OTHER INFORMATION: Synthetic Sequence

<400> SEQUENCE: 412
ttttgaggtg ttc 13

<210> SEQ ID NO 413
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 413
gaatgaggtg ttc 13

<210> SEQ ID NO 414
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 414
ctttgaggtg ttc 13

<210> SEQ ID NO 415
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 415
ccaggaggtg ttc 13

<210> SEQ ID NO 416
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 416
ggaggaggtg ttc 13

<210> SEQ ID NO 417
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 417
aggtgaggta ttc 13

<210> SEQ ID NO 418
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 418
ctaggaggta ttc 13

<210> SEQ ID NO 419
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 419
tttgaggtat tc 12

<210> SEQ ID NO 420
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 420
ccaggaggtg atc 13

<210> SEQ ID NO 421
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 421
aatggaggtg atc 13

<210> SEQ ID NO 422
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 422
gcgggaggta atc 13

<210> SEQ ID NO 423
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 423
gtgggaggta atc 13

<210> SEQ ID NO 424
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 424
ttgggaggtg atc 13

<210> SEQ ID NO 425
<211> LENGTH: 13
<212> TYPE: DNA

<213> ORGANISM: Artificial Sequence
<220> FEATURE:
<223> OTHER INFORMATION: Synthetic Sequence

<400> SEQUENCE: 425
gagtgaggta atc 13

<210> SEQ ID NO 426
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 426
cattgaggta atc 13

<210> SEQ ID NO 427
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 427
attgaggtaa tc 12

<210> SEQ ID NO 428
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 428
aaaggaggta atc 13

<210> SEQ ID NO 429
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 429
cgaggaggta ttc 13

<210> SEQ ID NO 430
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 430
ctttgaggtg atc 13

<210> SEQ ID NO 431
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 431
tgttgaggtg ttc 13

<210> SEQ ID NO 432
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 432
tcttgaggtg atc 13

<210> SEQ ID NO 433
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 433
ttttgaggta ttc 13

<210> SEQ ID NO 434
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 434
gttgaggtgt tc 12

<210> SEQ ID NO 435
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 435
aagtgaggtg atc 13

<210> SEQ ID NO 436
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 436
ccgggaggtg atc 13

<210> SEQ ID NO 437
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 437
tatgaggtga tc 12

<210> SEQ ID NO 438
<211> LENGTH: 13
<212> TYPE: DNA
<213> ORGANISM: Artificial Sequence
<220> FEATURE:

<223> OTHER INFORMATION: Synthetic Sequence

<400> SEQUENCE: 438
catggaggta atc 13

<210> SEQ ID NO 439
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 439
gctggaggta ttc 13

<210> SEQ ID NO 440
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 440
atgtgaggta atc 13

<210> SEQ ID NO 441
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 441
tgatgaggta atc 13

<210> SEQ ID NO 442
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 442
atgggaggtg atc 13

<210> SEQ ID NO 443
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 443
aatgaggtat tc 12

<210> SEQ ID NO 444
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 444
tagtgaggtg ttc 13

<210> SEQ ID NO 445
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 445
gtgtgaggta atc 13

<210> SEQ ID NO 446
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 446
atgtgaggtg ttc 13

<210> SEQ ID NO 447
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 447
ctggaggtga tc 12

<210> SEQ ID NO 448
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 448
ccttgaggtg atc 13

<210> SEQ ID NO 449
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 449
gagtgaggta ttc 13

<210> SEQ ID NO 450
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 450
agttgaggta atc 13

<210> SEQ ID NO 451
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 451
gcaggaggta ttc 13

<210> SEQ ID NO 452
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 452
taatgaggta ttc 13

<210> SEQ ID NO 453
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 453
caaggaggta atc 13

<210> SEQ ID NO 454
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 454
tggtgaggtg ttc 13

<210> SEQ ID NO 455
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 455
tggtgaggtg atc 13

<210> SEQ ID NO 456
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 456
cattgaggtg atc 13

<210> SEQ ID NO 457
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 457
gattgaggtg ttc 13

<210> SEQ ID NO 458
<211> LENGTH: 12

<212> TYPE: DNA
<213> ORGANISM: Artificial Sequence
<220> FEATURE:
<223> OTHER INFORMATION: Synthetic Sequence

<400> SEQUENCE: 458
attgaggtga tc 12

<210> SEQ ID NO 459
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 459
gcgggaggtg ttc 13

<210> SEQ ID NO 460
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 460
ttgggaggtg ttc 13

<210> SEQ ID NO 461
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 461
atatgaggtg ttc 13

<210> SEQ ID NO 462
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 462
acgtgaggtg ttc 13

<210> SEQ ID NO 463
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 463
ccttgaggtg ttc 13

<210> SEQ ID NO 464
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 464
gcgggaggtg atc 13

<210> SEQ ID NO 465
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 465
acaggaggtg ttc 13

<210> SEQ ID NO 466
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 466
atggaggtga tc 12

<210> SEQ ID NO 467
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 467
ctgtgaggta ttc 13

<210> SEQ ID NO 468
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 468
ttttgaggtg atc 13

<210> SEQ ID NO 469
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 469
attggaggta atc 13

<210> SEQ ID NO 470
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 470
gggtgaggtg ttc 13

<210> SEQ ID NO 471
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 471
tggtgaggta atc 13

<210> SEQ ID NO 472
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 472
tgtgaggtaa tc 12

<210> SEQ ID NO 473
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 473
aattgaggtg atc 13

<210> SEQ ID NO 474
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 474
agttgaggta ttc 13

<210> SEQ ID NO 475
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 475
gcaggaggta atc 13

<210> SEQ ID NO 476
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 476
agatgaggta ttc 13

<210> SEQ ID NO 477
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 477
ggtggaggtg atc 13

<210> SEQ ID NO 478
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 478
taaggaggtg atc 13

<210> SEQ ID NO 479
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 479
tcgggaggtg atc 13

<210> SEQ ID NO 480
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 480
tcgggaggtg ttc 13

<210> SEQ ID NO 481
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 481
gagtgaggtg ttc 13

<210> SEQ ID NO 482
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 482
aagtgaggta atc 13

<210> SEQ ID NO 483
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 483
ggggaggtaa tc 12

<210> SEQ ID NO 484
<211> LENGTH: 40
<212> TYPE: DNA
<213> ORGANISM: Artificial Sequence
<220> FEATURE:
<223> OTHER INFORMATION: Synthetic Sequence -continued

<400> SEQUENCE: 484
cctaagagca agaagaagcc taaggaggtg atccaaccgc 40

<210> SEQ ID NO 485
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 485
ggcttcttct tgctcttagg tagtaggttc 30

<210> SEQ ID NO 486
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 486
cctaagagca agaagaagcc taaggaggtg atccagcgcc 40

<210> SEQ ID NO 487
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 487
cctaagagca agaagaagcc aggaggtgat ccagccgcag 40

<210> SEQ ID NO 488
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 488
cgtgcgcttt acgccca 17

METHODS OF PRODUCING RIBOSOMAL RIBONUCLEIC ACID COMPLEXES

CROSS-REFERENCE TO RELATED APPLICATIONS

This application claims the benefit of U.S. Provisional Patent Application No. 62/490,992, filed Apr. 27, 2017, which application is incorporated herein by reference in its entirety.

INTRODUCTION

Recent advances in DNA sequencing have revolutionized the field of genomics, making it possible for even single research groups to generate large amounts of sequence data very rapidly and at a substantially lower cost. These high-throughput sequencing technologies make deep transcriptome sequencing and transcript quantification, whole genome sequencing and resequencing available to many more researchers and projects.

A variety of commercial high-throughput sequencing platforms exist and are described, e.g., in Metzker, M. L. (2010) *Nat. Rev. Genet.* 11:31-46, Morey et al. (2013) *Mol. Genet. Metab.* 110: 3-24, Reuter et al. (2015) *Molecular Cell* 58(4):586-597, and elsewhere. In the Illumina platform, the sequencing process involves clonal amplification of adaptor-ligated DNA fragments on the surface of a glass slide. Bases are read using a cyclic reversible termination strategy, which sequences the template strand one nucleotide at a time through progressive rounds of base incorporation, washing, imaging, and cleavage. In this strategy, fluorescently labeled 3'-O-azidomethyl-dNTPs are used to pause the polymerization reaction, enabling removal of unincorporated bases and fluorescent imaging to determine the added nucleotide. Following scanning of the flow cell with a coupled-charge device (CCD) camera, the fluorescent moiety and the 3' block are removed, and the process is repeated.

An emerging single-molecule strategy that has made significant progress in recent years is nanopore-based sequencing, with Oxford Nanopore Technologies leading the development and commercialization of this method. Nanopore sequencing principally relies on the transition of DNA or individual nucleotides through a small channel. A sequencing flow cell includes hundreds of independent micro-wells, each containing a synthetic bilayer perforated by biologic nanopores. Sequencing is accomplished by measuring characteristic changes in current that are induced as the bases are threaded through the pore by a molecular motor protein. Library preparation is minimal, involving fragmentation of DNA and ligation of adapters, and can be done with or without PCR amplification. The library design allows sequencing of both strands of DNA from a single molecule, which increases accuracy.

Ribosomal ribonucleic acid (rRNA) sequencing (e.g. 16S rRNA sequencing) is a method that can be used to identify organisms (e.g., eukaryotic and/or prokaryotic organisms) present within a given sample. 16S rRNA gene sequencing is an established method for studying phylogeny and taxonomy of samples from complex microbiomes or environments that are difficult or impossible to study. Unlike capillary sequencing or PCR-based approaches, next-generation sequencing (NGS) is a culture-free method that enables analysis of, e.g., the entire microbial community, within a sample. With the ability to combine many samples in a sequencing run, researchers can use NGS-based rRNA sequencing as a cost-effective technique to identify organisms (e.g., strains) that may not be found using other methods.

SUMMARY

Provided are methods of producing a nucleic acid complex. In certain aspects, the methods include combining a sample including ribosomal RNA (rRNA) and a probe complement oligonucleotide with an oligonucleotide probe. The oligonucleotide probe includes a 3' region complementary to a 3' region of a rRNA, and a 5' region complementary to the probe complement oligonucleotide. The combining is under conditions in which the 3' region of the oligonucleotide probe hybridizes to the 3' region of the rRNA and the 5' region of the oligonucleotide probe hybridizes to the probe complement oligonucleotide, thereby producing a nucleic acid complex. In certain aspects, the methods find use in producing rRNA libraries that find use, e.g., in rRNA sequencing applications. Oligonucleotide probes, libraries thereof, compositions, and kits that find use, e.g., in practicing the methods of the present disclosure, are also provided.

BRIEF DESCRIPTION OF THE FIGURES

Some of the figures are better understood when provided in color. Applicant submits that the color versions of the figures are part of the original disclosure and reserves the right to provide color versions of the figures in later proceedings.

DETAILED DESCRIPTION

Figure 1:
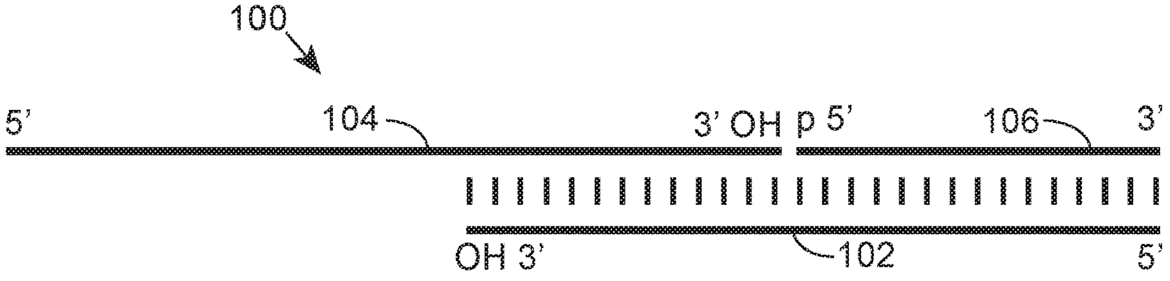
FIG. 1 schematically illustrates a nucleic acid complex produced according to one embodiment of the present disclosure.

Provided are methods of producing a nucleic acid complex. In certain aspects, the methods include combining a sample including ribosomal RNA (rRNA) and a probe complement oligonucleotide with an oligonucleotide probe. The oligonucleotide probe includes a 3' region complementary to a 3' region of a rRNA, and a 5' region complementary to the probe complement oligonucleotide. The combining is under conditions in which the 3' region of the oligonucleotide probe hybridizes to the 3' region of the rRNA and the 5' region of the oligonucleotide probe hybridizes to the probe complement oligonucleotide, thereby producing a nucleic acid complex. In certain aspects, the methods find use in producing rRNA libraries that find use, e.g., in rRNA sequencing applications. Oligonucleotide probes, libraries thereof, compositions, and kits that find use, e.g., in practicing the methods of the present disclosure, are also provided.

Before the methods, oligonucleotide probes, libraries, compositions and kits of the present disclosure are described in greater detail, it is to be understood that the methods, oligonucleotide probes, libraries, compositions and kits are not limited to particular embodiments described, as such may, of course, vary. It is also to be understood that the terminology used herein is for the purpose of describing particular embodiments only, and is not intended to be limiting, since the scope of the methods, oligonucleotide probes, libraries, compositions and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, oligonucleotide probes, libraries, compositions and kits. The upper and lower limits of these smaller ranges may independently be included in the smaller ranges and are also encompassed within the methods, oligonucleotide probes, libraries, compositions and kits, subject to any specifically excluded limit in the stated range. Where the stated range includes one or both of the limits, ranges excluding either or both of those included limits are also included in the methods, oligonucleotide probes, libraries, compositions and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods, oligonucleotide probes, libraries, compositions and kits belong. Although any methods, oligonucleotide probes, libraries, compositions and kits similar or equivalent to those described herein can also be used in the practice or testing of the methods, oligonucleotide probes, libraries, compositions and kits, representative illustrative methods, oligonucleotide probes, libraries, compositions and kits are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, oligonucleotide probes, libraries, compositions and kits are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, oligonucleotide probes, libraries, compositions and kits, which are, for clarity, described in the context of separate embodiments, may also be provided in combination in a single embodiment. Conversely, various features of the methods, oligonucleotide probes, libraries, compositions and kits, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods, oligonucleotide probes, libraries, compositions and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods

As summarized above, the present disclosure provides methods for producing nucleic acid complexes. In some embodiments, the methods include combining a sample including ribosomal RNA (rRNA) and a probe complement oligonucleotide with an oligonucleotide probe. The oligonucleotide probe includes a 3' region complementary to a 3' region of a rRNA, and a 5' region complementary to the probe complement oligonucleotide. The combining is under conditions in which the 3' region of the oligonucleotide probe hybridizes to the 3' region of the rRNA and the 5' region of the oligonucleotide probe hybridizes to the probe complement oligonucleotide, to produce a nucleic acid complex. The nucleic acid complex includes the oligonucleotide probe hybridized to the 3' region of the rRNA and the probe complement oligonucleotide. In some embodiments, the oligonucleotide probe is designed such that it hybridizes to the rRNA and probe complement oligonucleotide in a manner such that the rRNA and probe complement oligonucleotide are in the same orientation with respect to their 5' and 3' ends (see, e.g., FIG. 1).

A nucleic acid complex according to one embodiment is schematically illustrated in FIG. 1. As shown, a 3' region of oligonucleotide probe 102 is complementary and hybridized to a 3' region of rRNA 104. A 5' region of oligonucleotide probe 102 is complementary and hybridized to complement oligonucleotide 106. Details regarding example embodiments of the methods will now be described.

The sample including, or suspected of including, rRNA may vary. In certain aspects, the sample is a medical sample. Medical samples of interest include, but are not limited to, samples obtained from an animal. In some embodiments, the animal is a mammal, e.g., a mammal from the genus Homo, a rodent (e.g., a mouse or rat), a dog, a cat, a horse, a cow, or any other mammal of interest. In certain aspects, the medical sample is obtained from a tissue, organ, or the like from an animal. In some embodiments, the medical sample is a body fluid sample. In certain aspects, the medical sample is a body fluid sample selected from whole blood, blood plasma, blood serum, saliva, mucus, sputum, amniotic fluid, urine, pleural effusion, bronchial lavage, bronchial aspirates, breast milk, colostrum, tears, seminal fluid, peritoneal fluid, pleural effusion, and stool.

In some embodiments, the sample including, or suspected of including, rRNA is an environmental sample. In certain aspects, the environmental sample is a gaseous environmental sample. The gaseous environmental sample may be, e.g., a stack gas, atmospheric air, indoor air, workplace atmosphere, landfill gas, industrial gas, exhaled breath, biogenic emissions, leaks from industrial installations, or the like. In some embodiments, the environmental sample is a liquid environmental sample. The liquid environmental sample may be, e.g., drinking (or potable) water, surface water (e.g., river water, stream water, lake water, reservoir water, wetland water, bog water, or the like), ground water, waste water, well water, water from an unsaturated zone, rain water, run-off water, sea water, liquid industrial waste, sewage, surface films, or the like. In certain aspects, the environmental sample is a solid environmental sample. The solid environmental sample may be, e.g., ice, snow, soil, sewage sludge, bottom sediments, dust from electrofilters, vacuuming dust, plant material, forest floor, industrial waste, municipal waste, ashes, or the like.

In certain aspects, the sample including rRNA which is combined with the probe complement oligonucleotide and the oligonucleotide probe is a sample that has been purified from any of the sample types described above. The sample may be a sample resulting from a nucleic acid isolation procedure. Approaches, reagents and kits for isolating nucleic acids from sources of interest are known in the art and commercially available. For example, kits for isolating nucleic acids from a source of interest include the DNeasy®, RNeasy®, QIAamp®, QIAprep® and QIAquick® nucleic acid isolation/purification kits by Qiagen, Inc. (Germantown, Md.); the DNAzol®, ChargeSwitch®, Purelink®, GeneCatcher® nucleic acid isolation/purification kits by Life Technologies, Inc. (Carlsbad, Calif.); the NucleoMag®, NucleoSpin®, and NucleoBond® nucleic acid isolation/purification kits by Clontech Laboratories, Inc. (Mountain View, Calif.). In certain aspects, the nucleic acid is isolated from a fixed biological sample, e.g., formalin-fixed, paraffin-embedded (FFPE) tissue. Genomic DNA from FFPE tissue may be isolated using commercially available kits—such as the AllPrep® DNA/RNA FFPE kit by Qiagen, Inc. (Germantown, Md.), the RecoverAll® Total Nucleic Acid Isolation kit for FFPE by Life Technologies, Inc. (Carlsbad, Calif.), and the NucleoSpin® FFPE kits by Clontech Laboratories, Inc. (Mountain View, Calif.).

The sample includes, or is suspected of including, one or more rRNAs of interest. The one or more rRNAs of interest may be considered "target" rRNA, where the oligonucleotide probe (which may or may not be present in an oligonucleotide probe library) is designed to include a 3' region sufficiently complementary to a region (e.g., a 3' region) of the target rRNA such that specific hybridization between the 3' region of the oligonucleotide probe and the target rRNA is achieved. In this way, the sample may be interrogated for the presence of an rRNA of interest (e.g., by downstream next-generation sequencing, real-time polymerase chain reaction, or the like), e.g., an rRNA from a particular organism or strain thereof to determine whether the organism is present in the sample, and if desired, quantitate the level of the organism in the sample based on the level of the rRNA in the sample.

The 3' region of the oligonucleotide probe may be designed to specifically hybridize to a variety of rRNAs of interest, e.g., based on known rRNA sequence information. In some embodiments, the target rRNA is a eukaryotic rRNA. Eukaryotic rRNAs of interest include, e.g., 28S rRNA, 18S rRNA, 5.8S rRNA, 5S rRNA, and any combination thereof. In some embodiments, a eukaryotic rRNA of interest is an 18S eukaryotic rRNA. In certain aspects, when the rRNA of interest is an 18S eukaryotic rRNA, the 3' region of the oligonucleotide probe terminates with the nucleotide sequence: 5'-TAATGATCCTTCC-3' (SEQ ID NO:1). The 3' region of the oligonucleotide probe may be designed to specifically hybridize to an rRNA of a particular eukaryotic organism. In some embodiments, the eukaryotic organism is a protozoa, algae, fungus (e.g., yeast), plant, insect, or animal.

In certain aspects, the target rRNA is a prokaryotic rRNA, e.g., a bacterial rRNA or an archaea rRNA. Prokaryotic rRNAs of interest include, e.g., 23S rRNA, 16S rRNA, 5S rRNA, and any combination thereof. In some embodiments, a prokaryotic rRNA of interest is a 23S prokaryotic rRNA. In certain aspects, when the rRNA of interest is a 23S prokaryotic rRNA, the 3' region of the oligonucleotide probe terminates with the nucleotide sequence: 5'-AAGGTTAAGCCTC-3' (SEQ ID NO:2).

Sequence information that can be used to design the oligonucleotide probes of the present disclosure for hybridization to particular rRNAs of interest is readily available at a variety of nucleic acid sequence databases, including, e.g., the National Institutes of Health's GenBank® genetic sequence database. A comprehensive online resource for quality-checked and aligned rRNA sequence data is the SILVA database. See, e.g., Quast et al. (2013) *Nucleic Acids Res.* 41 (D1): D590-D596; and Yilmaz et al. (2014) *Nucleic Acids Res.* 42 (D1): D643-D648.

In some embodiments, the methods employ a library of oligonucleotide probes. According to methods that employ a library of oligonucleotide probes, the combining includes combining a library of oligonucleotide probes, the oligonucleotide probes of the library including a 3' region complementary to a 3' region of a rRNA, and a 5' region complementary to a probe complement oligonucleotide, where the library includes a plurality of (e.g., 2 or more) unique oligonucleotide probes that differ from one another with respect to the nucleotide sequence of the 3' region, the nucleotide sequence of the 5' region, or both, to produce a plurality of unique nucleic acid complexes. For example, the library may include a plurality of unique oligonucleotide probes having 3' regions designed to target the 3' regions of different types of rRNAs. As just one example, the library may include a plurality of unique oligonucleotide probes having 3' regions designed to target the 3' regions of 16S rRNAs from different prokaryotic organisms and/or strains thereof. As will be appreciated in view of the present disclosure, when the library includes unique oligonucleotide probes that differ from one another at least with respect to the 5' region that hybridizes to a probe complement oligonucleotide, a plurality of corresponding unique probe complement oligonucleotides may be employed when practicing the methods.

An oligonucleotide probe library of the present disclosure includes a plurality of (e.g., 2 or more) unique oligonucleotide probes that differ from one another with respect to the nucleotide sequence of the 3' region, the nucleotide sequence of the 5' region, or both. In certain aspects, the plurality of unique oligonucleotide probes includes 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 25 or more, 30 or more, 35 or more, 40 or more, 45 or more, 50 or more, 55 or more, 60 or more, 65 or more, 70 or more, 75 or more, 80 or more, 85 or more, 90 or more, 95 or more, 100 or more, 110 or more, 120 or more, 130 or more, 140 or more, 150 or more, 160 or more, 170 or more, 180 or more, 190 or more, 200 or more, 210 or more, 220 or more, 230 or more, 240 or more, 250 or more, 260 or more, 270 or more, 280 or more, 290 or more, 300 or more, 310 or more, 320 or more, 330 or more, 340 or more, 350 or more, 360 or more, 370 or more, 380 or more, 390 or more, or 400 or more unique oligonucleotide probes. In some embodiments, the number of unique oligonucleotide probes corresponds to a number of unique 3' oligonucleotide probe regions complementary to a corresponding number of different target rRNAs of interest.

In certain aspects, an rRNA of interest is the prokaryotic 16S rRNA. In some embodiments, when an rRNA of interest is the prokaryotic 16S rRNA, the 3' region of the oligonucleotide probe is designed to be complementary and hybridize to a region that includes the anti-Shine-Dalgarno sequence or sub-sequence thereof of the 16S rRNA. In certain aspects, the 3' region of the oligonucleotide probe is designed such that the 3' region is complementary and hybridizes exclusively to the anti-Shine-Dalgarno sequence or sub-sequence thereof of the 16S rRNA. In other aspects, the 3' region of the oligonucleotide probe is designed such that the 3' region is complementary and hybridizes to the anti-Shine-Dalgarno sequence or sub-sequence thereof, and also to one or more nucleotides 5', 3', or both, of the anti-Shine-Dalgarno sequence. For example, the 3' region of the oligonucleotide probe may be designed such that the 3' region is complementary and hybridizes to the anti-Shine-Dalgarno sequence or sub-sequence thereof, and also to one or more nucleotides 5' of the anti-Shine-Dalgarno sequence. In some embodiments, hybridization to a region 5', 3', or both, of the anti-Shine-Dalgarno sequence may be beneficial, e.g., for conferring specificity (or enhanced specificity) of the oligonucleotide probe for a 16S rRNA of particular prokaryotic organism or strain thereof.

In certain aspects, when the rRNA of interest is a 16S prokaryotic rRNA, the 3' region of the oligonucleotide probe terminates with the nucleotide sequence: 5'-$X^1X^2X^3X^4$GAGGT$X^5X^6$TC-3' (SEQ ID NO:3), where:

$X^1$=A, C, G, T or Z, where Z is the absence of a base at that position;

$X^2$=A, C, G, T or Z, where Z is the absence of a base at that position;

$X^3$=A, T or G;

$X^4$=G or T;

$X^5$=G or A; and $X^6$=A or T.

In some embodiments, when the rRNA of interest is a 16S prokaryotic rRNA, the 3' region of the oligonucleotide probe terminates with a nucleotide sequence present in Table 1. In certain aspects, when the rRNA of interest is a 16S prokaryotic rRNA, the 3' region of the oligonucleotide probe terminates with the nucleotide sequence: 5'-AAAGGAGGTGATC-3' (SEQ ID NO:70).

In some embodiments, when a library of oligonucleotide probes is employed, the library may include a plurality of unique oligonucleotide probes that differ from one another with respect to the terminal nucleotide sequence of the 3' region. In certain aspects, such a plurality of unique oligonucleotide probes have 3' regions that terminate with 2 or more (that is, any combination) of any of the nucleotide sequences present in Table 1. For example, 2 or more, 5 or more, 10 or more, 20 or more, 30 or more, 40 or more, 50 or more, 60 or more, 70 or more, 80 or more, 90 or more, 100 or more, 120 or more, 140 or more, 160 or more, 180 or more, 200 or more, 220 or more, 240 or more, 260 or more, 280 or more, 300 or more, 320 or more, 340 or more, 360 or more, 380 or more, 400 or more, 420 or more, 440 or more, 460 or more, or each of the oligonucleotide probe 3' region nucleotide sequences present in Table 1 may be represented in such a library.

TABLE 1

| Oligonucleotide Probe 3' regions (Prokaryotic 16S Sequences (5' → 3')) | SEQ ID NO |
|---|---|
| CCATGAGGTGTTC | 4 |
| TAAGGAGGTATTC | 5 |
| AATGAGGTGTTC | 6 |
| GCATGAGGTAATC | 7 |
| TCAGGAGGTAATC | 8 |
| TAGGGAGGTAATC | 9 |
| CGATGAGGTGATC | 10 |
| CGGTGAGGTGTTC | 11 |
| GTGGGAGGTGATC | 12 |
| CGTGAGGTAATC | 13 |
| AGTGGAGGTATTC | 14 |
| CCGGGAGGTGTTC | 15 |
| CGGTGAGGTATTC | 16 |
| TCATGAGGTATTC | 17 |
| TGTGAGGTATTC | 18 |
| CGGGAGGTGTTC | 19 |
| CTTTGAGGTAATC | 20 |
| CAAGGAGGTATTC | 21 |
| GTTTGAGGTATTC | 22 |
| AGATGAGGTGATC | 23 |
| GGTGAGGTGATC | 24 |
| TTTGAGGTGTTC | 25 |
| AGAGGAGGTAATC | 26 |
| GTGTGAGGTGATC | 27 |

TABLE 1-continued

Oligonucleotide Probe 3' regions (Prokaryotic 16S Sequences (5' → 3'))

| | SEQ ID NO |
|---|---|
| CGGTGAGGTAATC | 28 |
| CTGGGAGGTAATC | 29 |
| AGGTGAGGTGATC | 30 |
| GAGGAGGTATTC | 31 |
| AATTGAGGTGTTC | 32 |
| ATGTGAGGTGATC | 33 |
| CAGGAGGTGATC | 34 |
| GATGAGGTGATC | 35 |
| TTGTGAGGTGATC | 36 |
| CGGGGAGGTGTTC | 37 |
| CGGGAGGTGATC | 38 |
| CTTTGAGGTATTC | 39 |
| TTATGAGGTGATC | 40 |
| GGTGGAGGTATTC | 41 |
| GGATGAGGTGTTC | 42 |
| TCGTGAGGTGTTC | 43 |
| AGGGAGGTGATC | 44 |
| TATGGAGGTATTC | 45 |
| GTTGGAGGTGTTC | 46 |
| GATGGAGGTGATC | 47 |
| GGGGGAGGTGATC | 48 |
| ACGGGAGGTGATC | 49 |
| GGGTGAGGTAATC | 50 |
| AAGGGAGGTGATC | 51 |
| GTTGGAGGTAATC | 52 |
| ACGTGAGGTATTC | 53 |
| GGTGAGGTGTTC | 54 |
| CAGGAGGTATTC | 55 |
| AAGTGAGGTGTTC | 56 |
| GGAGGAGGTGATC | 57 |
| AAGGAGGTAATC | 58 |
| GATTGAGGTATTC | 59 |
| AGAGGAGGTGATC | 60 |
| TAGTGAGGTGATC | 61 |
| GTGGGAGGTGTTC | 62 |
| ATGGGAGGTATTC | 63 |
| CAGTGAGGTATTC | 64 |
| TAGGGAGGTGTTC | 65 |
| TTTGGAGGTGTTC | 66 |
| TTGGGAGGTATTC | 67 |
| GTGGGAGGTATTC | 68 |
| AATGAGGTAATC | 69 |
| AAAGGAGGTGATC | 70 |
| ACGGGAGGTATTC | 71 |
| CTAGGAGGTAATC | 72 |
| GGGTGAGGTATTC | 73 |
| CGTGAGGTATTC | 74 |
| ATGGAGGTAATC | 75 |
| CGTGGAGGTATTC | 76 |
| AAATGAGGTATTC | 77 |
| CCTGGAGGTGTTC | 78 |
| TAGGAGGTAATC | 79 |
| GTTGAGGTGATC | 80 |
| CGTGGAGGTGTTC | 81 |
| CTTGGAGGTAATC | 82 |
| ATTTGAGGTGTTC | 83 |
| AATGGAGGTGTTC | 84 |
| TCTGGAGGTGTTC | 85 |
| GTAGGAGGTGTTC | 86 |
| ACGGGAGGTGTTC | 87 |
| TATGGAGGTAATC | 88 |
| AGGGAGGTGTTC | 89 |
| CGAGGAGGTAATC | 90 |
| TGTTGAGGTGATC | 91 |
| CTATGAGGTGATC | 92 |
| TATTGAGGTATTC | 93 |
| CTGGAGGTATTC | 94 |
| CTTGAGGTGATC | 95 |
| TGTGGAGGTGTTC | 96 |
| TTTGGAGGTAATC | 97 |
| CGTGGAGGTGATC | 98 |
| TATTGAGGTGTTC | 99 |
| AATTGAGGTAATC | 100 |
| GGTTGAGGTGTTC | 101 |
| TTAGGAGGTGTTC | 102 |

TABLE 1-continued

| Oligonucleotide Probe 3' regions (Prokaryotic 16S Sequences (5' → 3')) | SEQ ID NO |
|---|---|
| CATGGAGGTGATC | 103 |
| TTTGGAGGTATTC | 104 |
| CTGGAGGTAATC | 105 |
| CATGGAGGTGTTC | 106 |
| GAGGAGGTGATC | 107 |
| ATATGAGGTAATC | 108 |
| GTGGAGGTATTC | 109 |
| CATTGAGGTGTTC | 110 |
| AGGGAGGTAATC | 111 |
| ATTTGAGGTATTC | 112 |
| AGGGGAGGTAATC | 113 |
| TCTGGAGGTGATC | 114 |
| TGGGGAGGTGTTC | 115 |
| CGAGGAGGTGTTC | 116 |
| TTGGAGGTATTC | 117 |
| GGATGAGGTATTC | 118 |
| CTATGAGGTATTC | 119 |
| TTTTGAGGTAATC | 120 |
| TTTGAGGTGATC | 121 |
| ACATGAGGTATTC | 122 |
| GTGGAGGTAATC | 123 |
| TCAGGAGGTGTTC | 124 |
| TGGGAGGTAATC | 125 |
| TGTTGAGGTATTC | 126 |
| TGTGGAGGTATTC | 127 |
| GGTTGAGGTAATC | 128 |
| ATAGGAGGTAATC | 129 |
| CATGGAGGTATTC | 130 |
| CAATGAGGTGTTC | 131 |
| GTTGGAGGTATTC | 132 |
| GGGGAGGTGTTC | 133 |
| GTATGAGGTGATC | 134 |
| CGTTGAGGTATTC | 135 |
| TAGTGAGGTAATC | 136 |
| CAGGGAGGTAATC | 137 |
| GTGTGAGGTGTTC | 138 |
| ATGGGAGGTGTTC | 139 |

TABLE 1-continued

| Oligonucleotide Probe 3' regions (Prokaryotic 16S Sequences (5' → 3')) | SEQ ID NO |
|---|---|
| CTAGGAGGTGATC | 140 |
| AGTGAGGTAATC | 141 |
| GTAGGAGGTATTC | 142 |
| ACAGGAGGTATTC | 143 |
| TATTGAGGTGATC | 144 |
| AGTTGAGGTGTTC | 145 |
| GCAGGAGGTGTTC | 146 |
| TTGGGAGGTAATC | 147 |
| TGGGGAGGTAATC | 148 |
| GGTGGAGGTGTTC | 149 |
| TGAGGAGGTGATC | 150 |
| CCGGGAGGTAATC | 151 |
| TAATGAGGTGTTC | 152 |
| TAATGAGGTGATC | 153 |
| GCTGGAGGTGATC | 154 |
| TCAGGAGGTATTC | 155 |
| CGATGAGGTAATC | 156 |
| CTGGGAGGTATTC | 157 |
| CTATGAGGTAATC | 158 |
| CCTTGAGGTATTC | 159 |
| GCGGGAGGTATTC | 160 |
| ACGGGAGGTAATC | 161 |
| ACAGGAGGTAATC | 162 |
| GCTTGAGGTATTC | 163 |
| AAATGAGGTGTTC | 164 |
| CGATGAGGTATTC | 165 |
| AAGGGAGGTGTTC | 166 |
| GATTGAGGTAATC | 167 |
| ATATGAGGTATTC | 168 |
| GATGGAGGTGTTC | 169 |
| GATGAGGTGTTC | 170 |
| CGGGGAGGTAATC | 171 |
| TAATGAGGTAATC | 172 |
| AGTGGAGGTGATC | 173 |
| GAGGGAGGTGATC | 174 |
| ACTGGAGGTGTTC | 176 |
| ACTGGAGGTGATC | 177 |
| ACTTGAGGTGTTC | 178 |

TABLE 1-continued

| Oligonucleotide Probe 3' regions (Prokaryotic 16S Sequences (5' → 3')) | |
|---|---|
| | SEQ ID NO |
| CCGGGAGGTATTC | 179 |
| ATTGAGGTATTC | 180 |
| GAAGGAGGTAATC | 181 |
| AGATGAGGTAATC | 182 |
| TCGTGAGGTATTC | 183 |
| AGTGAGGTGATC | 184 |
| TCTTGAGGTGTTC | 185 |
| TTAGGAGGTATTC | 186 |
| TTGTGAGGTAATC | 187 |
| ACGTGAGGTGATC | 188 |
| TTTGAGGTAATC | 189 |
| TTGGAGGTGTTC | 190 |
| CGTTGAGGTAATC | 191 |
| AATTGAGGTATTC | 192 |
| TTTGGAGGTGATC | 193 |
| TGATGAGGTATTC | 194 |
| AGATGAGGTGTTC | 195 |
| CTGTGAGGTGATC | 196 |
| CAATGAGGTATTC | 197 |
| GGTTGAGGTATTC | 198 |
| CTTGGAGGTGATC | 199 |
| GAGTGAGGTGATC | 200 |
| CCTGGAGGTATTC | 201 |
| TGGGAGGTGATC | 202 |
| GGGGGAGGTAATC | 203 |
| CGGGGAGGTATTC | 204 |
| ATTGGAGGTGTTC | 205 |
| TATGGAGGTGTTC | 206 |
| AGTGGAGGTAATC | 207 |
| GTTGAGGTATTC | 208 |
| GGGGAGGTGATC | 209 |
| ACTGGAGGTATTC | 210 |
| ACTTGAGGTATTC | 211 |
| GAAGGAGGTGTTC | 212 |
| TCTTGAGGTAATC | 213 |
| CTTGAGGTATTC | 214 |
| TCTTGAGGTATTC | 215 |

TABLE 1-continued

| Oligonucleotide Probe 3' regions (Prokaryotic 16S Sequences (5' → 3')) | |
|---|---|
| | SEQ ID NO |
| GCATGAGGTATTC | 216 |
| GAATGAGGTAATC | 217 |
| CATGAGGTATTC | 218 |
| CCATGAGGTATTC | 219 |
| TGTGAGGTGATC | 220 |
| AGGGAGGTATTC | 221 |
| GATGGAGGTATTC | 222 |
| AAAGGAGGTATTC | 223 |
| GGGGAGGTATTC | 224 |
| AATGGAGGTAATC | 225 |
| TCGGGAGGTAATC | 226 |
| GATTGAGGTGATC | 227 |
| ATAGGAGGTGTTC | 228 |
| CCTGGAGGTAATC | 229 |
| CGTGAGGTGTTC | 230 |
| GGATGAGGTGATC | 231 |
| GAGGGAGGTAATC | 232 |
| AGTGGAGGTGTTC | 233 |
| AGTGAGGTGTTC | 234 |
| GGGGGAGGTATTC | 235 |
| TGTGGAGGTGATC | 236 |
| CTTGAGGTGTTC | 237 |
| ATAGGAGGTATTC | 238 |
| TATGAGGTAATC | 239 |
| CAATGAGGTAATC | 240 |
| GTATGAGGTAATC | 241 |
| CGTGGAGGTAATC | 242 |
| CTGGGAGGTGTTC | 243 |
| AAGGAGGTGTTC | 244 |
| CAGGGAGGTATTC | 245 |
| AAAGGAGGTGTTC | 246 |
| CTGTGAGGTAATC | 247 |
| CTAGGAGGTGTTC | 248 |
| AGGGGAGGTATTC | 249 |
| GGTTGAGGTGATC | 250 |
| GATGGAGGTAATC | 251 |
| TGGGAGGTATTC | 252 |
| TCAGGAGGTGATC | 253 |

TABLE 1-continued

| Oligonucleotide Probe 3' regions (Prokaryotic 16S Sequences (5' → 3')) | SEQ ID NO |
|---|---|
| TAGGAGGTGATC | 254 |
| GTTGAGGTAATC | 255 |
| ATGGAGGTGTTC | 256 |
| CAGGAGGTAATC | 257 |
| AGGGGAGGTGATC | 258 |
| GGAGGAGGTATTC | 259 |
| CAGGAGGTGTTC | 260 |
| CCTTGAGGTAATC | 261 |
| ACGTGAGGTAATC | 262 |
| TCTGGAGGTAATC | 263 |
| TATGAGGTGTTC | 264 |
| TATTGAGGTAATC | 265 |
| GTAGGAGGTGATC | 266 |
| GCTGGAGGTAATC | 267 |
| TTAGGAGGTAATC | 268 |
| TTATGAGGTGTTC | 269 |
| GCTTGAGGTGATC | 270 |
| TGAGGAGGTATTC | 271 |
| TTGGAGGTAATC | 272 |
| TCTGGAGGTATTC | 273 |
| CATTGAGGTATTC | 274 |
| ACATGAGGTGATC | 275 |
| CAAGGAGGTGATC | 276 |
| TTGTGAGGTGTTC | 277 |
| TGTTGAGGTAATC | 278 |
| GCTGGAGGTGTTC | 279 |
| TAAGGAGGTGTTC | 280 |
| TCATGAGGTAATC | 281 |
| ATGGGAGGTAATC | 282 |
| AGGTGAGGTGTTC | 283 |
| TGATGAGGTGTTC | 284 |
| CTATGAGGTGTTC | 285 |
| AGGTGAGGTAATC | 286 |
| AAGTGAGGTATTC | 287 |
| GGTGGAGGTAATC | 288 |
| GCGTGAGGTAATC | 289 |
| TGGTGAGGTATTC | 290 |

TABLE 1-continued

| Oligonucleotide Probe 3' regions (Prokaryotic 16S Sequences (5' → 3')) | SEQ ID NO |
|---|---|
| GCAGGAGGTGATC | 291 |
| CCGTGAGGTGTTC | 292 |
| CATGAGGTGATC | 293 |
| ATGGAGGTATTC | 294 |
| GTTTGAGGTGATC | 295 |
| AAATGAGGTAATC | 296 |
| ACTTGAGGTAATC | 297 |
| GAGGAGGTGTTC | 298 |
| AAGGAGGTGATC | 299 |
| GTGGAGGTGATC | 300 |
| GCATGAGGTGTTC | 301 |
| ATTGGAGGTGATC | 302 |
| TAGGGAGGTATTC | 303 |
| ATTTGAGGTAATC | 304 |
| AATGAGGTGATC | 305 |
| GATGAGGTAATC | 306 |
| GTATGAGGTATTC | 307 |
| CGTTGAGGTGTTC | 308 |
| CCAGGAGGTAATC | 309 |
| CTGGGAGGTGATC | 310 |
| GTGTGAGGTATTC | 311 |
| AAGGAGGTATTC | 312 |
| AAGGGAGGTATTC | 313 |
| GGGGGAGGTGTTC | 314 |
| CAGTGAGGTAATC | 315 |
| CGATGAGGTGTTC | 316 |
| TAAGGAGGTAATC | 317 |
| TGGGGAGGTGATC | 318 |
| ACTTGAGGTGATC | 319 |
| TAGGGAGGTGATC | 320 |
| ACATGAGGTAATC | 321 |
| TCGGGAGGTATTC | 322 |
| AAGGGAGGTAATC | 323 |
| AATGGAGGTATTC | 324 |
| CGGTGAGGTGATC | 325 |
| GCTTGAGGTGTTC | 326 |
| CAGTGAGGTGTTC | 327 |
| GTATGAGGTGTTC | 328 |

TABLE 1-continued

| Oligonucleotide Probe 3' regions (Prokaryotic 16S Sequences (5' → 3')) | SEQ ID NO |
|---|---|
| CTTGAGGTAATC | 329 |
| TGGGGAGGTATTC | 330 |
| GATGAGGTATTC | 331 |
| CGGGGAGGTGATC | 332 |
| GAATGAGGTATTC | 333 |
| CATGAGGTAATC | 334 |
| GGTGAGGTAATC | 335 |
| TGAGGAGGTAATC | 336 |
| GCTTGAGGTAATC | 337 |
| CTGTGAGGTGTTC | 338 |
| TCATGAGGTGATC | 339 |
| CGGGAGGTATTC | 340 |
| CGTTGAGGTGATC | 341 |
| AGTGAGGTATTC | 342 |
| CGGGAGGTAATC | 343 |
| TCATGAGGTGTTC | 344 |
| CAAGGAGGTGTTC | 345 |
| CCATGAGGTAATC | 346 |
| GCATGAGGTGATC | 348 |
| AAATGAGGTGATC | 349 |
| CAGTGAGGTGATC | 350 |
| AGAGGAGGTGTTC | 351 |
| CAATGAGGTGATC | 352 |
| TAGTGAGGTATTC | 353 |
| CTTGGAGGTATTC | 354 |
| CCGTGAGGTATTC | 355 |
| TATGAGGTATTC | 356 |
| GAGGGAGGTATTC | 357 |
| GGAGGAGGTAATC | 358 |
| CTGGAGGTGTTC | 359 |
| ACTGGAGGTAATC | 360 |
| GAAGGAGGTGATC | 361 |
| GGGTGAGGTGATC | 362 |
| TTATGAGGTATTC | 363 |
| ACAGGAGGTGATC | 364 |
| TATGGAGGTGATC | 365 |
| ATTGGAGGTATTC | 366 |

TABLE 1-continued

| Oligonucleotide Probe 3' regions (Prokaryotic 16S Sequences (5' → 3')) | SEQ ID NO |
|---|---|
| GTGGAGGTGTTC | 367 |
| ATGTGAGGTATTC | 368 |
| TTAGGAGGTGATC | 369 |
| ATTGAGGTGTTC | 370 |
| GGTGAGGTATTC | 371 |
| GCGTGAGGTATTC | 372 |
| GAAGGAGGTATTC | 373 |
| ACATGAGGTGTTC | 374 |
| GCGTGAGGTGATC | 375 |
| GAGGAGGTAATC | 376 |
| TGTGAGGTGTTC | 377 |
| GTAGGAGGTAATC | 378 |
| TGTGGAGGTAATC | 379 |
| TGATGAGGTGATC | 380 |
| GGATGAGGTAATC | 381 |
| CCATGAGGTGATC | 382 |
| CATGAGGTGTTC | 383 |
| CCGTGAGGTGATC | 384 |
| AGAGGAGGTATTC | 385 |
| TTATGAGGTAATC | 386 |
| AGTTGAGGTGATC | 387 |
| CTTGGAGGTGTTC | 388 |
| TGAGGAGGTGTTC | 389 |
| GAGGGAGGTGTTC | 390 |
| GTTTGAGGTGTTC | 391 |
| CAGGGAGGTGTTC | 392 |
| CGAGGAGGTGATC | 393 |
| GCGTGAGGTGTTC | 394 |
| TAGGAGGTATTC | 395 |
| TAGGAGGTGTTC | 396 |
| CCGTGAGGTAATC | 397 |
| ATAGGAGGTGATC | 398 |
| GTTGGAGGTGATC | 399 |
| CAGGGAGGTGATC | 400 |
| CCAGGAGGTATTC | 401 |
| CGTGAGGTGATC | 402 |
| ATTTGAGGTGATC | 403 |
| AGGGGAGGTGTTC | 404 |

TABLE 1-continued

| Oligonucleotide Probe 3' regions (Prokaryotic 16S Sequences (5' → 3')) | SEQ ID NO |
|---|---|
| TCGTGAGGTAATC | 405 |
| GTTTGAGGTAATC | 406 |
| TGGGAGGTGTTC | 407 |
| TTGGAGGTGATC | 408 |
| GAATGAGGTGATC | 409 |
| CCTGGAGGTGATC | 410 |
| TTGTGAGGTATTC | 411 |
| TTTTGAGGTGTTC | 412 |
| GAATGAGGTGTTC | 413 |
| CTTTGAGGTGTTC | 414 |
| CCAGGAGGTGTTC | 415 |
| GGAGGAGGTGTTC | 416 |
| AGGTGAGGTATTC | 417 |
| CTAGGAGGTATTC | 418 |
| TTTGAGGTATTC | 419 |
| CCAGGAGGTGATC | 420 |
| AATGGAGGTGATC | 421 |
| GCGGGAGGTAATC | 422 |
| GTGGGAGGTAATC | 423 |
| TTGGGAGGTGATC | 424 |
| GAGTGAGGTAATC | 425 |
| CATTGAGGTAATC | 426 |
| ATTGAGGTAATC | 427 |
| AAAGGAGGTAATC | 428 |
| CGAGGAGGTATTC | 429 |
| CTTTGAGGTGATC | 430 |
| TGTTGAGGTGTTC | 431 |
| TCTTGAGGTGATC | 432 |
| TTTTGAGGTATTC | 433 |
| GTTGAGGTGTTC | 434 |
| AAGTGAGGTGATC | 435 |
| CCGGGAGGTGATC | 436 |
| TATGAGGTGATC | 437 |
| CATGGAGGTAATC | 438 |
| GCTGGAGGTATTC | 439 |
| ATGTGAGGTAATC | 440 |
| TGATGAGGTAATC | 441 |

TABLE 1-continued

| Oligonucleotide Probe 3' regions (Prokaryotic 16S Sequences (5' → 3')) | SEQ ID NO |
|---|---|
| ATGGGAGGTGATC | 442 |
| AATGAGGTATTC | 443 |
| TAGTGAGGTGTTC | 444 |
| GTGTGAGGTAATC | 445 |
| ATGTGAGGTGTTC | 446 |
| CTGGAGGTGATC | 447 |
| CCTTGAGGTGATC | 448 |
| GAGTGAGGTATTC | 449 |
| AGTTGAGGTAATC | 450 |
| GCAGGAGGTATTC | 451 |
| TAATGAGGTATTC | 452 |
| CAAGGAGGTAATC | 453 |
| TGGTGAGGTGTTC | 454 |
| TGGTGAGGTGATC | 455 |
| CATTGAGGTGATC | 456 |
| GATTGAGGTGTTC | 457 |
| ATTGAGGTGATC | 458 |
| GCGGGAGGTGTTC | 459 |
| TTGGGAGGTGTTC | 460 |
| ATATGAGGTGTTC | 461 |
| ACGTGAGGTGTTC | 462 |
| CCTTGAGGTGTTC | 463 |
| GCGGGAGGTGATC | 464 |
| ACAGGAGGTGTTC | 465 |
| ATGGAGGTGATC | 466 |
| CTGTGAGGTATTC | 467 |
| TTTTGAGGTGATC | 468 |
| ATTGGAGGTAATC | 469 |
| GGGTGAGGTGTTC | 470 |
| TGGTGAGGTAATC | 471 |
| TGTGAGGTAATC | 472 |
| AATTGAGGTGATC | 473 |
| AGTTGAGGTATTC | 474 |
| GCAGGAGGTAATC | 475 |
| AGATGAGGTATTC | 476 |
| GGTGGAGGTGATC | 477 |
| TAAGGAGGTGATC | 478 |
| TCGGGAGGTGATC | 479 |

TABLE 1-continued

| Oligonucleotide Probe 3' regions (Prokaryotic 16S Sequences (5' → 3')) | SEQ ID NO |
|---|---|
| TCGGGAGGTGTTC | 480 |
| GAGTGAGGTGTTC | 481 |
| AAGTGAGGTAATC | 482 |
| GGGGAGGTAATC | 483 |

In some embodiments, the 3' region of the oligonucleotide probe is designed to hybridize to a bacterial rRNA (e.g., a bacterial 16S rRNA, 23S rRNA, or 5S rRNA) of a gram positive bacteria, a gram negative bacteria, or a miscellaneous (neither gram positive or negative) bacteria, or a particular strain thereof. In certain aspects, the bacteria is a gram positive bacteria or strain thereof selected from Micrococcaceae (e.g., *Micrococcus, Planococcus, Staphylococcus, Stomatococcus*), Streptococcaceae (e.g., *Streptococcus, Enterococcus*), *Bacillus, Clostridium*, Lactobacillaceae (e.g., *Lactobacillus*), Actinomycetaceae (e.g., *Actinomyces, Bifidobacterium*), Nocardiaceae (e.g., *Nocordia, Rhodococcus*), Mycobacteriaceae (e.g., *Mycobacterium*), *Aerococcus, Coprococcus, Gemello, Lactococcus, Leuconostoc, Pediococcus, Peptostreptococcus, Sarcina, Arcanobacterium, Corynebacterium, Erysipelothrix, Eubacterium, Gordnerella, Listeria, Propioniboderium*, and when an oligonucleotide probe library is employed, any combination thereof. In certain aspects, the bacteria is a gram negative bacteria or strain thereof selected from Neisseriaceae (e.g., *Neisseria*), Moraxellaceae (e.g., *Acinetobacter, Branhamella, Moraxella*), Anaerobes (e.g., Acinominococcus (e.g., *Megasphaera, Veillonella*)), Enterobacterioceae (e.g., *Citrobacter, Edwardsiella, Enterobacter, Escherichia, Klebsiella, Morganella, Proteus, Providencia, Salmonella, Serratia, Shigella, Yersinia*), Vibrianaceae (e.g., *Aeromonas, Plesiomonas, Vibrio*), Spirillaceae (e.g., *Campylobocter, Helicobacter*), Pseudomonadaceae (e.g., *Pseudomonas, Xanthomonas*), Pasteurellaceae (e.g., *Actinobacillus, Haemophilus, Pasteurella*), *Afipia, Bordatella, Bortonella, Brucella, Cardiobacterium, Colymmatobacterium, Eikenella, Flavobacterium, Francisella, Kingello, Spirillum, Streptobacillus*, Legionellaceae (e.g., *Fluoribacter, Legionella, Tatlockia*), Bacteroidoceae (e.g., *Bacteroides, Bilophora, Fusobacterium, Leptotrichia, Porphyromonas, Prevotello, Wolinella*), and when an oligonucleotide probe library is employed, any combination thereof. In certain aspects, the bacteria is a miscellaneous bacteria or strain thereof selected from Spirochaetales (*Treponema, Borrelia, Leptospira*), Chlamydiaceae (e.g., *Chlamydia*), Mycoplasmataceae (e.g., *Mycoplasma, Ureaplasma*), Rickettsiaceae (e.g., *Rickettsia, Coxiella, Rochalimaea, Ehrlichia*), and when an oligonucleotide probe library is employed, any combination thereof. In certain aspects, an oligonucleotide probe library is employed such that the sample may be interrogated for the presence of any of the gram positive, gram negative, and/or miscellaneous bacteria types set forth above.

In certain aspects, the 3' region of the oligonucleotide probe is designed to hybridize to a archaeal rRNA. Archaeal ribosomes have a size and composition similar to those of their bacterial counterparts: they contain three ribonucleic acid (RNA) molecules, 16S, 23S and 5S RNA and 50-70 proteins depending on the species. The 3' region may be designed to hybridize to an rRNA of an archaea selected from crenarchaeota, euryarchaeota, korarchaeota, methanogens (e.g., *Methanobacterium bryantii, Methanobacterium formicum, Methanobrevibacter arboriphilicus, Methanobrevibacter gottschalkii, Methanobrevibacter ruminantium, Methanobrevibacter smithii, Methanococcus chunghsingensis*, and the like), halophiles, thermophiles, psychrophiles, and the like. In some embodiments, the 3' region of the oligonucleotide probe is designed to hybridize to an archaeal 16S rRNA.

As used herein, an "oligonucleotide" is a single-stranded multimer of nucleotides from 5 to 500 nucleotides, e.g., 5 to 100 nucleotides. Oligonucleotides may be synthetic or may be made enzymatically, and, in some embodiments, are 5 to 50 nucleotides in length. Oligonucleotides may contain ribonucleotide monomers (i.e., may be oligoribonucleotides or "RNA oligonucleotides"), deoxyribonucleotide monomers (i.e., may be oligodeoxyribonucleotides or "DNA oligonucleotides"), or a combination thereof. Oligonucleotides may be 10 to 20, 20 to 30, 30 to 40, 40 to 50, 50 to 60, 60 to 70, 70 to 80, 80 to 100, 100 to 150 or 150 to 200, or up to 500 nucleotides in length, for example.

The 3' region of the oligonucleotide probe that is complementary and hybridizes to the target rRNA, and the 5' region of the oligonucleotide probe that is complementary and hybridizes to the probe complement oligonucleotide, may be any suitable length. In some embodiments, the 3' region of the oligonucleotide probe that hybridizes to the target rRNA and the 5' region of the oligonucleotide probe that hybridizes to the probe complement oligonucleotide have a length independently selected from 4, 5, 6, 7, 8, 9, 10, 11, 12, 13, 14, 15, 16, 17, 18, 19, 20, 21, 22, 23, 24, 25, 26, 27, 28, 29, or 30 nucleotides. In certain aspects, the 3' region of the oligonucleotide probe that hybridizes to the target rRNA is from 4 to 20 nucleotides in length, such as from 5 to 15 nucleotides in length, e.g., 5 to 10 nucleotides in length.

The terms "complementary" or "complementarity" as used herein refer to a nucleotide sequence that base-pairs by non-covalent bonds to a region of a target nucleic acid, e.g., the nucleotide sequence of the 3' region of the oligonucleotide probe that hybridizes to the target rRNA and the nucleotide sequence of the 5' region of the oligonucleotide probe that hybridizes to the probe complement oligonucleotide. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" or "complementarity" refers to a nucleotide sequence that is at least partially complementary. These terms may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, the 3' region of the oligonucleotide probe may be perfectly (i.e., 100%) complementary to the target rRNA, or the 3' region of the oligonucleotide probe may share some degree of complementarity which is less than perfect (e.g., 70%, 75%, 85%, 90%, 95%, 99%). The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions×100). When a position in one sequence is occupied by the same nucleotide as the corresponding position in the other sequence, then the molecules are identical at that position. A non-limiting example of such a mathematical algorithm is described in Karlin et al., *Proc. Natl. Acad. Sci. USA* 90:5873-5877 (1993). Such an algorithm is incorporated into the NBLAST and XBLAST programs (version 2.0) as described in Altschul et al., *Nucleic Acids Res.* 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

As summarized above, the sample including rRNA, the probe complement oligonucleotide and the oligonucleotide probe are combined under conditions in which the 3' region of the oligonucleotide probe hybridizes to the 3' region of the rRNA and the 5' region of the oligonucleotide probe hybridizes to the probe complement oligonucleotide. Whether specific hybridization occurs is determined by such factors as the degree of complementarity between the relevant (that is, hybridizing) regions of the oligonucleotide probe, the target rRNA, and the probe complement oligonucleotide, as well as the length thereof, salt concentration, and the temperature at which the hybridization occurs, which may be informed by the melting temperatures ($T_M$) of the relevant regions. The melting temperature refers to the temperature at which half of the relevant regions remain hybridized and half of the relevant regions dissociate into single strands. The Tm of a duplex may be experimentally determined or predicted using the following formula $Tm=81.5+16.6(\log 10[Na^+])+0.41$ (fraction G+C)−(60/N), where N is the chain length and $[Na^+]$ is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict Tm of complementarity region/overhang duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

In some embodiments, the oligonucleotide probe, the probe complement oligonucleotide, or both, includes one or more non-natural nucleotides (which may also be referred to as nucleotide analogs). Non-limiting examples of non-natural nucleotides that may be included in the oligonucleotide probe and/or probe complement oligonucleotide are LNA (locked nucleic acid), PNA (peptide nucleic acid), FANA (2'-deoxy-2'-fluoroarabinonucleotide), GNA (glycol nucleic acid), TNA (threose nucleic acid), 2'-O-Me RNA, 2'-fluoro RNA, Morpholino nucleotides, and any combination thereof. In certain aspects, the 3' region of the oligonucleotide probe includes one or more such non-natural nucleotides, for example, to increase the melting temperature of the hybridization region between the oligonucleotide probe and the target rRNA. Similarly, the 5' region of the oligonucleotide probe, the probe complement oligonucleotide, or both, may include one or more such non-natural nucleotides, for example, to increase the melting temperature of the hybridization region between the oligonucleotide probe and the probe complement oligonucleotide.

In certain aspects, the oligonucleotide probe, the probe complement oligonucleotide, or both, includes one or more labels. Labels of interest include, e.g., detectable labels. As used herein, a "detectable label" is a chemical moiety that affords detectability to a species (e.g., oligonucleotide) attached thereto. Exemplary detectable labels include fluorescent labels, luminescent labels, radioactive labels, spectroscopic labels, stable isotope mass tagged labels, electron spin resonance labels, nuclear magnetic resonance labels, chelated metal labels, and the like.

In some embodiments, the oligonucleotide probe, the probe complement oligonucleotide, or both, includes one or more affinity tags. The term "affinity tag," as used herein, refers to a chemical moiety that functions as, or contains, an affinity ligand that is capable of binding (e.g., non-covalently or covalently) to a second, "capture" chemical moiety, such that the nucleic acid complex or derivative thereof can be selected (or "captured") from a mixture using the capture moiety. In some embodiments, the capture moiety is bound to a solid support, e.g., a bead (e.g., a magnetic bead), planar surface, or the like. Non-limiting examples of affinity tags that may be included in the oligonucleotide probe, the probe complement oligonucleotide, or both, include biotin, avidin, streptavidin, an aptamer (see, e.g., Wilson & Szostak (1999) *Annu Rev Biochem.* 68:611-647), an MS2 coat protein-interacting sequence, a WA protein-interacting sequence, etc. Nucleic acid affinity tags that find use in the oligonucleotides and methods of the present disclosure are described, e.g., in Walker et al. (2008) *Methods Mol Biol.* 488:23-40. Interactions between the affinity tag and the capture moiety may be specific and reversible (e.g., non-covalent binding or hydrolyzable covalent linkage), but if desired, may be (or subsequently may be made) irreversible, e.g., a non-hydrolyzable covalent linkage between the affinity tag and the capture moiety.

In certain aspects, the 3' region of the probe oligonucleotide and the 5' region of the probe oligonucleotide are contiguous. In other aspects, the 3' region of the probe oligonucleotide and the 5' region of the probe oligonucleotide are separated by one or more nucleotides. In some embodiments, the 3' region of the probe oligonucleotide that hybridizes to the target rRNA includes the 3' end of the probe oligonucleotide. According to certain embodiments, the 3' region of the probe oligonucleotide that hybridizes to the target rRNA does not include the 3' end of the probe oligonucleotide. In some embodiments, the 5' region of the probe oligonucleotide that hybridizes to the probe complement oligonucleotide includes the 5' end of the probe oligonucleotide. According to certain embodiments, the 5' region of the probe oligonucleotide that hybridizes to the probe complement oligonucleotide does not include the 5' end of the probe oligonucleotide.

In certain aspects, upon formation of the nucleic acid complex, the methods of the present disclosure further include producing a derivative of the nucleic acid complex. In some embodiments, producing a derivative of the nucleic acid complex includes covalently linking the 3' end of the rRNA to the 5' end of the probe complement oligonucleotide. Such linking of the 3' end of the rRNA to the 5' end of the probe complement oligonucleotide may enable or facilitate a downstream application of interest, such as but not limited to, sequencing all or a portion of the resulting rRNA-probe complement oligonucleotide hybrid strand in a next-generation sequencing system (e.g., via a nanopore of a nanopore-based sequencing system). A variety of suitable approaches are available for covalently linking the 3' end of the rRNA to the 5' end of the probe complement oligonucleotide. In some embodiments, the linking is carried out using a chemical linking approach. In other aspects, the linking is carried out using an enzymatic approach, such as enzymatically ligating the 3' end of the rRNA to the 5' end of the probe complement oligonucleotide. Suitable reagents (e.g., ligases) and kits for performing such ligation reactions are known and available, e.g., the Instant Sticky-end Ligase Master Mix available from New England Biolabs (Ipswich, Mass.). Ligases that may be employed include, e.g., T4 DNA ligase (e.g., at low or high concentration), T4 DNA ligase, T7 DNA Ligase, *E. coli* DNA Ligase, Electro Ligase®, or the like. Conditions suitable for performing the ligation reaction will vary depending upon the type of ligase used. Information regarding such conditions is readily available.

In some embodiments, producing a derivative of the nucleic acid complex includes amplifying all or a portion of the nucleic acid complex, e.g., by polymerase chain reaction (PCR). Such amplification may be carried out using amplification primers that specifically hybridize to desired regions of the nucleic acid complex under amplification conditions.

In certain aspects, producing a derivative of the nucleic acid complex includes producing a cDNA from the nucleic acid complex. Producing a cDNA may include reverse transcribing all or a portion of the rRNA of the complex. According to some embodiments, reverse transcribing all or a portion of the rRNA is accomplished using the oligonucleotide probe as the primer and a suitable polymerase (e.g., reverse transcriptase) to carry out a first-strand synthesis reaction. Reagents and kits for carrying out such reverse transcription are readily available and include, e.g., the SuperScript IV First-Strand Synthesis System available from ThermoFisher Scientific. In certain aspects, when the methods include reverse transcribing all or a portion of the rRNA of the complex, the 3' end of the nascent cDNA strand and the 5' end of the rRNA are covalently linked. In some embodiments, the 3' end of the nascent cDNA strand and the 5' end of the rRNA are covalently linked via a hairpin adapter. Such an adapter finds use, e.g., for “2D” sequencing of the resulting hybrid rRNA-cDNA strand (or, e.g., an amplicon thereof) by nanopore-based sequencing. By “2D” sequencing in this context is meant both the rRNA and cDNA strand are sequenced as the hybrid rRNA-cDNA strand translocates through the nanopore. A consensus sequence may be obtained from the sequence obtained from the rRNA portion of the hybrid strand and the sequence obtained from the cDNA portion of the hybrid strand, which consensus sequence may be more accurate than the rRNA- and cDNA-derived sequences individually.

In some embodiments, the nucleic acid complex, or any of the derivatives described herein in any desired combination, is sequenced. The sequencing may be carried out on any suitable sequencing platform, including a Sanger sequencing platform, a high-throughput sequencing (HTS) (or “next-generation sequencing (NGS)”) platform, or the like. HTS/NGS sequencing platforms of interest include, but are not limited to, a sequencing platform provided by Illumina® (e.g., the HiSeg™, MiSeg™ and/or Genome Analyzer™ sequencing systems); Oxford Nanopore™ Technologies (e.g., a MinION™, GridION×5™, PromethION™, or SmidgION™ nanopore-based sequencing system), Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest. Detailed protocols for direct sequencing (e.g., by nanopore-based sequencing) or preparing compatible nucleic acid molecules for sequencing on a particular platform (e.g., by amplification, e.g., solid-phase amplification, or the like), sequencing the compatible molecules, and analyzing the sequencing data are available from the manufacturer of the sequencing platform of interest.

In certain aspects, when it is desirable to sequence nucleic acid complexes (or derivatives thereof) produced using the methods of the present disclosure, the oligonucleotide probe, the probe complement oligonucleotide, or both, may include one or more sequencing adapters or sub-regions thereof. By “sequencing adapter” is meant one or more nucleic acid domains that include at least a portion of a nucleic acid sequence (or complement thereof) utilized by a sequencing platform of interest, such as a sequencing platform provided by Illumina® (e.g., the HiSeg™, MiSeg™ and/or Genome Analyzer™ sequencing systems); Oxford Nanopore™ Technologies (e.g., the MinION™ sequencing system), Ion Torrent™ (e.g., the Ion PGM™ and/or Ion Proton™ sequencing systems); Pacific Biosciences (e.g., the PACBIO RS II sequencing system); Life Technologies™ (e.g., a SOLiD™ sequencing system); Roche (e.g., the 454 GS FLX+ and/or GS Junior sequencing systems); or any other sequencing platform of interest.

In certain aspects, the sequencing adapter is, or includes, a nucleic acid domain selected from: a domain (e.g., a “capture site” or “capture sequence”) that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind); a unique identifier (e.g., a barcode or other domain that uniquely identifies the 3' region of the oligonucleotide probe, the probe complement oligonucleotide, or both, and/or uniquely identifies the sample source of the rRNA being sequenced to enable sample multiplexing by marking every molecule from a given sample with a specific barcode or “tag”); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest, e.g., to determine expression levels based on the number of instances a unique tag is sequenced; a complement of any such domains; or any combination thereof. In certain aspects, a barcode domain (e.g., sample index tag) and a molecular identification domain (e.g., a molecular index tag) may be included in the same nucleic acid.

When the oligonucleotide probe, the probe complement oligonucleotide, or both, include a portion of a sequencing adapter, one or more additional sequencing adapters and/or a remaining portion of the sequencing adapter may be added using a variety of approaches. For example, additional and/or remaining portions of sequencing adapters may be added by ligation, reverse transcription, PCR amplification, and/or the like. In the case of PCR, an amplification primer pair may be employed that includes a first amplification primer that includes a 3' hybridization region (e.g., for hybridizing to an oligonucleotide or rRNA of the nucleic acid complex) and a 5' region including an additional and/or remaining portion of a sequencing adapter, and a second amplification primer that includes a 3' hybridization region (e.g., for hybridizing to an oligonucleotide or rRNA of the nucleic acid complex at or near the end of the complex opposite the end to which the first amplification primer hybridizes) and optionally a 5' region including an additional and/or remaining portion of a sequencing adapter.

In certain aspects, provided is a method that includes producing a nucleic acid complex that includes the oligonucleotide probe hybridized to a target rRNA (e.g., a 16S rRNA of a bacteria or archaea of interest) and probe complement oligonucleotide as described above, and covalently linking the 3' end of the rRNA to the 5' end of the probe complement oligonucleotide. The resulting derivative is then sequenced using a nanopore-based sequencing system. The sequencing may include delivering the derivative to a nanopore (or an enzyme (e.g., a polymerase) located at or near the nanopore), and directly sequencing all or a portion of the hybrid rRNA-probe complement oligonucleotide strand by translocating it through the nanopore (unzipping the oligonucleotide probe in the process) and collecting signals (e.g., relating to current changes through the nanopore) during the translocation, which signals are indicative of the nucleotide sequence of the hybrid strand. In some embodiments, subsequent to producing the nucleic acid complex, the rRNA is reverse transcribed using the oligonucleotide probe as the primer. In certain aspects, the 3' end of the resulting nascent cDNA is linked to the 5' end of the rRNA using a hairpin adapter. The resulting derivative is then delivered to the nanopore (or an enzyme (e.g., a polymerase) located at or near the nanopore), and all or a portion of the resulting hybrid cDNA-rRNA-probe complement oligonucleotide strand is sequenced by translocating the hybrid strand through the nanopore as described above. According to this embodiment, the hairpin adapter enables "2D" sequencing of the derivative as described elsewhere herein. As will be appreciated in view of the present disclosure, the above described embodiments may be carried out using an oligonucleotide probe library, where the library includes unique oligonucleotide probes that differ from one another with respect to the nucleotide sequence of the 3' region, the nucleotide sequence of the 5' region, or both. For example, the unique oligonucleotide probes may differ from one another at least with respect to the nucleotide sequence of their 3' regions, which different 3' regions are designed to hybridize to distinct rRNAs, e.g., distinct 16S rRNAs from various bacteria and/or archaea, and/or strains of interest thereof. In this way, the sample may be interrogated for the presence of rRNAs from multiple different sources (e.g., multiple different bacteria and/or archaea). In any of the embodiments described herein, the results may be qualitative and/or quantitative. Quantitative results may be achieved, e.g., based on the number of sequencing reads obtained from complexes having a particular oligonucleotide probe.

Details regarding nanopore-based sequencing are described, e.g., in Feng et al. (2015) *Genomics, Proteomics & Bioinformatics* 13(1):4-16. Any of the nanopore-based sequencing embodiments described herein may be carried out using, e.g., a MinION™' GridION×5™, PromethION™, or SmidgION™ nanopore-based sequencing system, available from Oxford Nanopore Technologies. Detailed design considerations and protocols for carrying out the sequencing are provided with such systems.

Oligonucleotide Probes, Libraries Thereof, and Compositions

Also provided are oligonucleotide probes, libraries thereof, and compositions including same. The oligonucleotide probes, oligonucleotide probe libraries, and compositions find use, e.g., in practicing the methods of the present disclosure, and may include any of the oligonucleotide probes, oligonucleotide probe libraries, probe complement oligonucleotides, etc. having any of the features described hereinabove in the section describing the methods of the present disclosure, in any desired combination.

In some embodiments, a composition of the present disclosure includes any component (e.g., any of the oligonucleotide probes, oligonucleotide probe libraries, probe complement oligonucleotides, samples, etc.) having any of the features described hereinabove in the section describing the methods of the present disclosure, in any desired combination.

The compositions of the present disclosure may include the one or more components present in a container. Suitable containers include, but are not limited to, tubes, vials, and plates (e.g., a 96- or other-well plate).

In certain aspects, the compositions include the one or more components in a liquid medium. The liquid medium may be an aqueous liquid medium, such as water, a buffered solution, and the like. One or more additives such as a salt (e.g., NaCl, MgCl2, KCl, MgSO4), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a solubilizing agent, a detergent (e.g., a non-ionic detergent such as Tween-20, etc.), a nuclease inhibitor, glycerol, a chelating agent, and the like may be present in such compositions.

In some embodiments, a composition of the present disclosure is a lyophilized composition. A lyoprotectant may be included in such compositions in order to protect the oligonucleotide probes, oligonucleotide probe libraries, and/or probe complement oligonucleotides against destabilizing conditions during a lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM. In certain aspects, a composition of the present disclosure is in a liquid form reconstituted from a lyophilized form. An example procedure for reconstituting a lyophilized composition is to add back a volume of pure water (typically equivalent to the volume removed during lyophilization); however solutions including buffering agents, antibacterial agents, and/or the like, may be used for reconstitution.

In certain aspects, provided are compositions that include complexes including oligonucleotide probes and probe complement oligonucleotides present as hybridized complexes.

Kits

As summarized above, the present disclosure provides kits. The kits may include, e.g., any of the oligonucleotide probes, oligonucleotide probe libraries, probe complement oligonucleotides, compositions, etc. having any of the features described hereinabove, in any desired combination. Kits of the present disclosure may further include any reagents, buffers, etc. useful for carrying out embodiments of the methods of the present disclosure.

According to some embodiments, a subject kit includes a ligase or chemical linking agent, e.g., when it is desirable to covalently link components of the nucleic acid complex, e.g., the 3' end of the rRNA and the 5' end of a probe complement oligonucleotide. In certain aspects, a subject kit includes reagents useful for reverse transcribing all or a portion of the rRNA of the nucleic acid complex. For example, a kit of the present disclosure may include a reverse transcriptase, compatible buffers, dNTPs, and/or the like. In some embodiments, when it is desirable to link the 3' end of a nascent cDNA to the 5' rRNA of the corresponding template rRNA, the kit may include reagents useful for carrying out such linking. For example, the kit may include a hairpin adapter for linking the 3' end of a nascent cDNA to the 5' rRNA of the corresponding template rRNA, e.g., to facilitate “2D” sequencing of the cDNA and rRNA using a nanopore-based sequencing system as described elsewhere herein. The subject kits may include components that find use in purifying nucleic acid complexes or components thereof. For example, the kits may include beads or other forms of solid support having thereon a capture agent for capturing nucleic acid complexes or components thereof having a corresponding affinity tag as described elsewhere herein.

Components of the kits may be present in separate containers, or multiple components may be present in a single container. A suitable container includes a single tube (e.g., vial), one or more wells of a plate (e.g., a 96-well plate, a 384-well plate, etc.), or the like.

The kits may include instructions, e.g., for using the for using the oligonucleotide probe, the oligonucleotide probe library, or the composition to produce a nucleic acid complex comprising the oligonucleotide probe, an rRNA, and a probe complement oligonucleotide. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

Utility

The methods, compositions and kits of the present invention find use in a variety of contexts, including research, clinical, environmental, and other contexts.

In some embodiments, the methods of the present disclosure find use in preparing nucleic acid sequencing libraries. For example, the methods find use in producing nucleic acid complexes or derivatives thereof useful for downstream sequencing. In some embodiments, the methods enable direct sequencing of all or a portion of a target rRNA captured by a corresponding oligonucleotide probe, e.g., using a nanopore-based sequencing system. In certain aspects, the sequencing libraries include a plurality of unique nucleic acid complexes, in which the unique complexes are representative of different types rRNAs present in the sample of interest.

In certain aspects, the methods find use in determining the presence, amount, or both, of one or more organisms (e.g., eukaryotic organisms, prokaryotic organisms, strains thereof, etc.) in a sample of interest. For example, the methods of the present disclosure may be used to interrogate a sample of interest for the presence of an rRNA of interest (e.g., by downstream next-generation sequencing, real-time polymerase chain reaction, or the like), e.g., an rRNA from a particular organism or strain thereof to determine whether the organism is present in the sample, and if desired, quantitate the level of the organism in the sample based on the level of the corresponding rRNA in the sample. In certain aspects, an oligonucleotide probe library is employed such that a sample of interest may be interrogated for the presence of multiple distinct rRNAs of interest. In some embodiments, the multiple distinct rRNAs of interest correspond to multiple distinct organisms (e.g., eukaryotic, prokaryotic (e.g., bacteria and/or archaea), and/or the like), such that the methods enable interrogation of the sample for the presence (and optionally, amount) of such multiple distinct organisms.

The methods find use, e.g., in any context in which it is desirable to determine the presence and/or amount of one or more organisms in a sample. As just one example in the clinical context, interrogating a medical sample for the presence and/or amount of one or more organisms finds use in determining whether an individual has an infection and, if so, identifying the underlying infectious agent(s), e.g., bacteria, fungi, parasites, and/or the like. As just one example in the environmental context, interrogating an environmental sample (e.g., drinking water, food (e.g., produce), etc.) for the presence and/or amount of one or more organisms finds use in determining whether the source of the sample is contaminated and, if so, identifying the underlying contaminants, e.g., bacteria, fungi, parasites, and/or the like.

The following examples are offered by way of illustration and not by way of limitation.

EXPERIMENTAL

Example 1—Reverse Transcription of Nucleic Acid Complexes

In this example, nucleic acid complexes were produced according to the methods of the present disclosure. In this particular example, an oligonucleotide probe having a 3' region complementary to the anti-Shine-Dalgarno sequence of the 16S *E. coli* rRNA was combined with the 16S *E. coli* rRNA and a probe complement oligonucleotide complementary to a 5' region of the oligonucleotide probe. The components were combined under hybridization conditions to produce a nucleic acid complex as shown, e.g., in FIG. 1.

Figure 2:
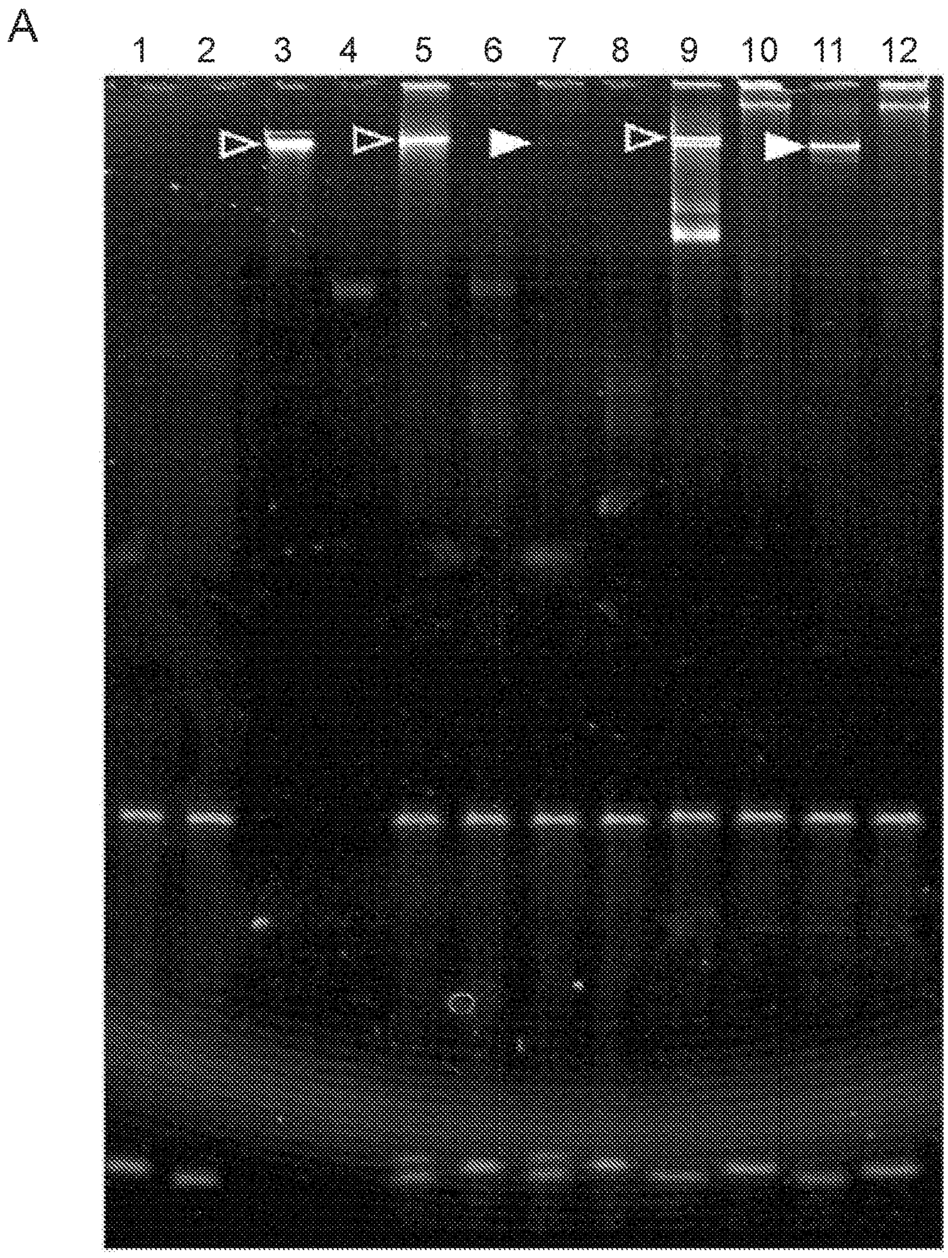
FIG. 2, panels A and B, show gel analysis of: a reverse transcription reaction demonstrating cDNA synthesis from the oligonucleotide probe 3' terminus (panel A); and a ligation reaction demonstrating the oligonucleotide probe strand facilitates probe complement oligonucleotide ligation to the rRNA 3' end (panel B).
Figure 2:
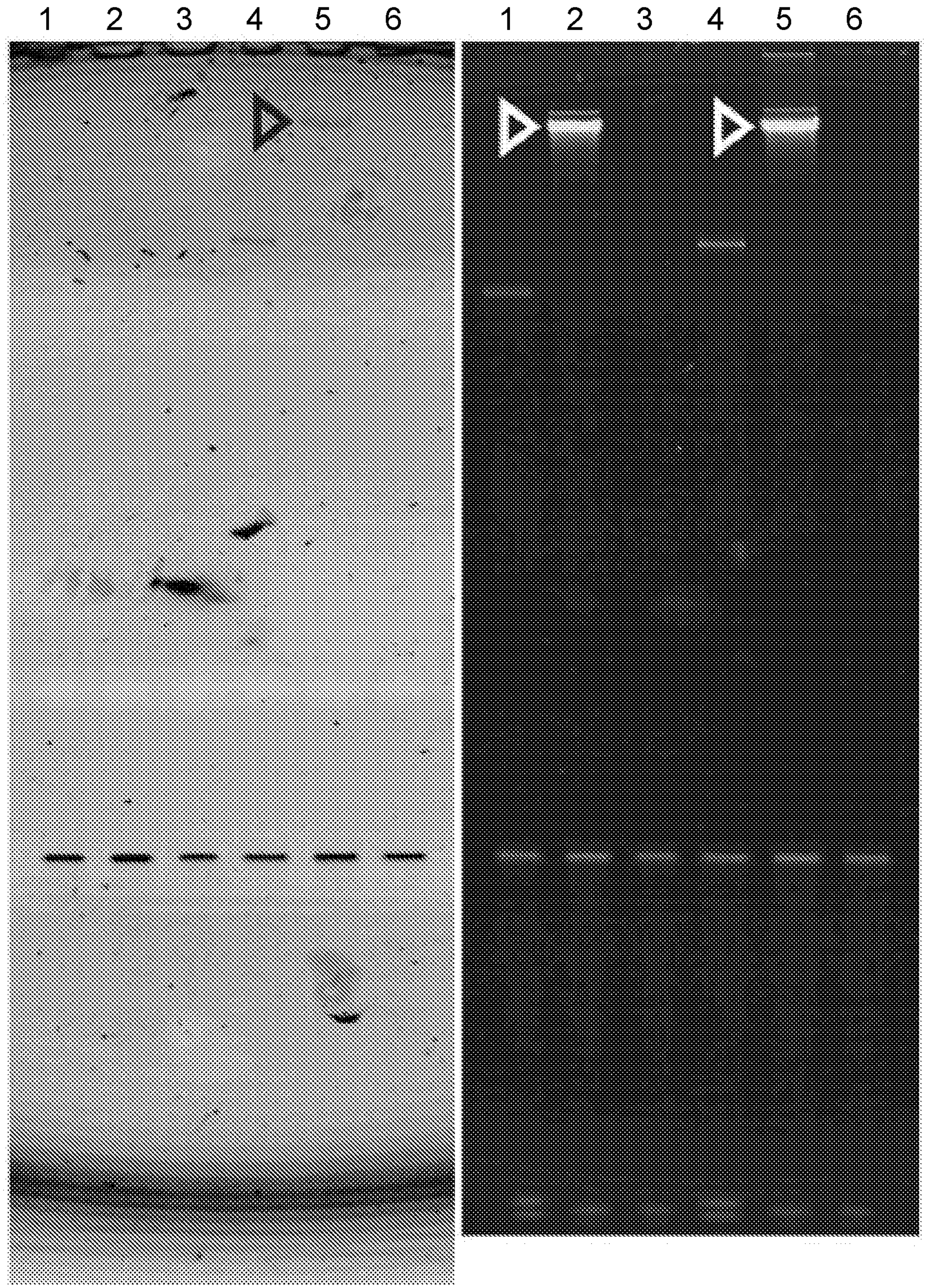

Subsequent to complex formation, reverse transcription was carried out using the oligonucleotide probe as the primer. Gel analysis demonstrating cDNA synthesis from the 3' end of the oligonucleotide probe is shown in FIG. 2, panel A. Lanes 1 and 2, probe (upper band) and probe complement (lower band) for *E. coli* 16S rRNA and control polyA RNA. Lane 3, purified *E. coli* 16S rRNA (Open arrow). Lane 4, positive control 288mer polyA RNA. Lanes 5 and 6, reverse transcription reaction of *E. coli* 16S rRNA and control polyA RNA with SuperScript III reverse transcriptase. Lanes 7 and 8, reverse transcription reaction after RNA degradation by alkaline hydrolysis showing cDNA products for *E. coli* 16S rRNA (solid arrow) and control 288mer polyA RNA. Lanes 9 and 10, reverse transcription reaction of *E. coli* 16S rRNA and control polyA RNA with Thermostable Group II Intron Reverse Transcriptase (TGIRT). Lanes 11 and 12, reverse transcription reaction after RNA degradation by alkaline hydrolysis showing cDNA products for *E. coli* 16S rRNA (solid arrow) and control 288mer RNA.

Example 2—Covalent Linking of rRNA and Probe Complement Oligonucleotide Facilitated by Oligonucleotide Probe Nucleic acid complexes were produced as described in Example 1. according to the methods of the present disclosure. In this example, subsequent to complex formation, the 3' end of a 16S *E. coli* rRNA and the 5' end of the probe complement oligonucleotide were covalently linked via enzymatic ligation. Gel analysis of the ligation reaction demonstrating that the oligonucleotide probe facilitated ligation of the 3' end of the 16S *E. coli* rRNA to the 5' end of the probe complement oligonucleotide is shown in FIG. 2, panel B. The left panel of panel B shows an unstained gel image. The lower band is a fluorescent 6-FAM-labeled probe complement oligonucleotide. Lane 1-3, pre-ligation reaction samples for: Lane 1) negative control with just probe and probe complement present. Lane 2) positive control with polyA RNA-specific probe and probe complement and control 288mer polyA RNA. Lane 3) 16S rRNA-specific probe, probe complement, and purified 16S rRNA from *E. coli*. Lanes 4-6, post-ligation reaction samples for: Lane 4) negative control. Lane 5) positive control with polyA RNA 288mer. Lane 6) 16S rRNA reaction with probe and fluorescently-labeled probe complement. Size-shifted fluorescent probe complement indicates successful ligation to the 16S rRNA 3' end (Open arrow). The right panel of panel B is the same gel stained with SybrGold. The position of the 16S rRNA is indicated by open arrows.

Example 3—Reading Canonical and Modified Nucleotides in 16S Ribosomal RNA Using Nanopore Direct RNA Sequencing Described herein is direct nanopore sequencing of individual, full-length 16S rRNA absent reverse transcription or amplification. As little as 5 picograms (~10 attomole) of *E. coli* 16S rRNA was detected in 4.5 micrograms of total human RNA. Nanopore ionic current traces that deviated from canonical patterns revealed conserved 16S rRNA base modifications, and a 7-methylguanosine modification that confers aminoglycoside resistance to some pathological *E. coli* strains. This direct RNA sequencing technology has promise for a variety of applications, including rapid identification of microbes (e.g., virulent microbes) in the environment and in patient samples.

Figure 3:
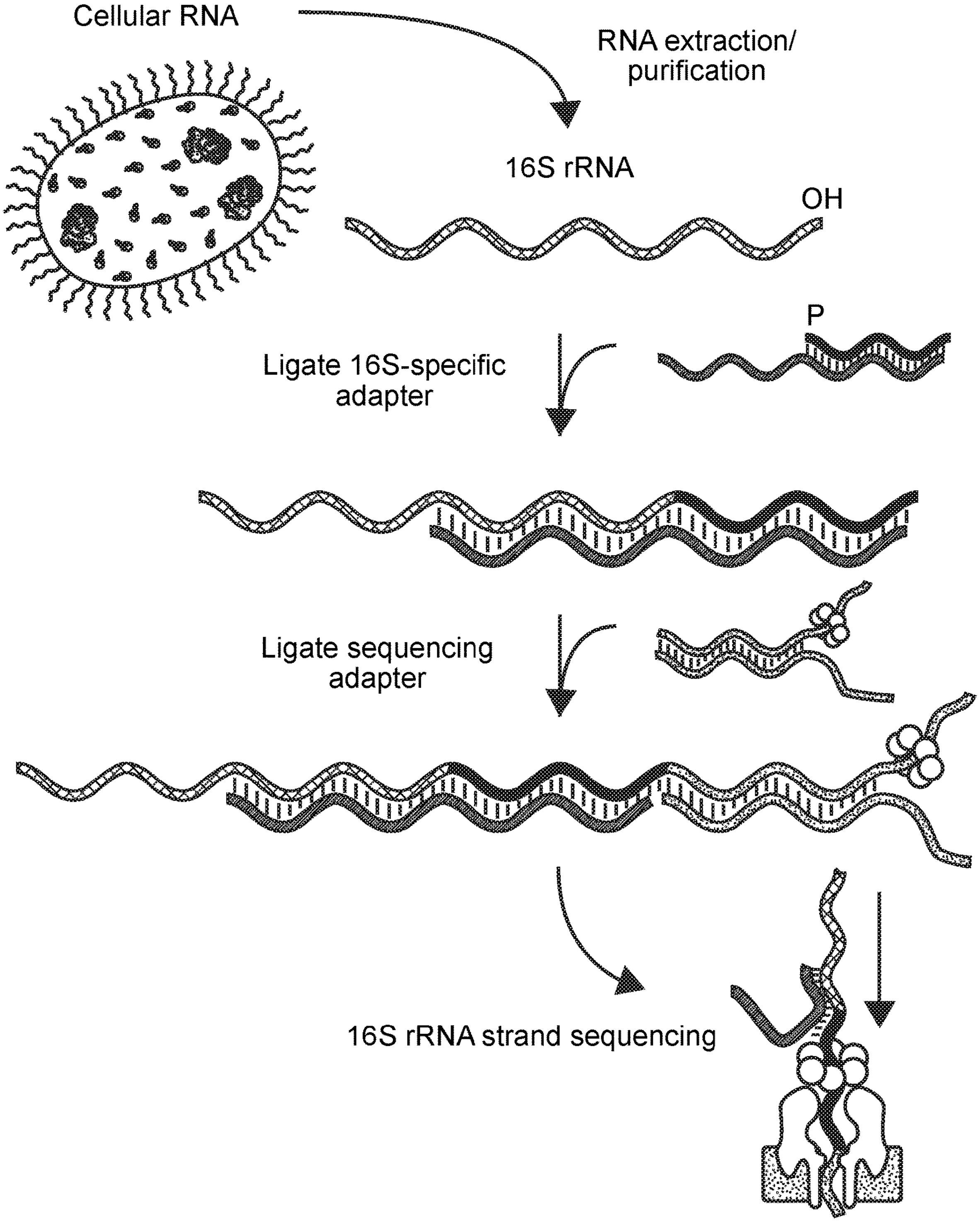
FIG. 3 shows direct nanopore sequencing of individual *E. coli* 16S ribosomal RNA strands. Panel A: Library preparation for direct RNA sequencing. Following RNA extraction, a 16S rRNA-specific adapter is hybridized and ligated to the 16S rRNA 3' end. Next, a sequencing adapter bearing a RNA motor protein is hybridized and ligated to the 3' overhang of the 16S rRNA adapter. The sample is then loaded into the flowcell for sequencing. Panel B: Representative ionic current trace during translocation of a 16S rRNA strand from *E. coli* str. MRE600 through a nanopore. Upon capture of the 3' end of an adapted 16S rRNA, the ionic current transitions from open channel (310 pA; asterisk) to a series of discrete segments characteristic of the adapters (inset). This is followed by ionic current segments corresponding to base-by-base translocation of the 16S rRNA. The trace is representative of thousands of reads collected for individual 16S rRNA strands from *E. coli*. Panel C: Alignment of 200,000+ 16S rRNA reads to *E. coli* str MRE600 rrnD 16S rRNA reference sequence. Reads are aligned in 5' to 3' orientation, after being reversed by the base-calling software. Numbering is according to canonical *E. coli* 16S sequence. Coverage across reference is plotted as a smoothed curve. In this experiment, 92% of reads that passed quality filters aligned to the reference sequence. Data presented here are from a single flow cell.
Figure 3:
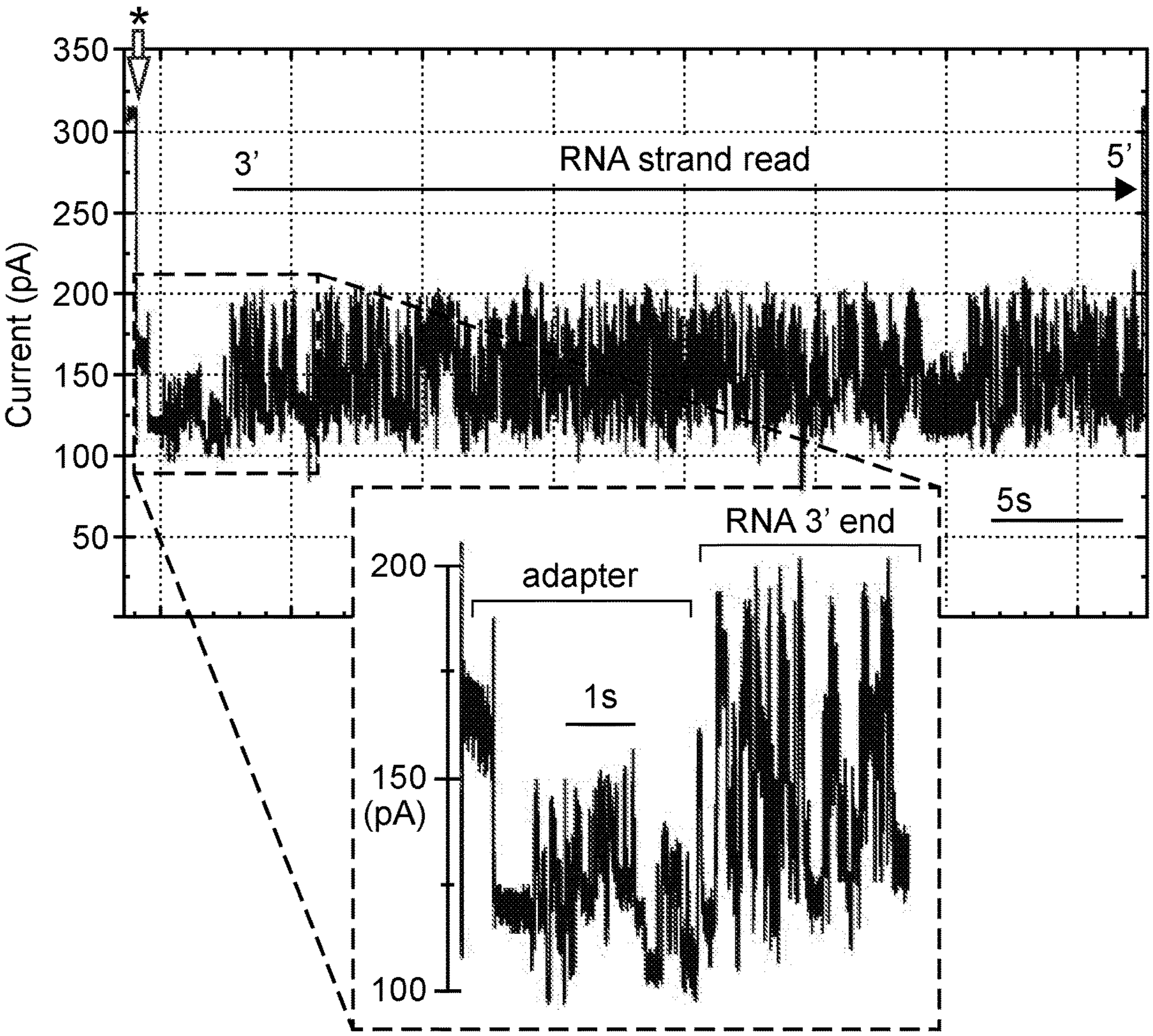
Figure 3:
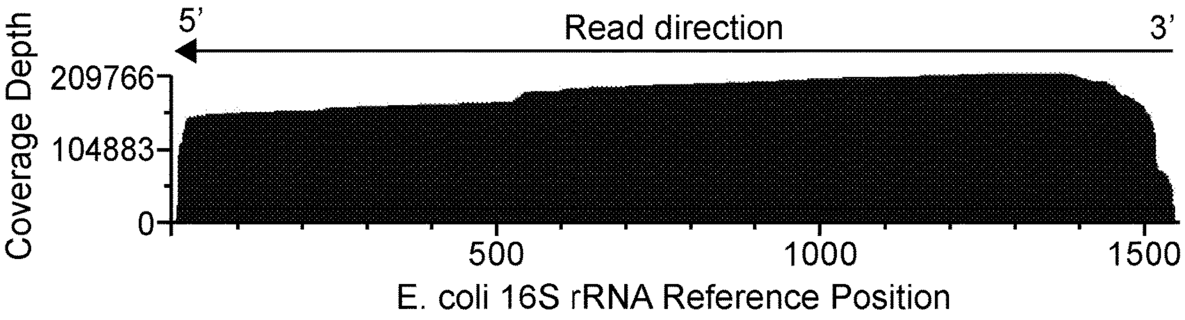

The strategy illustrated in FIG. 3 (panel A) was employed to prepare 16S rRNA for direct nanopore sequencing. Briefly, 16S rRNA was ligated to an adapter bearing a 20 nt overhang complementary to the 3'-end of the 16S rRNA (FIG. 1 and FIG. 3 (panel A)). This overhang included the Shine-Dalgarno sequence, which is highly conserved in prokaryotes. Next, a modular Oxford Nanopore Technologies (ONT) adapter bearing a RNA motor protein was hybridized and ligated to the adapted RNA strands, thus facilitating capture and sequencing on the nanopore sequencing device (in this example, a MinION sequencing device).

FIG. 3 (panel B) shows a representative ionic current trace caused by translocation of a purified *E. coli* 16S rRNA strand through a nanopore in the MinION array. The read begins with an ionic current pattern characteristic of the ONT RNA sequencing adapter strand followed by the 16S rRNA adapter strand. The 16S rRNA is then processed through the nanopore one base at a time in the 3' to 5' direction. The ionic current features are typical of long nucleic acid polymers processed through a nanopore.

Sequencing of purified 16S rRNA from *E. coli* strain MRE600 produced 219,917 reads over 24 hours that aligned to the reference sequence (FIG. 3, panel C). This represents 94.6% of the total MinION read output for that experiment. Median read length was 1349 bases. Identified were 142,295 reads that had sequence coverage within 25 nt of the 16S rRNA 5'-end and within 50 nucleotides of the 3'-end.

Figure 4:
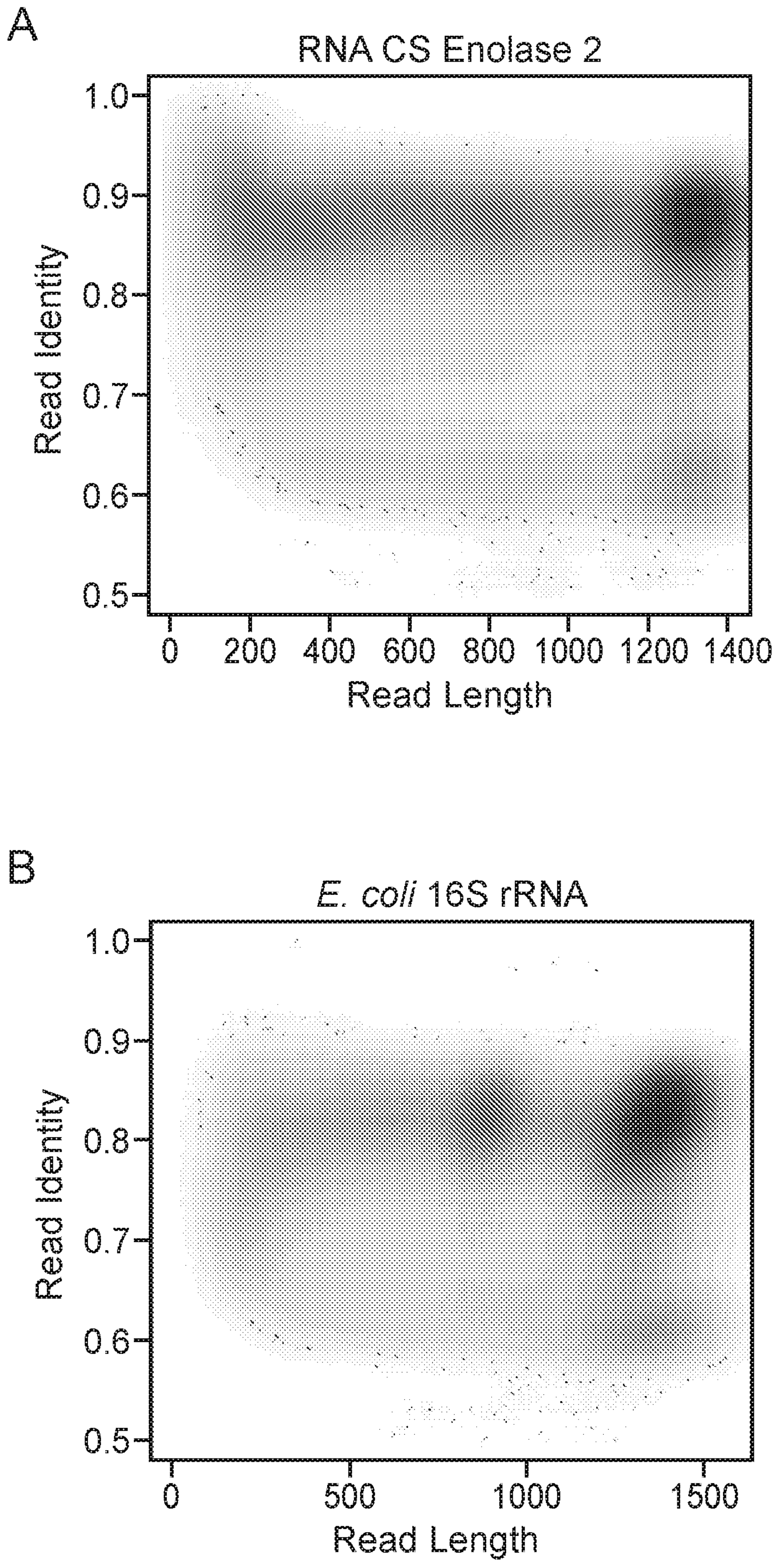
FIG. 4 Shows alignment metrics for Enolase 2 polyA calibration strand and *E. coli* 16S rRNA. Alignments were performed using marginAlign (guide alignments from BWA MEM "-x ont2d" followed by chaining). Panel A: Identity vs. read length for Enolase 2. Panel B: Identity vs. read length for 16S *E. coli* rRNA. Panel C: Coverage across reference for enolase 2 calibration strand. Panel D: Coverage across reference for 16S *E. coli* rRNA.
Figure 4:
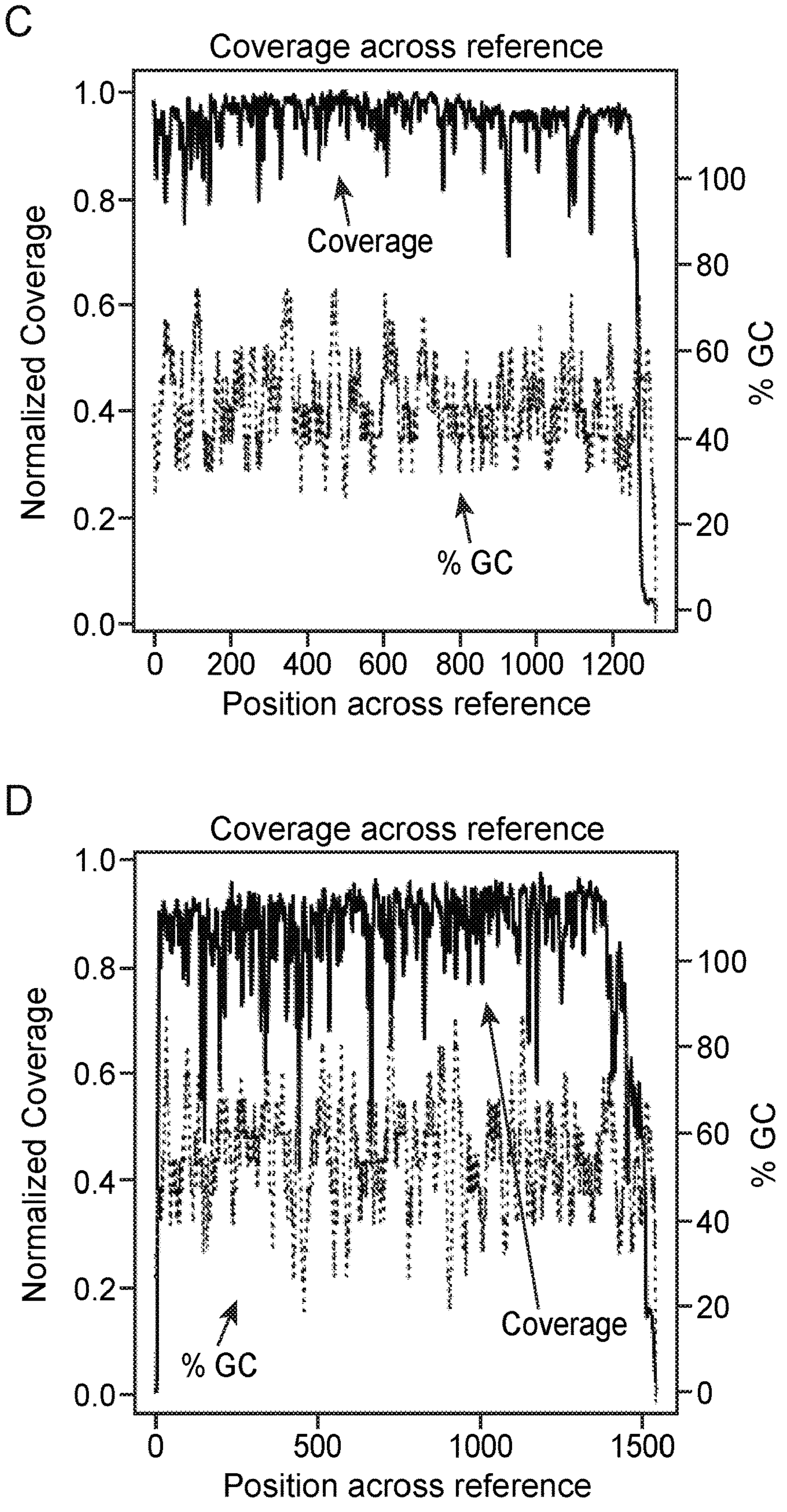
Figure 4:
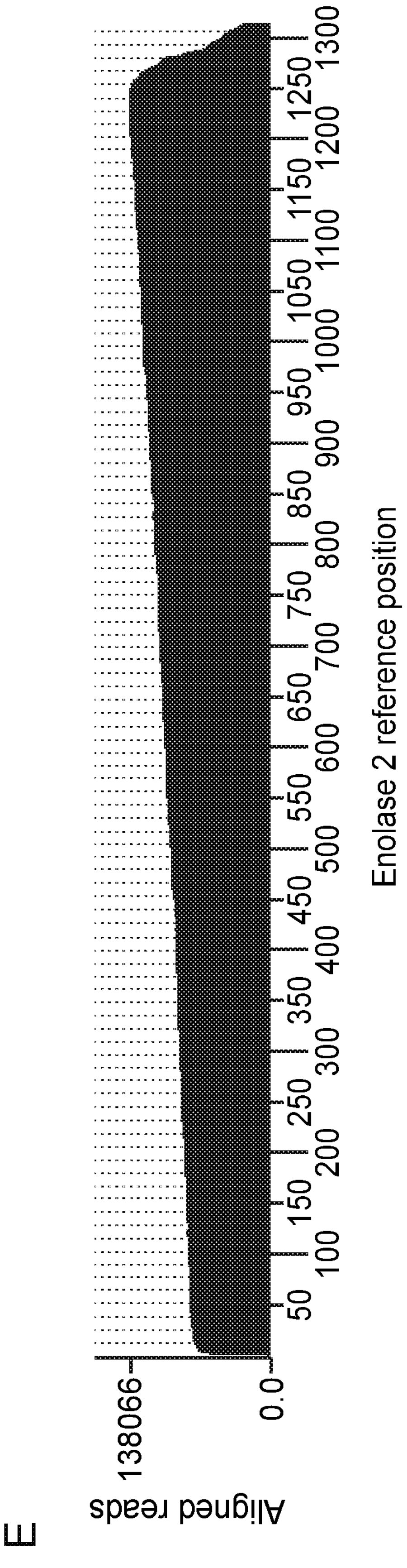
Figure 5:
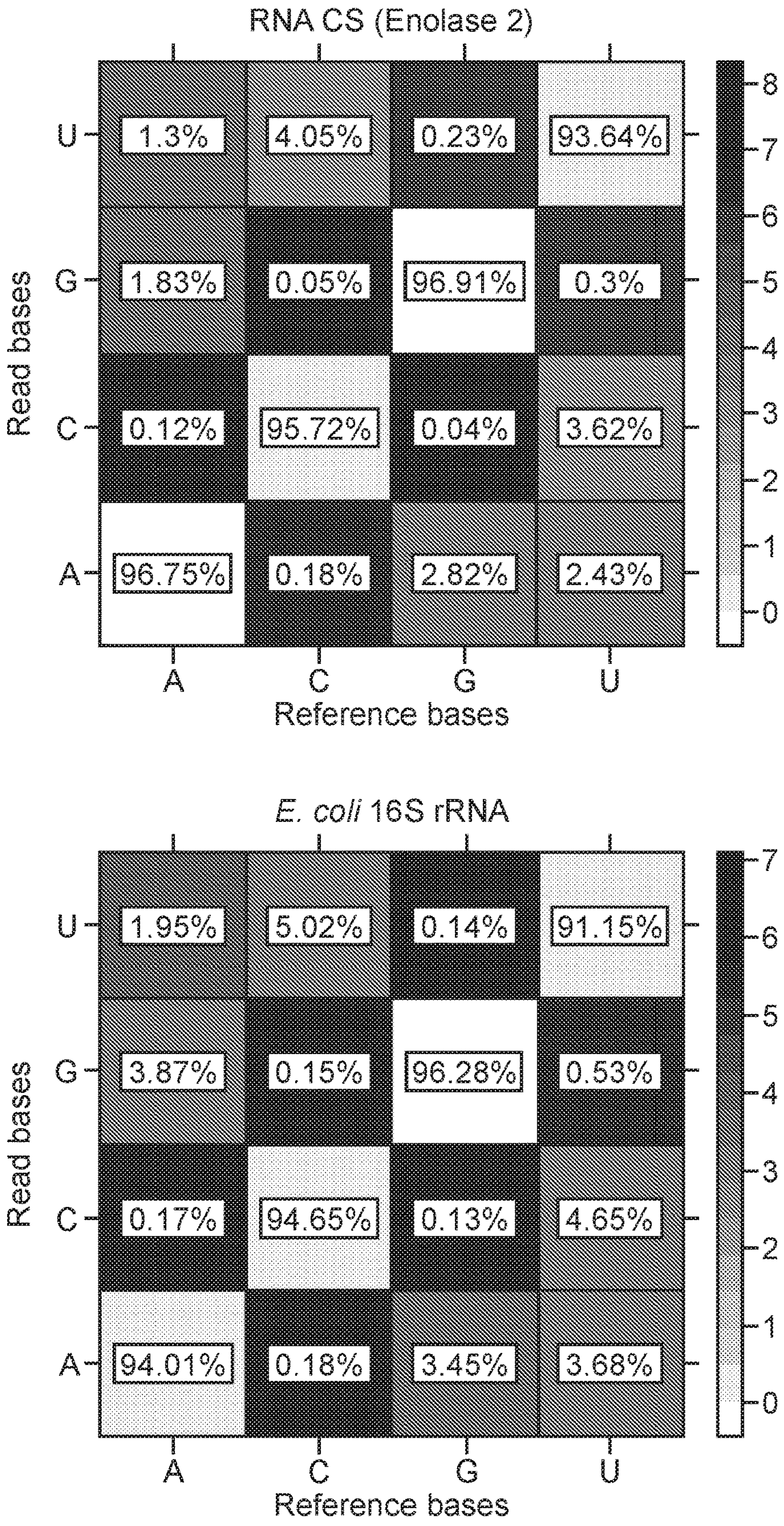
FIG. 5 shows the matrix for substitution emissions for Enolase 2 calibration strand and *E. coli* 16S rRNA. This matrix was determined using marginAlign EM. The matrix shows low rates of C-to-G and G-to-C substitutions, relative to the other substitutions. The color scheme is fitted on a log scale, and the substitution values are on an absolute scale.

The percent read identities were calculated for 16S rRNA sequences and for a *Saccharomyces cerevisiae* Enolase 2 RNA calibration strand supplied by ONT (FIG. 4). The median read identity for 16S rRNA was 81.6% compared to 87.1% for Enolase 2. Close examination of 16 rRNA reads revealed deletion errors in G-rich regions. This is observed as drops in coverage when unsmoothed read coverage is plotted across the *E. coli* 16S rRNA reference (FIG. 4). These errors may represent insufficient training of ONT's base-calling algorithm on G-rich sequences, which are abundant in non-coding structural RNAs such as 16S rRNA (FIG. 5). Other sequencing errors may represent true single nucleotide variants (SNVs) from the 16S rRNA reference sequence used for alignment. *E. coli* strains typically have seven 16S rRNA gene copies, with some of the gene copies differing by as much as 1.1%. Modified nucleotides could also alter ionic current from canonical nucleotides. *E. coli* 16S rRNA contains 12 known nucleotide modifications.

Figure 6:
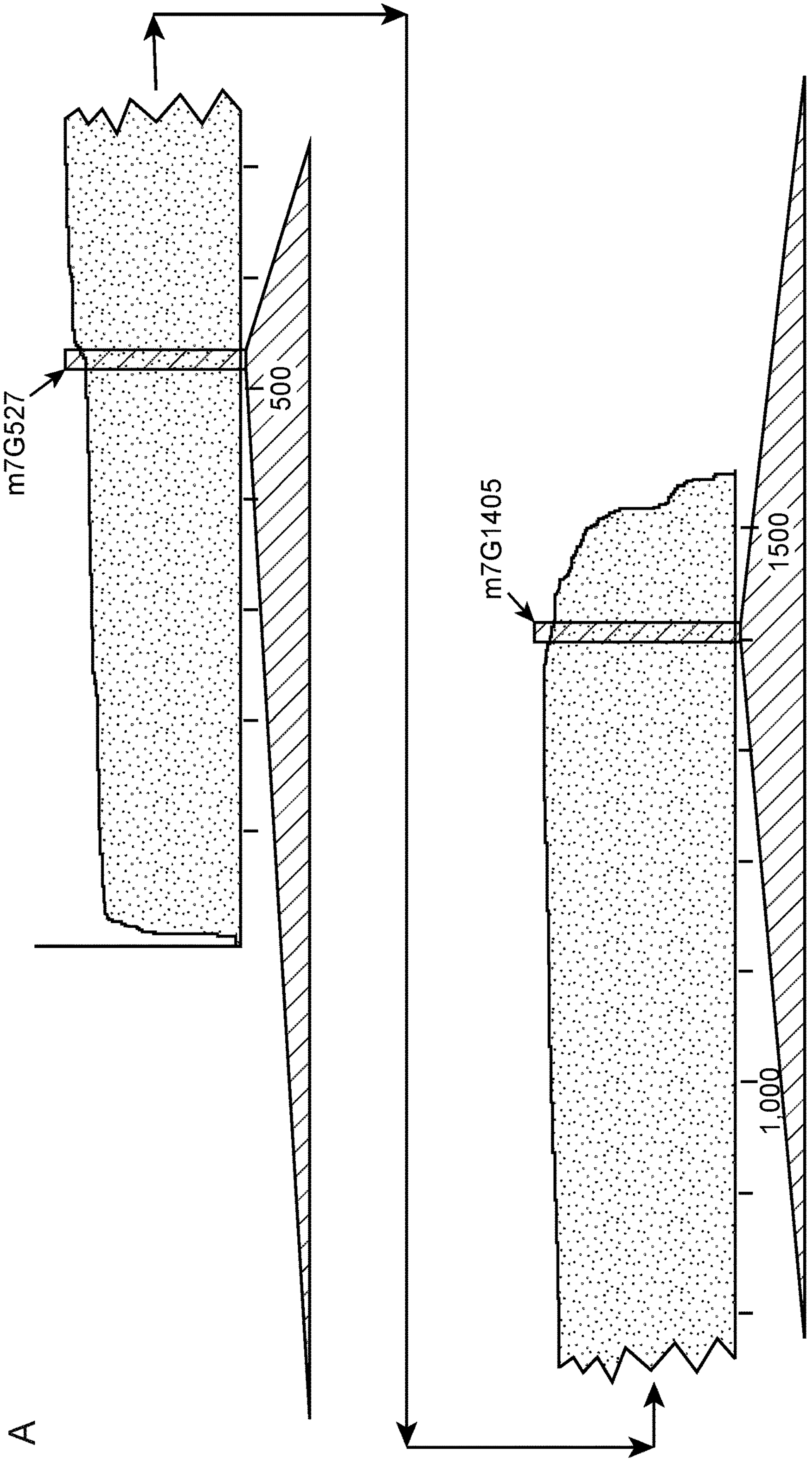
FIG. 6 Detection of 7 mG modifications in *E. coli* 16S rRNA. Panel A: Diagram showing the positions along *E. coli* 16S rRNA that correspond to the expanded sequence alignments in panels B-E. Arrows indicate the positions of G527 and G1405 in the *E. coli* reference. Panel B: Alignment of nanopore RNA sequence reads proximal to position 527 of *E. coli* 16S rRNA. Numbered letters at the top represent DNA bases in the reference 16S rRNA gene. Blue regions in the body of the panel (in the color version of the figure) denote agreement between reference DNA bases and nanopore RNA strand base-calls. White letters denote base call differences between the reference and the nanopore reads, and horizontal white bars represent base deletions in the nanopore RNA reads. Columns highlighted in red (in the color version of the figure) correspond to position 527. The left inset is wt *E. coli* 16S rRNA (m7G527), and the right inset is RsmG mutant strain 16S rRNA (canonical G527). Panel C: Nanopore ionic current traces proximal to position 527 of the *E. coli* 16S rRNA reference. Blue traces (in the color version of the figure) are for wild type 16S rRNA translocation events bearing m7G at position 527; red traces (in the color version of the figure) are for mutant strain 16S rRNA translocation events bearing a canonical G at position 527. Panel D: Alignment of nanopore RNA sequence reads proximal to position 1405 of *E. coli* 16S rRNA. Use of colors, shapes, and letters are as described for panel B. The left inset is engineered mutant *E. coli* (RmtB+) 16S rRNA (m7G1405); the right inset is wt *E. coli* 16S rRNA (G1405). Panel E: Nanopore ionic current traces proximal to position 1405 of the *E. coli* 16S rRNA reference. Blue traces (in the color version of the figure) are for mutant strain 16S rRNA translocation events bearing m7G at position 1405; red traces (in the color version of the figure) are for wild type 16S rRNA translocation events bearing a canonical G at position 1405.
Figure 6:
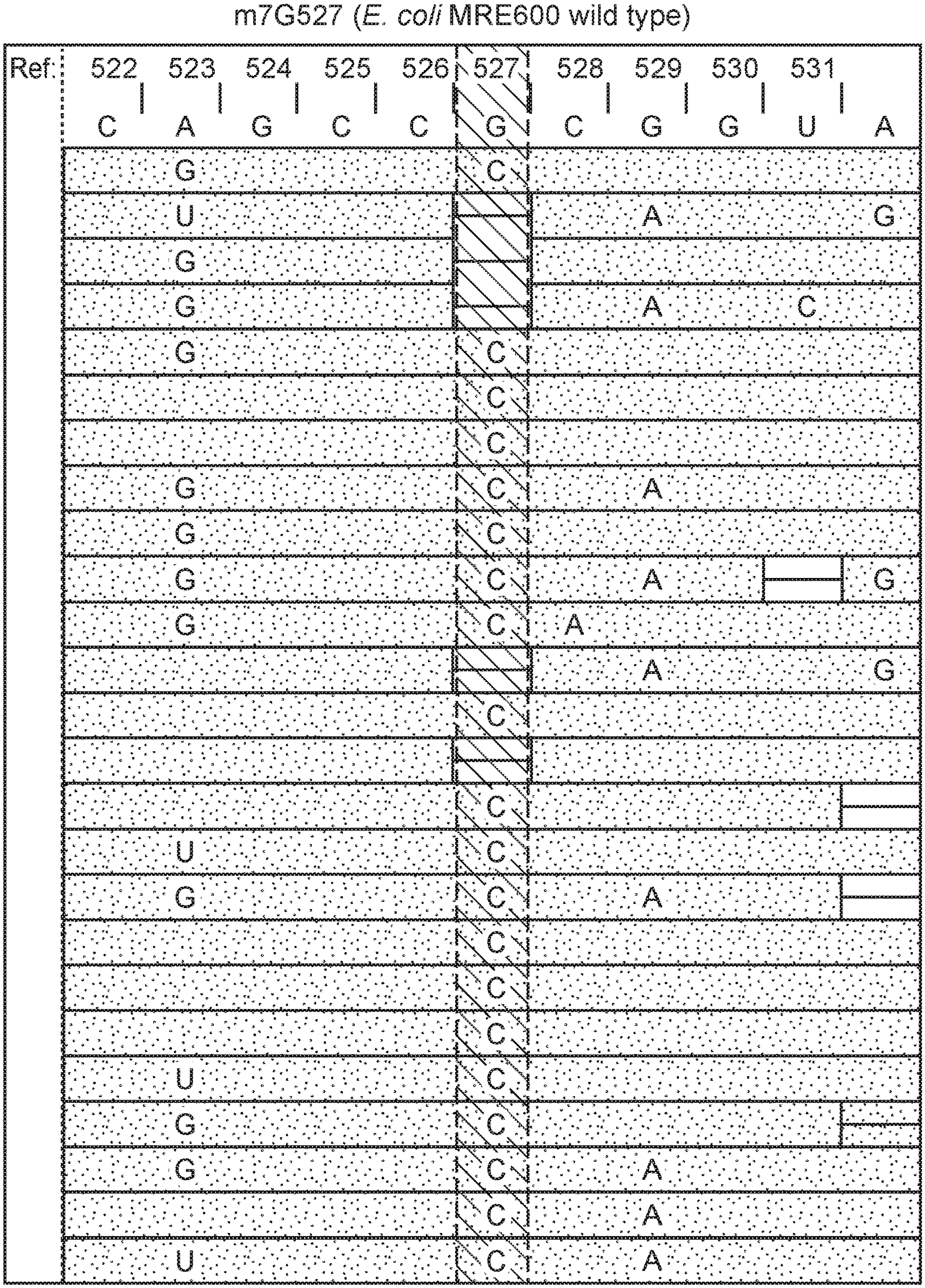
Figure 6:
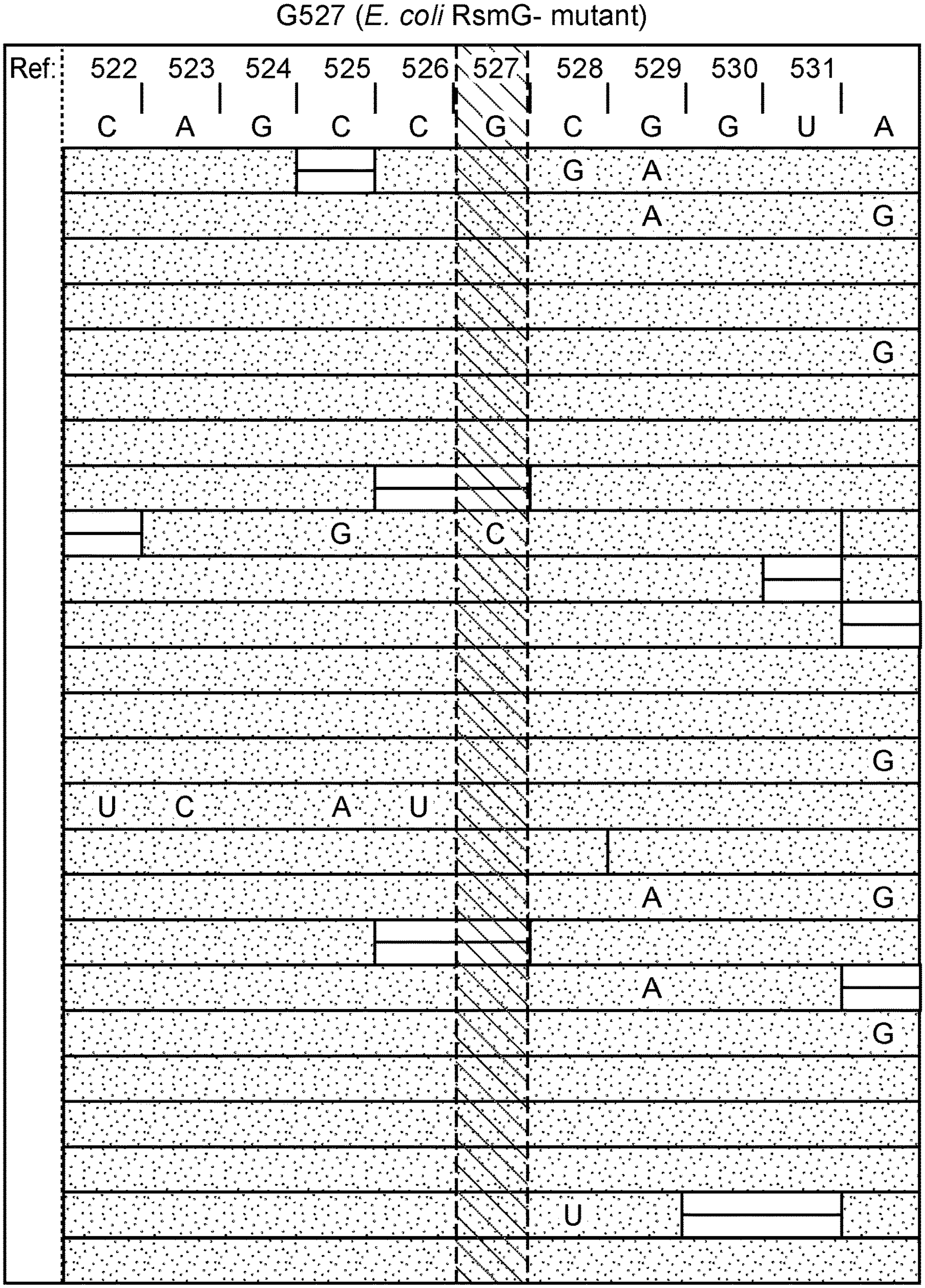
Figure 6:
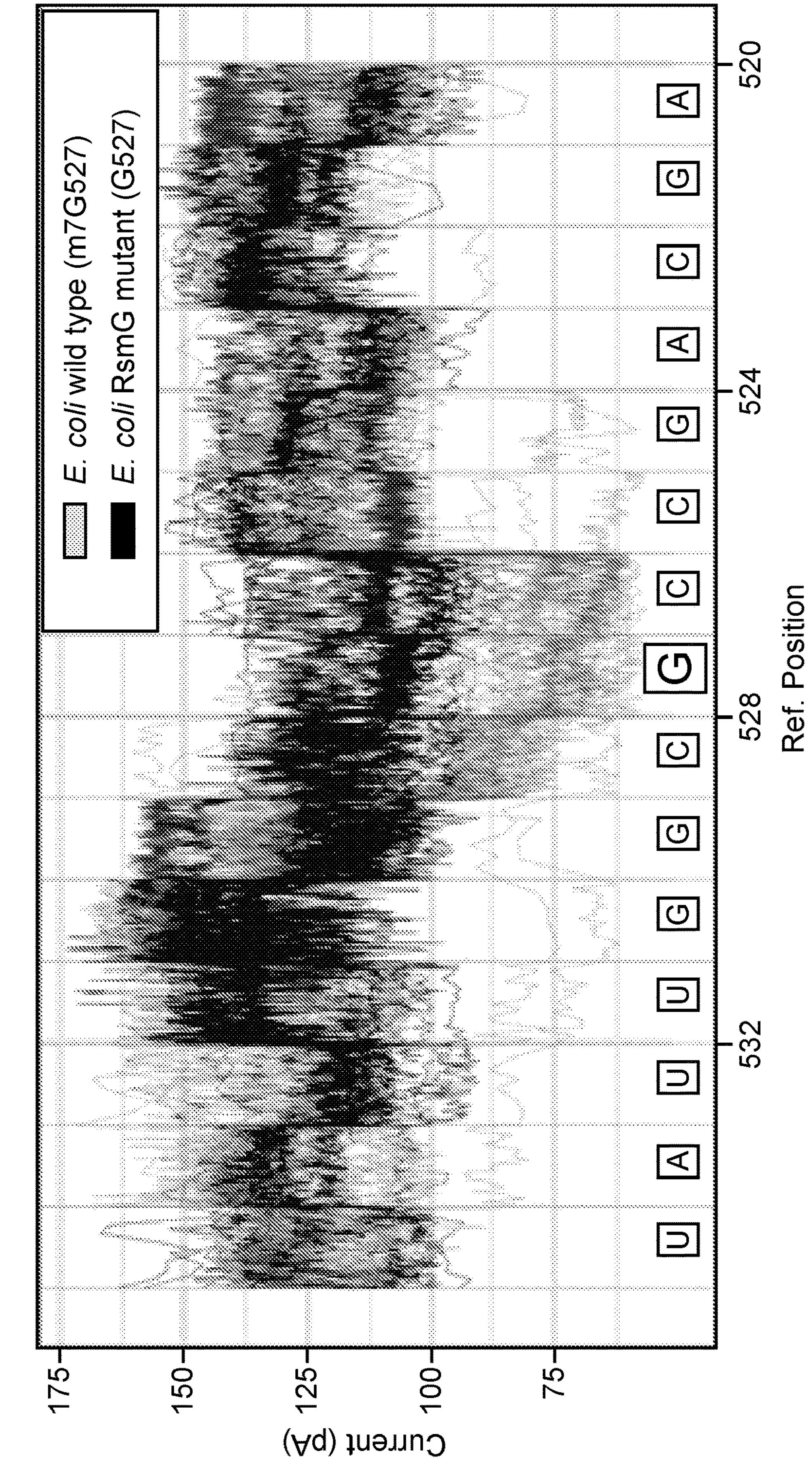
Figure 6:
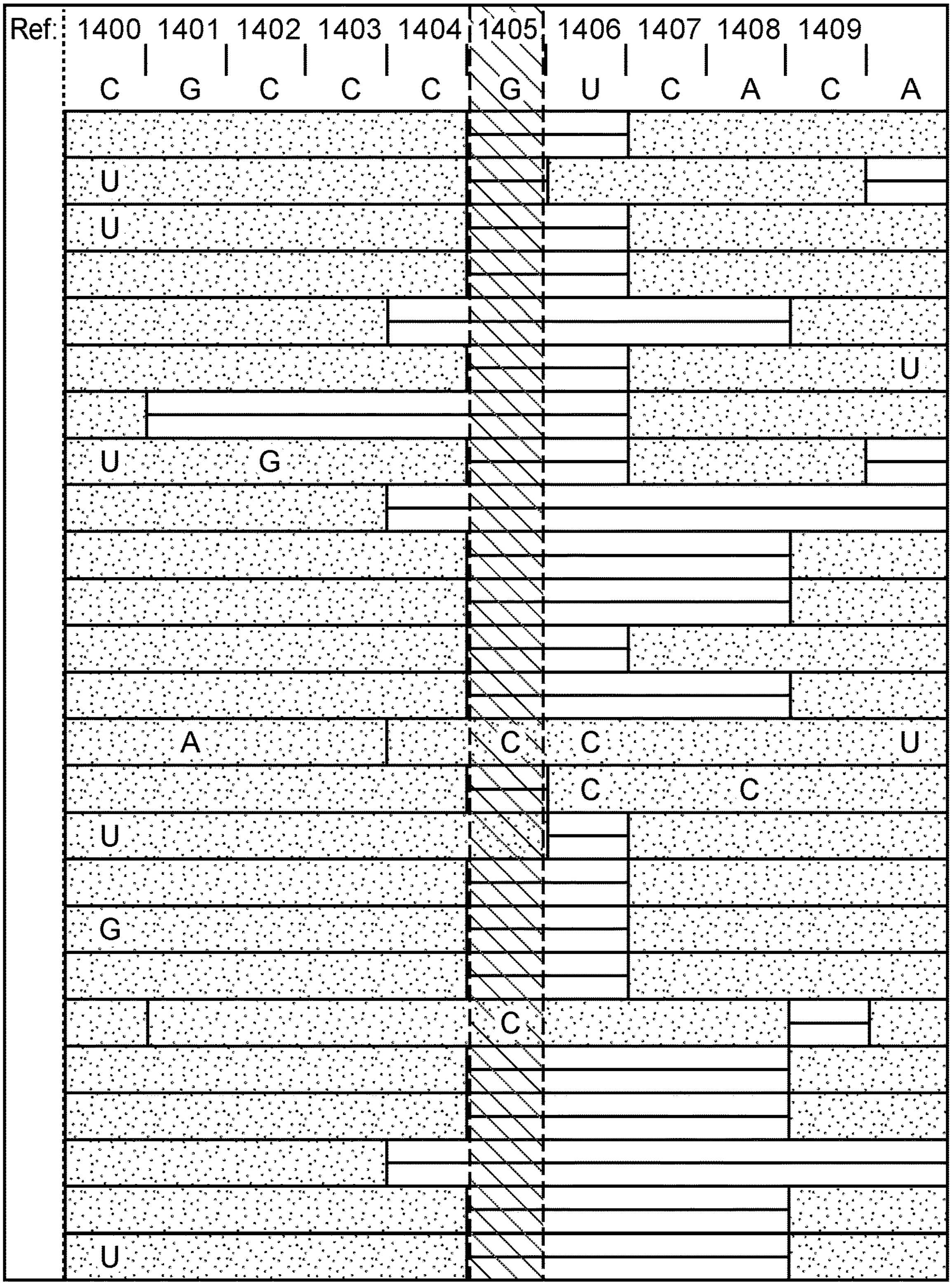
Figure 6:
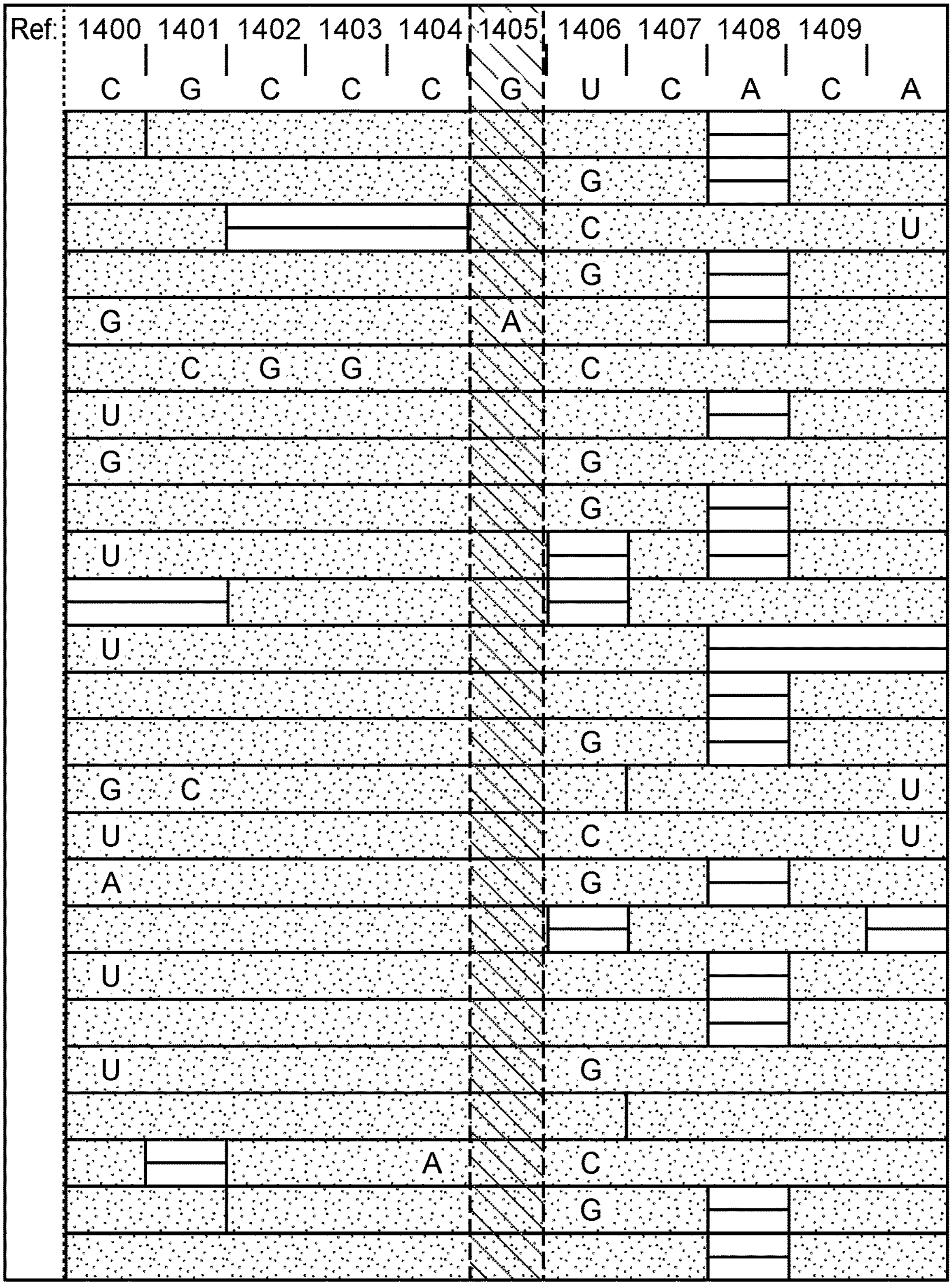
Figure 6:
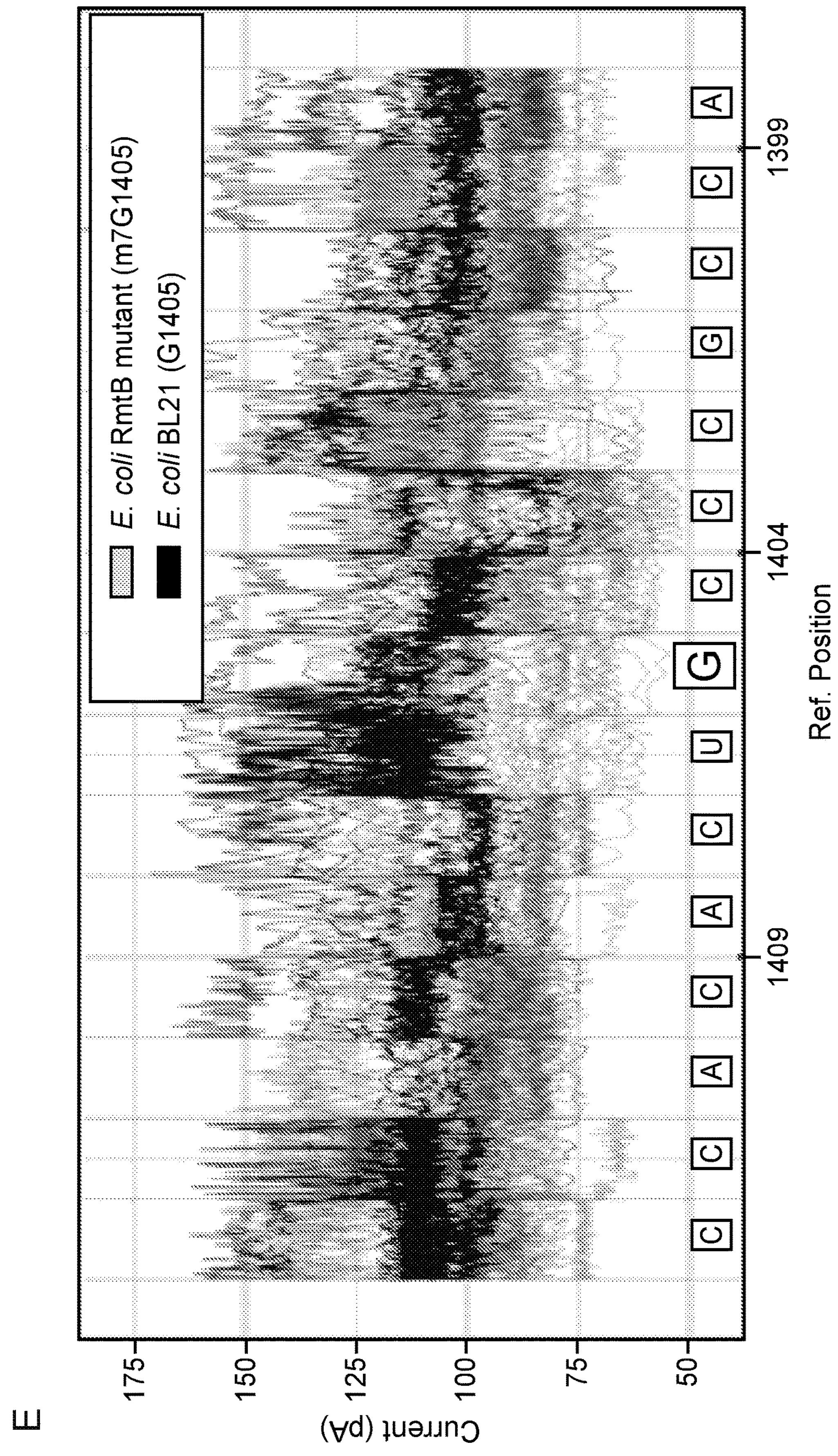

It was predicted that both SNVs and nucleobase modifications would result in reproducible nanopore base-call errors. Therefore, nucleotide positions that were consistently mis-called relative to the *E. coli* MRE600 16S rRNA reference were looked for. Using marginCaller at a posterior probability threshold of 0.3, 24 such positions were detected in the nanopore 16S rRNA reads. Five of these were mis-calls resulting from minor variants in the reference sequence relative to the other 16S rRNA gene copies. For example, at position 79 the reference is adenine (A79), whereas the other six 16S rRNA gene copies are guanosine, in agreement with the majority of nanopore reads. One of the highest probability variants was at G527 in the reference which was systematically mis-called as a C (FIG. 6). This residue is located in a conserved region of the 16S rRNA 530 loop, near the A-site in the ribosome. The guanosine base at this position is known to be methylated at N7 (m7G527), which creates a delocalized positive charge. It was hypothesized that this modification would significantly alter the ionic current segments that contain m7G527, thus resulting in the systematic base-call error.

Figure 7:
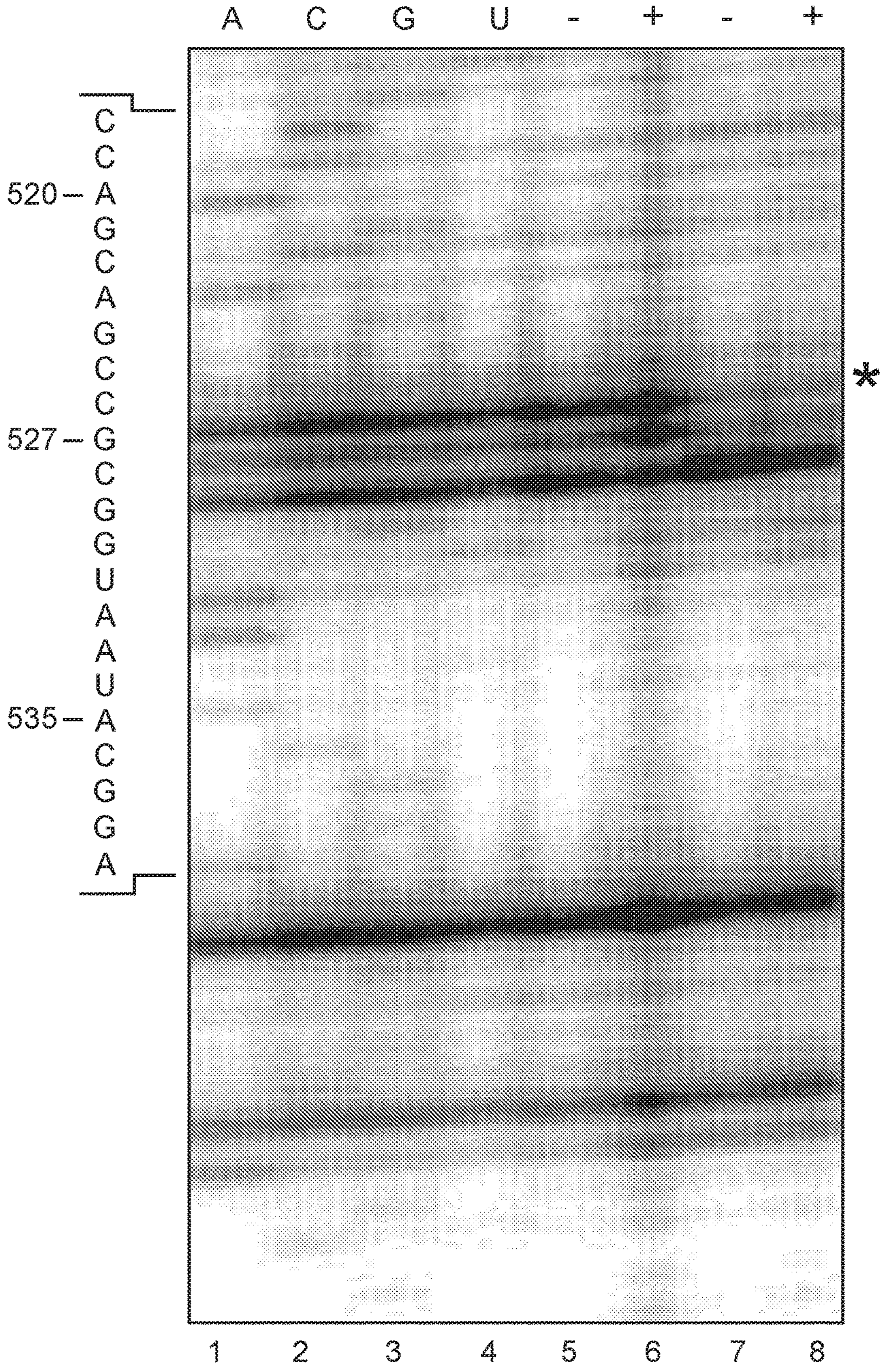
FIG. 7 Confirmation of guanosine N7-methylation (m7G) at positions 527 and 1405 in *E. coli* 16S rRNA. Panel A: Canonical m7G527 is present in wild type *E. coli* MRE600 and absent in *E. coli* strain JW3718A. Sodium borohydride/aniline cleavage was used to detect m7G in 16S rRNA for *E. coli* str. MRE600 (wild type) bearing m7G527 and RsmG deficient (mutant) *E. coli* str. BW25113 JW3718A. Lanes 1-4 are sequencing lanes for A, C, G, and U respectively. Wild type 16S rRNA from *E. coli* str. MRE600 is used as the template. Lanes 5 and 7: sodium borohydride/aniline treatment (labeled+) of 16S rRNA from wild type 16S rRNA and 16S rRNA from RsmG mutant *E. coli*, respectively. Strand cleavage should result in an extension stop 1 nt ahead of G527. Lane 6 and 8: untreated 16S rRNA for wild type and mutant 16S rRNA. Primer extension products were run on denaturing 6% acrylamide gel, and imaged using a phosphore imager. The asterisk indicates G527 on the gel. Panel B: RmtB confers a kanamycin resistance phenotype via N7 methylation of G1405 in 16S rRNA. Serial dilutions from $10^{-2}$ to $10^{-6}$ (Left to Right) were spotted on LB agar plates for *E. coli* BL21 DE3 pLysS strains transformed with pLM1-RmtB and negative control pLM1-RmtBΔ. The pLM1 plasmids use a pET32a backbone that contains an ampicillin resistance gene. The RmtB gene is under the control of a lactose inducible T7 promoter. Plates are supplemented with: 100 ug/ml Ampicillin (top), 100 ug/ml Ampicillin+200 ug/ml Kanamycin+1% glucose (middle), 100 ug/ml Ampicillin+200 ug/ml Kanamycin+1 mM IPTG (bottom).
Figure 7:
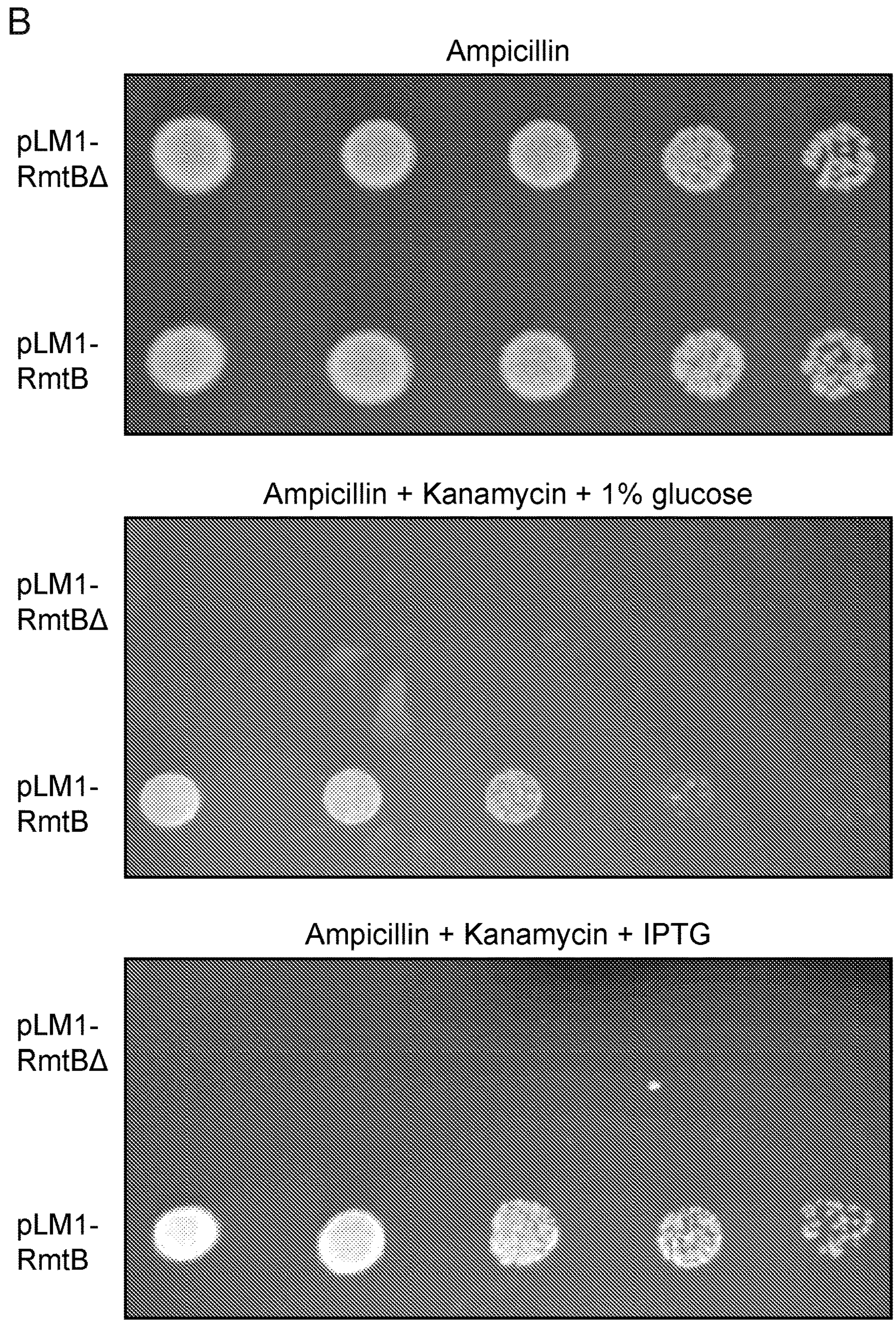

To test this hypothesis, wild-type *E. coli* 16S rRNA nanopore reads were compared with reads for an *E. coli* strain that lacks the enzyme (RsmG) responsible for N7 methylation at G527. The absence of methylation at G527 in the RsmG deficient strain by chemical cleavage (FIG. 7, panel A) was validated. As predicted, a canonical guanosine base at position 527 in the mutant strain eliminated the reproducible base-call error seen in the wild-type *E. coli* strain (FIG. 6, panel B). Examination of ionic current segments containing G527 and m7G527 in RNA strands for the respective strains confirmed that m7G alters ionic current relative to canonical G (FIG. 6, panel C).

Typically, *E. coli* 16S rRNA contains only one m7G at position 527. However, some pathogenic strains that are resistant to aminoglycosides contain an additional m7G at position 1405. The enzymes responsible for G1405 methylation, such as RmtB, are shuttled on multidrug-resistance plasmids, and are thought to have originated from microbes that produce aminoglycosides, e.g. *Streptomyces*. Given the pronounced signal difference for m7G at position 527, it was thought to be possible to detect m7G in this context.

To this end, an *E. coli* strain was engineered that carried RmtB on an inducible plasmid (pLM1-RmtB, see Methods). It was confirmed that this RmtB+ strain was aminoglycoside resistant, (FIG. 7, panel B) consistent with N7 methylation of G1405. 16S rRNA sequence reads for this strain (RmtB+) were then compared with reads from the parent *E. coli* strain (BL21) without the plasmid (FIG. 6, panel A and D). An increase in deletions and base mis-calls in 16S rRNA reads for the RmtB+ strain was observed at position G1405 and the adjacent U1406. These mis-calls were absent in the 16S rRNA reads for the parent BL21 strain, which bears a canonical guanosine at G1405. Examination of ionic current segments containing G1405 and m7G1405 in RNA strands for the respective strains confirmed that m7G alters ionic current relative to canonical G (FIG. 6, panel E), as was observed at position 527. In this region, methylated cytosines at positions 1402 and 1407 may also contribute to the aberrant ionic current, which could account for the base mis-calls proximal to those bases in the parent strain (FIG. 6, panel D, right panel).

Figure 8:
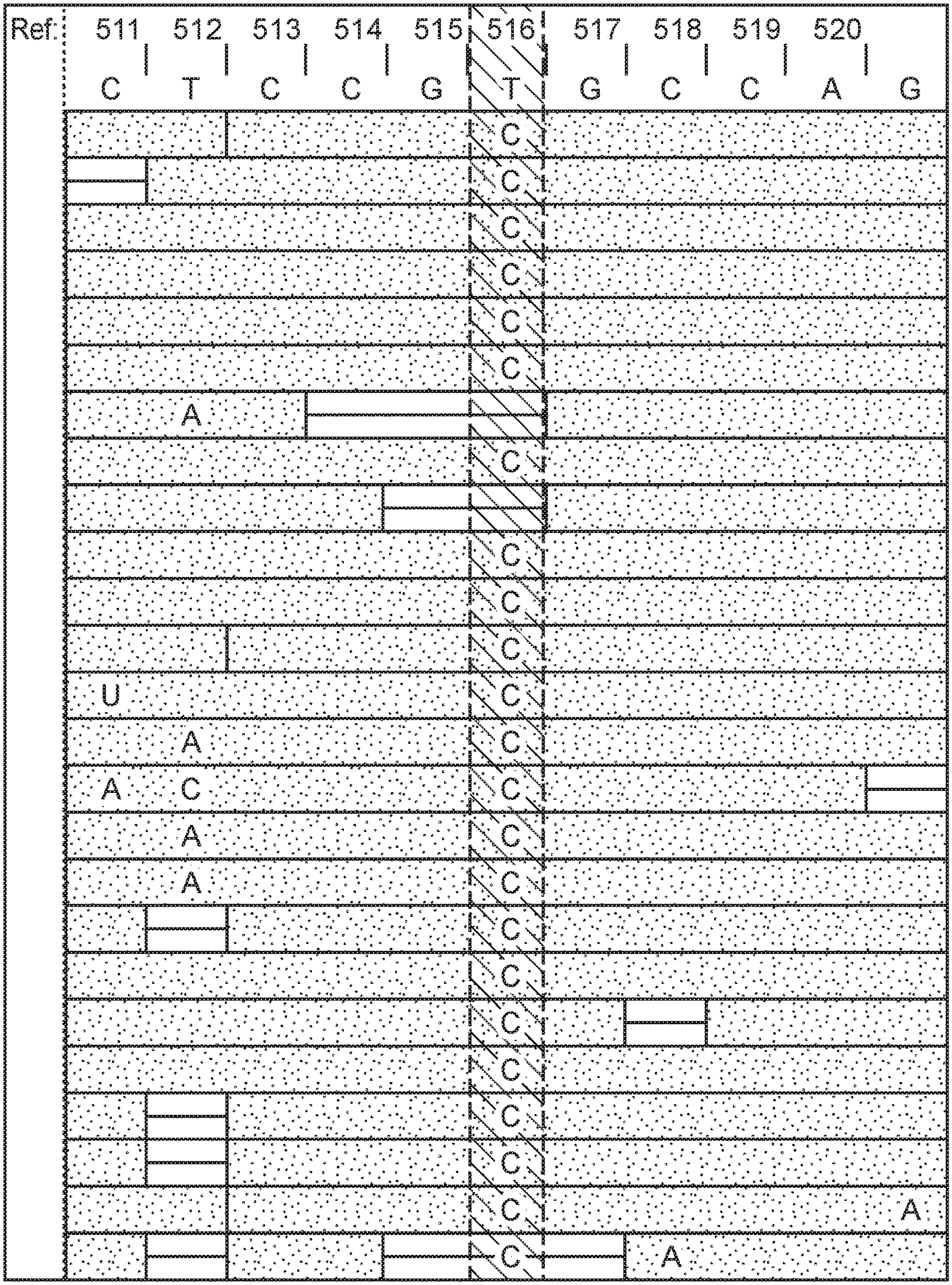
FIG. 8 Inference of pseudouridine in *E. coli* 16S rRNA direct sequencing reads. Panel A: Comparison of aligned reads from strands containing putative pseudouridine versus strands bearing canonical uridine at position 516. Reads are aligned to the *E. coli* MRE600 rrnD 16S rRNA reference sequence. Shown are twenty-five 16S rRNA reads from separate sequencing runs for wild-type *E. coli* (str. MRE600), which presumably bears a pseudouridine at U516 (ψ516) and an RsuA mutant strain (str. JW2717), which should have a canonical U at 516. Green shading (in the color version of the figure) indicates the position of U516 (shown as a T in the reference sequence). Panel B: Signal-level alignment of approximately thirty 16S rRNA reads covering position U516 from WT *E. coli* str. MRE600 and RsuA deficient strain JW2717. Pseudouridylation site, U516, is shown in large font. The sequence is shown 3'-to-5' due to the fact that ionic current signal is 3'-to-5'. Numbering uses standard *E. coli* 16S rRNA numbering.
Figure 8:
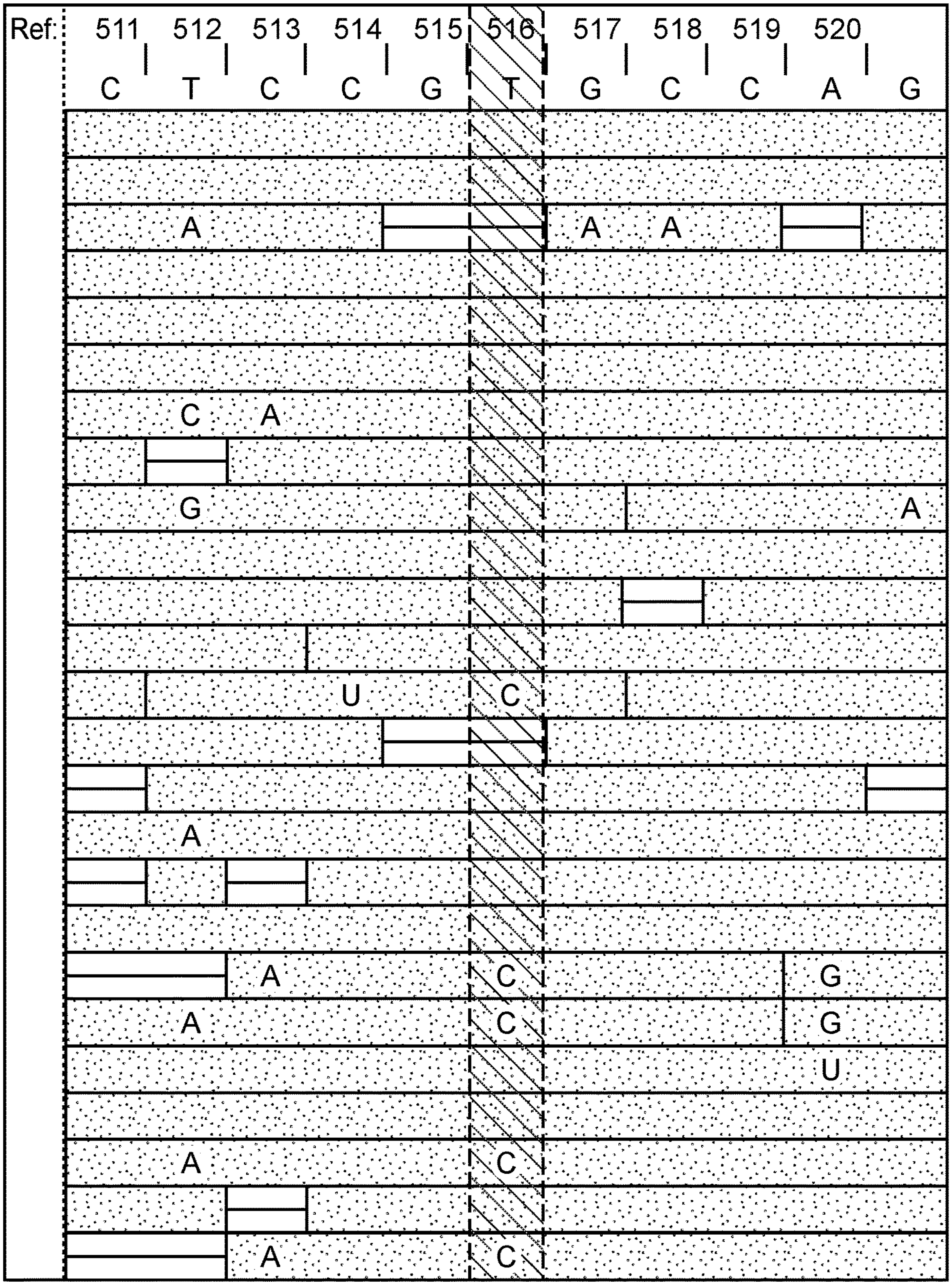
Figure 8:
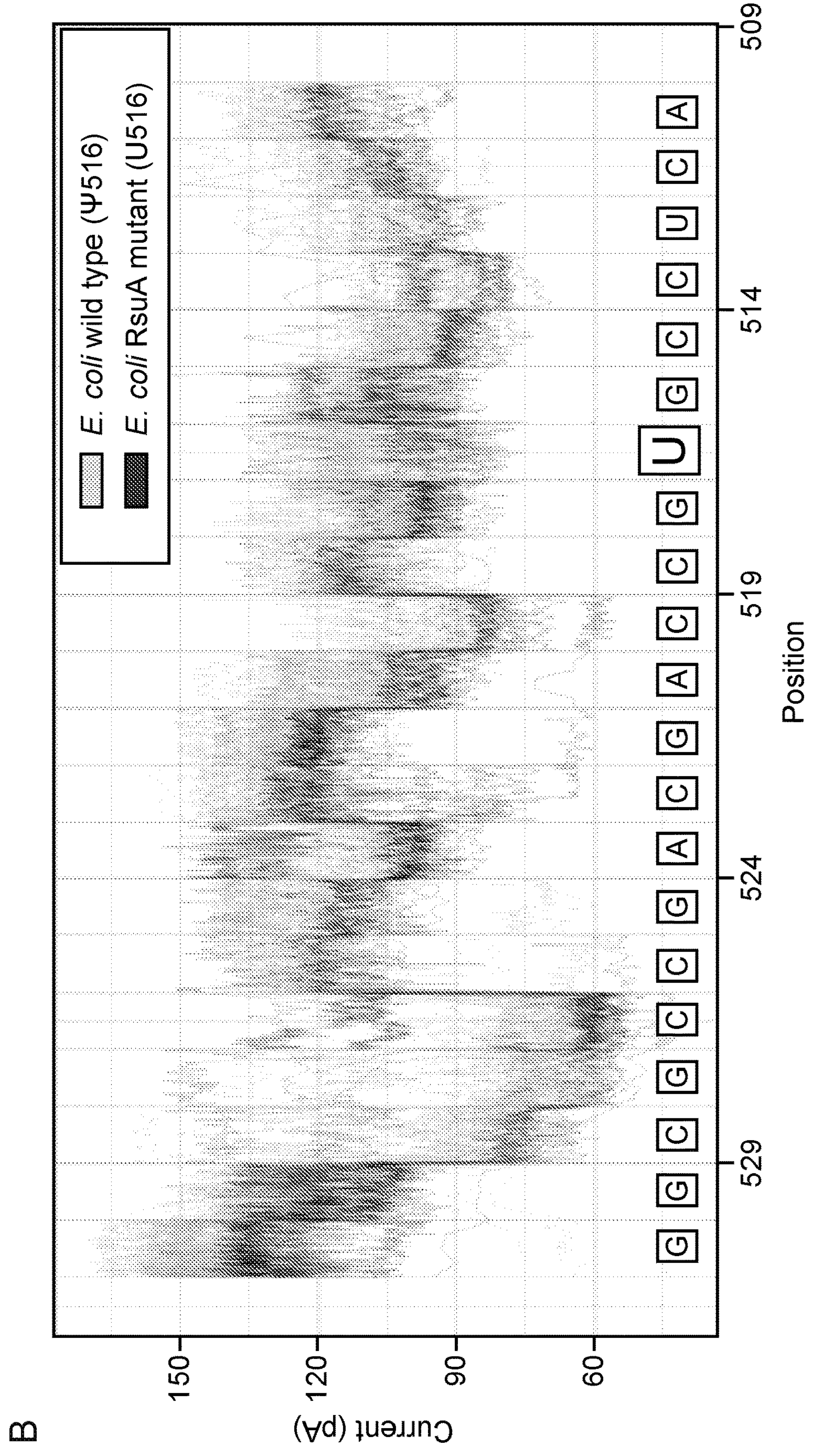

Nanopore detection of epigenetic RNA modifications is not limited to m7G. While examining base mis-calls proximal to G527, a systematic mis-call at U516 (FIG. 8) was also noted. This mis-called position had the highest probability variant in our marginCaller analysis. It was hypothesized that this was due to pseudouridylation at U516 which is typical in *E. coli* 16S rRNA. As a test, nanopore reads for the wild type strain were compared with reads for a mutant strain (RsuAΔ) bearing a canonical uridine at position 516. It was found that mis-calls and ionic current deviations present at U516 in the wild type were absent in the mutant strain (FIG. 8), which is consistent with the hypothesis.

Figure 9:
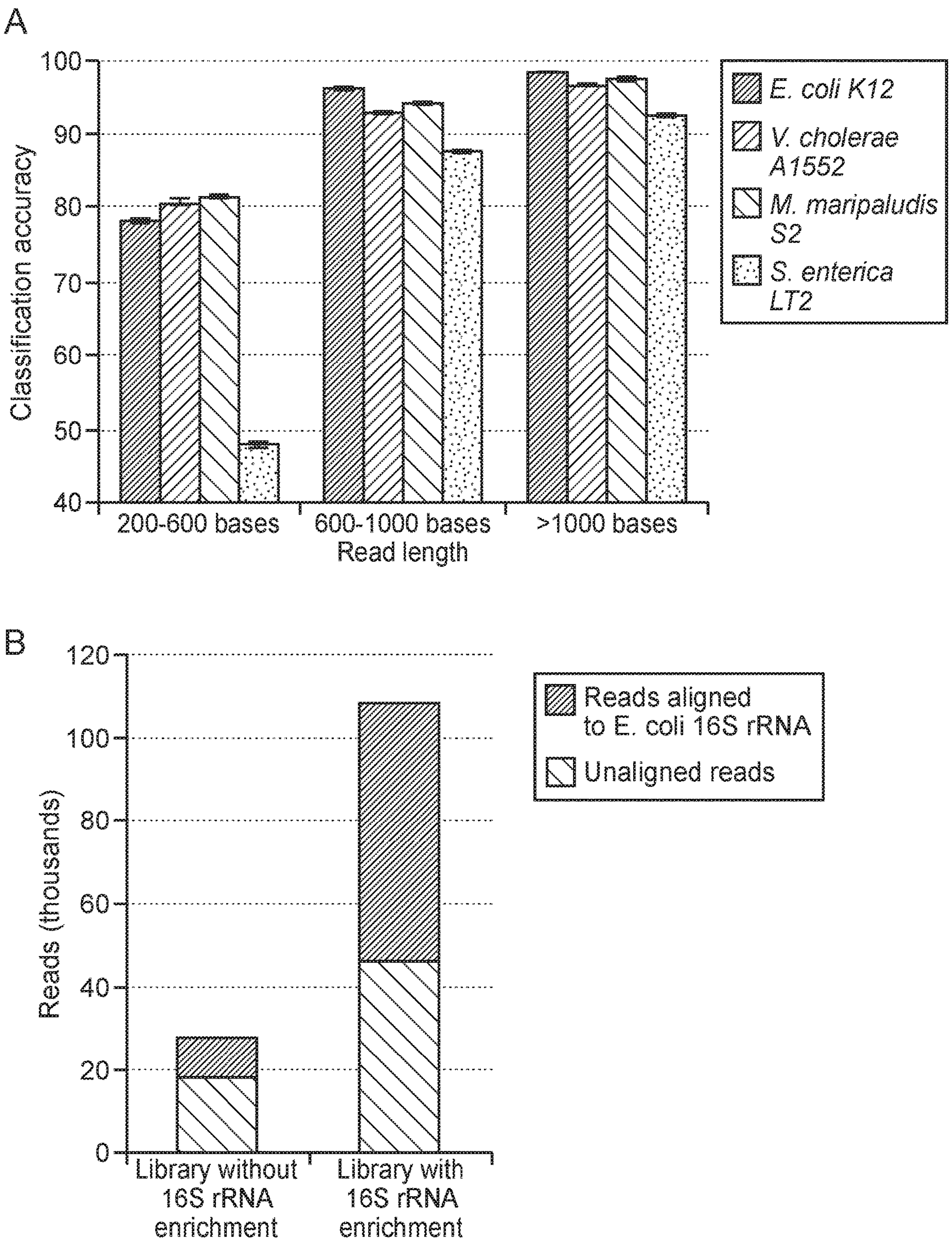
FIG. 9 Direct 16S rRNA sequencing discriminates among microbes and can detect *E. coli* 16S rRNA at low concentration in a human RNA background. Panel A: Classification accuracy from an in silico mixture of 16S rRNA reads from four microbes. Reads were binned based on length and 10 iterations of classification using 10,000 randomly sampled reads per microbe were performed. A read was called as correctly classified if it aligned to one of the 16S rRNA reference sequences for that microbe. The error bars indicate one standard deviation for the 10 iterations. Panel B: 16S rRNA sequencing yield for libraries prepared from *E. coli* str. K12 total RNA with and without enrichment. Sequencing libraries were prepared from 1.5 pg total RNA. The enrichment library used a desthiobiotinylated version of the 16S rRNA-specific adapter, which was hybridized and selected for using magnetic streptavidin beads (see Methods). The two 16S rRNA sequencing libraries were then prepared essentially the same way. Panel C: 16S rRNA reads from sequencing libraries prepared with *E. coli* str. MRE600 16S rRNA titered into 4.5 pg total RNA from HEK 293T cells. Panel D: 16S read accumulation over time in titration sequencing runs. The lines correspond to libraries shown in panel C.
Figure 9:
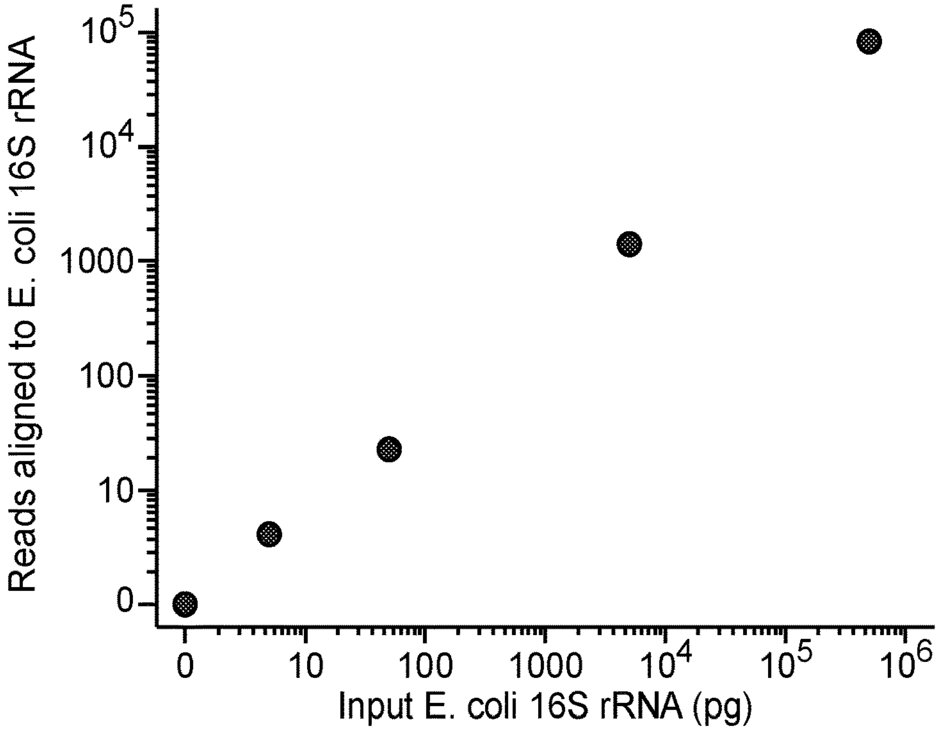
Figure 9:
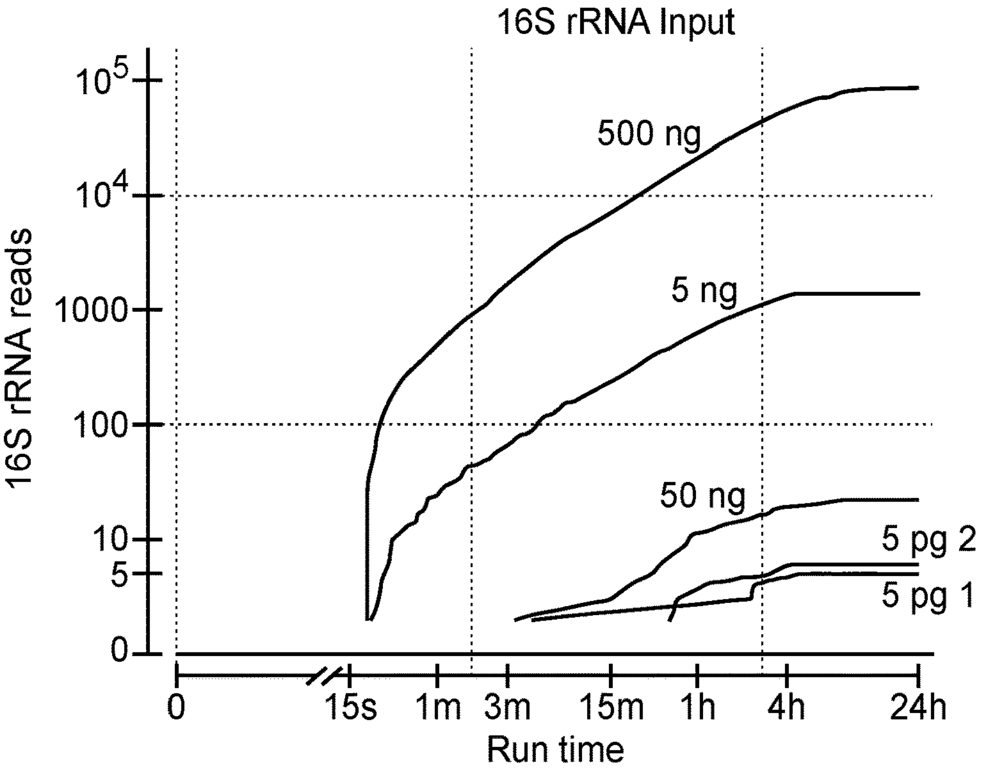
Figure 10:
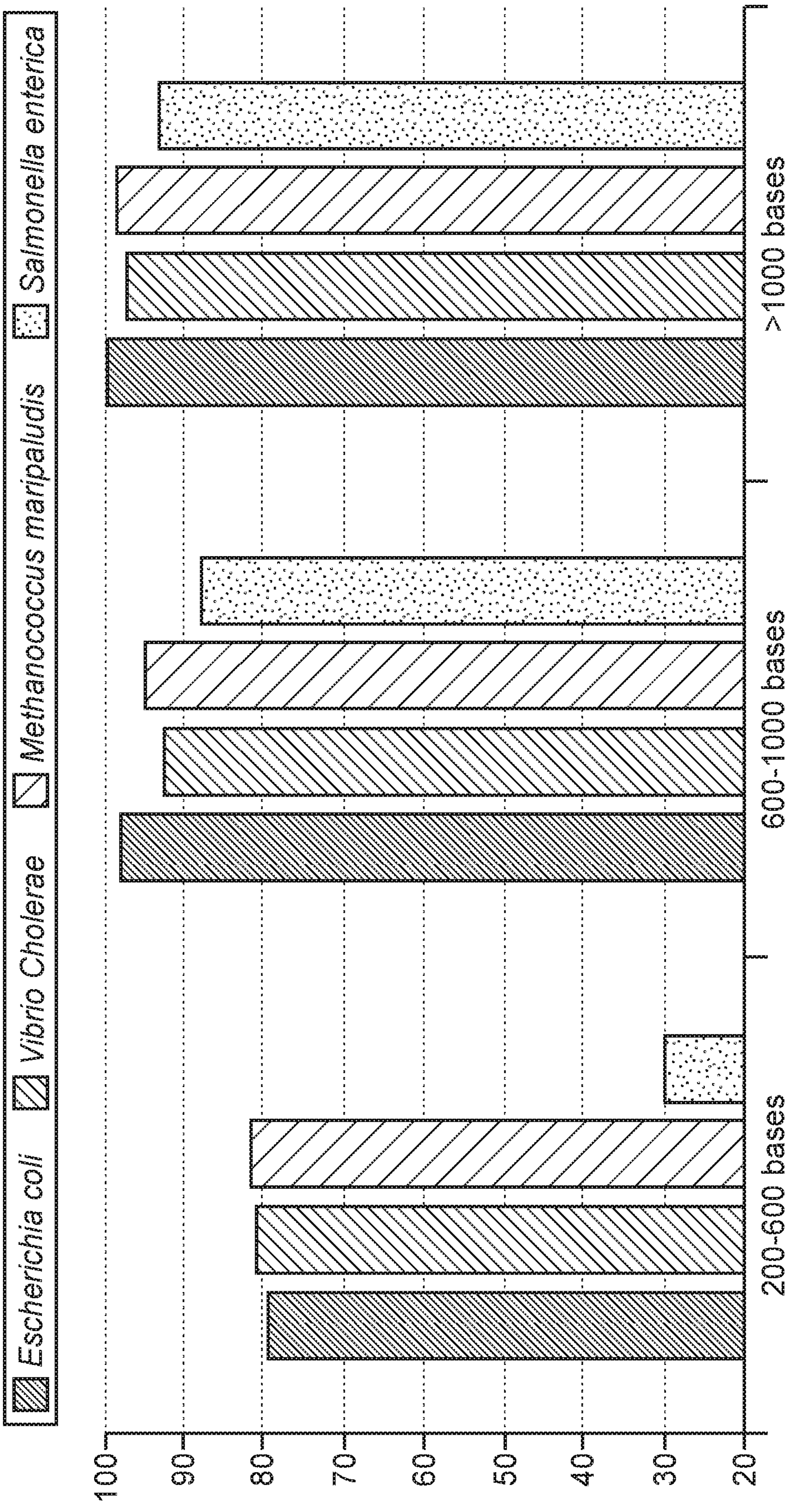
FIG. 10 Microbial classification accuracy using all data. The classification was performed from an in silico mixture of 16S rRNA reads from four microbes. Reads were binned based on length. A read was called as correctly classified if it aligned to one of the 16S rRNA reference sequences for that microbe.

Another important feature of direct nanopore 16S rRNA reads is that they are mostly full-length. It has been established that more complete 16S sequences allow for improved taxonomic classification. To test if full-length 16S rRNA reads gave better classification than short reads, purified 16S rRNA was sequenced from three additional microbes (*Methanococcus maripaludis* str. S2, *Vibrio cholerae* str. A1552, and *Salmonella enterica* str. LT2). These were chosen to give a range of 16S rRNA sequence similarities to *E. coli* (68.1%, 90.4%, and 97.0% identity respectively). The 16S rRNA adapter sequence was altered slightly for each microbe (see Methods). We binned reads by length, sampled 10,000 reads per bin for each microorganism, mixed them in silico, and aligned them to 16S rRNA sequences for all four microbes. A read was counted as correctly classified if it aligned to a 16S rRNA reference sequence for the source microorganism. As predicted, the classification accuracy increased with read length from 67.9% for short reads (200-600 bases) to 96.9% for long reads (>1000 bases) (FIG. 9, panel A). When using all the reads for each bin per microbe (i.e. no sampling), the average classification accuracy increased to 97.8% for long reads (>1000 bases) (FIG. 10).

The previous sequencing experiments required purifying 16S rRNA, which is prohibitively slow for clinical applications. An enrichment strategy was devised that permits selective preparation of 16S rRNA from total bacterial RNA. This involved adding a desthiobiotin to the 16S rRNA adapter (see Methods). The adapter was hybridized to 16S rRNA in a mixture, and then bound to streptavidin-conjugated magnetic beads. This allowed washing and removal of non-specific RNA. The library preparation was then carried out as usual. To test the enrichment method, 16S rRNA sequencing libraries were prepared from the same *E. coli* total RNA preparation with and without the enrichment step. Enrichment increased the number of reads that aligned to 16S *E. coli* rRNA sequence>5-fold relative to the library without enrichment (FIG. 9, panel B).

This suggested that 16S rRNA could be selectively sequenced from a human total RNA background, at relative proportions that would be expected in a clinical sample. To test this, 5 pg to 500 ng of *E. coli* 16S rRNA was titered into 4.5 pg total RNA from human embryonic kidney cells (HEK 293T) and prepared sequencing libraries (FIG. 9, panel C). The lowest mass (5 pg) approximates the amount of 16S rRNA from 300 *E. coli* cells. 4.5 pg of total human RNA approximates the total RNA typically extracted from 1 ml of blood.

A linear correlation was observed between *E. coli* 16S rRNA reads and *E. coli* 16S rRNA concentrations over a 100,000-fold sample range (FIG. 9, panel C). In replicate 5 pg experiments, only 4-5 16S rRNA reads were observed, which nonetheless could be distinguished from the total human RNA negative control (0 16S rRNA reads in 24 hours). Because nanopore data are collected in real-time, we examined how rapidly *E. coli* 16S rRNA was detected in these nanopore sequencing runs. Acquisition times were extracted for all reads that aligned to *E. coli* 16S rRNA (FIG. 9, panel D). At concentrations 5 ng, it was found that the first 16S rRNA read occurred within ~20 seconds of the start of sequencing. This means that some 16S rRNA strands were immediately captured and processed by the MinION upon initiation of the sequencing run. At lower input amounts (<5 ng), *E. coli* 16S rRNA strands were detected in less than one hour.

In summary, full length 16S rRNA was sequenced directly using the ONT MinION nanopore sequencing system. Selective sequencing of bacterial 16S rRNA was demonstrated in a complex mixture of total human RNA, as would be encountered in clinical samples. Library preparation was carried out in under 2 hours, and nanopore sequencing accuracy was sufficient to distinguish among bacteria at the genus level. Some of the benefits of direct nanopore RNA sequencing include, for example the absence of reverse transcription and PCR biases. Arguably the most significant benefit is that each RNA nucleobase is literally touched by the nanoscale sensor as the strand translocates through the pore. In our experiments, this revealed epigenetic modifications in situ along individual *E. coli* 16S rRNA strands.

Materials and Methods

Cell Culture and Total RNA Isolation for 16S rRNA Sequencing

*E. coli* strains BW25113 JW3718Δ and BW25113 JW2171Δ (hereafter JW3718 and JW2171), deficient for 16S rRNA modifying enzymes RsmG and RsuA respectively, were purchased from the Keio Knockout collection (GE Dharmacon). *E. coli* strains K12 MG1655, JW3718, and JW2171 and *S. enterica* strain LT2 were grown in LB media (supplemented with 50 pg/ml kanamycin for JW3718 and JW2171) at 37° C. to an $A_{600}$=0.8-1.0. Cells were harvested by centrifugation and total RNA was extracted with Trizol (Thermo Fisher) following the manufacturer's recommended protocol. All total RNA samples were treated with DNase I (NEB) (2 U/10 ug RNA) in the manufacturer's recommended buffer at 37° C. for 15 minutes. Following the DNase I reaction, RNA was extracted by acid phenol/chloroform extraction (pH 4.4, Fisher Scientific) and two rounds of chloroform extraction. RNA was precipitated with 3 M sodium acetate pH 5.2 and ethanol. RNA was resuspended in nuclease-free water and stored at −80° C. For experiments where human RNA was used as a background, RNA was extracted from $10^7$ HEK 293T cells following the same steps.**

16S rRNA Purification

*E. coli* strain MRE600 16S rRNAs were isolated from purified 30S subunits. *Vibrio cholerae* strain A1552 and *M. maripaludis* strain S2 16S rRNAs were isolated by gel purification as described below. 50-100 pg total RNA (DNase I treated) was heated to 95° C. for 3 minutes in 7M urea/1×TE loading buffer and run on a 4% acrylamide/7M urea/TBE gel for 2.5 hours at 28 W. Gel bands corresponding to 16S rRNA were cut from the gel. 16S rRNA was electroeluted into Maxi-size D-tube dialyzers (3.5 kDa MWCO) in 1×TBE for 2 hours at 100V. RNA was precipitated with sodium acetate and ethanol overnight at −20° C. RNA was pelleted washed once with 80% ethanol. Recovered RNA was resuspended in nuclease free water and quantitated using a Nanodrop spectrophotometer.

Oligonucleotide and 16S rRNA Adapters

The 16S rRNA adapter was designed as follows: the bottom strand (FIG. 1) was designed with a 20-nt 3' overhang complementary to *E. coli* 16S rRNA 3' end, which includes the Shine-Dalgarno sequence. This oligonucleotide used the sequence 5'-CCTAAGAGCAAGAAGAAGCCTAAGGAGGTGATCCAACCGC-3'. The top strand is complementary to the 5' terminus of the bottom strand, and is ligated directly to the 3' end of 16S rRNA. The top strand used the sequence 5'-GGCTTCTTCTTGCTCTTAGGTAGTAGGTTC-3' and was 5' phosphorylated. The 3' terminal 20 nt of this strand were slightly changed to give the adapter complete complementarity to 16S rRNA 3' ends for *V. cholerae* and *M. maripaludis*. Respectively, this resulted in sequences 5'-CCTAAGAGCAAGAAGAAGCCTAAGGAGGTGATCCAGCGCC-3' and 5'-CCTAAGAGCAAGAAGAAGCCAGGAGGTGATCCAGCCGCAG-3'. To make a 16S rRNA adapter, the top and the bottom strands were hybridized at 10 pM each in a buffer containing 10 mM Tris-HCl (pH 8.0), 1 mM EDTA, and 50 mM NaCl. The mixtures were heated to 75° C. for 1 minute before being slowly cooled to room temperature in a thermocycler. It was confirmed that the adapter hybridizes and ligates to *E. coli* str. MRE600 16S rRNA 3' end by a gel electrophoresis-based assay with a 6-FAM-labeled version of the top strand (FIG. 1). For experiments where 16S rRNA was enriched from a total RNA background, a desthiobiotin was added to the 5' terminus of the bottom strand. All adapter oligonucleotides were synthesized by IDT.

Purified 16S rRNA Sequencing Library Preparation

Sequencing libraries of purified 16S rRNA for *E. coli* str. MRE600, *V. cholerae* str. A1552, and *M. maripaludis* str. S2 were prepared as follows: 2 pmol 16S rRNA adapter and 1.5 μg purified 16S rRNA (approximately 3 pmol) were added to a 15 μL reaction in 1× Quick Ligase buffer with 3000 U T4 DNA ligase (New England Biolab). The reaction was incubated at room temperature for 10 minutes. These reactions were cleaned up using 1.8× volume of RNAclean XP beads (Beckman Coulter), washed once with 80% ethanol and resuspended in 20 μl nuclease-free water. The RNA sequencing adapter (Oxford Nanopore Technologies) was ligated to the RNA library following manufacturer recommended protocol.

Preparation of RNA Sequencing Libraries Enriched for 16S rRNA

Enrichment-based 16S sequencing libraries were prepared for *E. coli* strains K-12 MG1655, BL21 DE3 μLys, BL21 DE3 μLys pLM1-RmtB, BL21 DE3 μLys pLM1-RmtBΔ, BW25113 JW3718A, BW25113 JW2171Δ and *S. enterica* strain LT2. 16S rRNA-enriched sequencing libraries were essentially prepared as described for purified 16S rRNA with the following exceptions: 15 pmol of 5' desthiobiotinylated 16S rRNA adapter was added to 4.5-5 μg total RNA in 10 μL buffer containing 10 mM Tris-HCl pH 8, 1 mM EDTA and 50 mM NaCl. The mixture was heated to 50° C. for 1 minute and slowly cooled to room temperature in a thermocycler (~10 minutes). The mixture was then incubated at room temperature for 20 minutes with 100 μL MyOne 01 magnetic streptavidin beads (Thermo Fisher) in 10 mM Tris-HCl (pH 8), 1 mM EDTA, 500 mM NaCl, and 0.025% NP-40 (Buffer A). The beads were washed once with an equal volume of Buffer A and once with an equal volume of buffer containing 10 mM Tris-HCl (pH 8), 1 mM EDTA, 150 mM NaCl (Buffer B). To elute 16S rRNA-enriched RNA, 20 μl Buffer B amended with 5 mM biotin was incubated with the beads at 37° C. for 30 minutes. The hybridized 16S rRNA adapter was then ligated by bringing the mixture to 40 μL 1× Quick Ligase buffer (New England Biolabs) and adding 3000 U of T4 DNA ligase (New England Biolabs). The rest of the library preparation was performed the same as described for purified 16S rRNA sequencing libraries.

The RmtB gene sequence was purchased as a synthetic gene from IDT with the sequence from GenBank accession EU213261.1. pET-32a+ (EMD Millipore) and RmtB gene sequence were digested with XhoI and NdeI. Digested plasmid and geneblock were ligated with T4 DNA ligase (NEB) to create plasmid pLM1-RmtB. To create RmtB null plasmid, pLM1-RmtBΔ, digested pET-32a+ was end repaired and ligated. Plasmids were transformed into *E. coli* DH5a cells (NEB) and confirmed by Sanger sequencing. Confirmed clones for pLM1-RmtB and pLM1-RmtBΔ were transformed into *E. coli* BL21 DE3 pLysS cells to create expression strains. To methylate G1405 in 16S rRNA, *E. coli* BL21 DE3 μLys pLM1-RmtB cells were cultured in 150 ml LB at 37° C. with Ampicillin (100 ug/ml) until $OD_{600}$~0.4. Cultures were diluted into 1 L in pre-warmed LB media with Ampicillin (100 ug/ml), and plasmid expression was induced with 1 mM IPTG. Cultures were grown at 37° C. to an $OD_{600}$~0.4. Cells were then pelleted and resuspended in 30 ml of 25 mM Tris-HCl (pH 7.5), 100 mM $NH_4Cl$, 15 mM $MgCl_2$, 5 mM β-mercaptoethanol. Cells were harvested for RNA purification or flash frozen in liquid nitrogen and stored at −80° C.

Chemical Probing for m7G

Chemical probing for 7-methylguanosine in *E. coli* 16S rRNA was carried out essentially as described previously (Recht et al. 1996). Approximately 10 pmol 16S rRNA or RNA extracted from 70S ribosomes was resuspended in 20 μl 0.5 M Tris-HCl (pH 8.2). Selective reduction of m7G was performed by adding 5 μl freshly made 0.5 M sodium borohydride solution. The reaction was incubated on ice in the dark for 30 minutes. The reaction was ended by the addition of 10 μl 3 M sodium acetate (pH 5.2) and precipitated with ethanol. Pellets were washed once with 80% ethanol. RNA was pelleted by centrifugation and resuspended in 20 μl 1 M aniline/glacial acetic acid solution (1:1.5) (pH 4.5). RNA cleavage proceeded by incubating the reaction at 60° C. for 10 minutes in the dark. The reaction was ended by the addition of 20 μl 0.5 M Tris-HCl (pH 8.2), and the RNA was isolated by extracting with phenol/chloroform/isoamyl alcohol. RNA was precipitated from the aqueous phase, pelleted and washed with 80% ethanol. RNA pellets were resuspended in 2.5 μl nuclease free water.

Primer extension to determine the site of m7G-specific cleavage was carried out as described (Merryman and Noller 1998). To detect G527 methylation, the primer 5'-CGTGCGCTTTACGCCCA-3' was used.

MinION Sequencing of 16S rRNA

MinION sequencing of 16S rRNA libraries was performed using MinKNOW version 1.1.30. The flow cells used were FLO-MIN106 SpotON version. ONT's Metrichor base-calling software (1D RNA Basecalling for FLO-MIN106 v1.134 workflow) takes this raw signal and produces base-called FASTQ sequence in the 5' to 3' order after reads are reversed. During the course of these experiments, ONT made a new local base-caller available, named Albacore. We performed base-calling for the sequencing runs using Albacore v1.0.1, and performed all alignment-based analyses with the newer sequence data.

Data Analysis FastQ sequences were extracted using poretools v0.6 28 and then sequence alignment was performed using marginAlign v0.1 12 (using BWA-MEM version 0.7.12-41044; parameter "-x ont2d" 29). The statistics were calculated using marginStats v0.1 12. Assembly hubs were then created to visualize these alignment on the UCSC genome browser using createAssemblyHub utility in marginAlign suite 12. marginAlign EM was used to estimate the error model from the sequence data. Using these high-quality alignments, substitution rates for the RNA nucleotides in the data were estimated. Using these high-quality alignments, variant calling using marginCaller v0.1 12 was then performed to predict variants and associate systematic sequence mis-calls with putative base modifications. To test for systematic k-mer biases in the RNA data, 5-mers in reads and the known 16S rRNA reference were compared.

Signal Visualization

Nanopore signal for representative reads from different *E. coli* strains was visualized using nanoraw.

Microbial Classification

Binning reads by length (200-600, 600-1000, >1000 bases), 10,000 reads per bin for each microbe were randomly sampled. These reads were then mixed in silico and aligned using marginAlign. A read was called as correctly classified if it aligned to one of the 16S rRNA reference sequences for that microbe. 10 classification iterations were performed for each of the bins.

Notwithstanding the appended claims, the disclosure is also defined by the following clauses:

1. A method for producing a nucleic acid complex, comprising:
   - combining a sample comprising ribosomal RNA (rRNA) and a probe complement oligonucleotide with an oligonucleotide probe comprising:
     - a 3' region complementary to a 3' region of a rRNA; and
     - a 5' region complementary to the probe complement oligonucleotide,
   - under conditions in which the 3' region of the oligonucleotide probe hybridizes to the 3' region of the rRNA and the 5' region of the oligonucleotide probe hybridizes to the probe complement oligonucleotide,
   - to produce a nucleic acid complex.

2. The method according to Clause 1, wherein the rRNA is a eukaryotic rRNA.

3. The method according to Clause 2, wherein the rRNA is an 18S rRNA.

4. The method according to Clause 3, wherein the 3' region of the oligonucleotide probe terminates with the nucleotide sequence: 5'-TAATGATCCTTCC-3'.

5. The method according to Clause 1, wherein the rRNA is a prokaryotic rRNA.

6. The method according to Clause 5, wherein the rRNA is a bacterial rRNA.

7. The method according to Clause 5, wherein the rRNA is an archaeal rRNA.

8. The method according to any one of Clauses 5 to 7, wherein the rRNA is a 23S rRNA.

9. The method according to Clause 8, wherein the 3' region of the oligonucleotide probe terminates with the nucleotide sequence: 5'-AAGGTTAAGCCTC-3'.

10. The method according to any one of Clauses 5 to 7, wherein the rRNA is a 16S rRNA.

11. The method according to Clause 10, wherein the 3' region of the oligonucleotide probe is complementary and hybridizes to a region comprising the anti-Shine-Dalgarno sequence or sub-sequence thereof of the 16S rRNA.

12. The method according to Clause 10 or Clause 11, wherein the 3' region of the oligonucleotide probe is complementary and hybridizes to a region 5' of the anti-Shine-Dalgarno sequence of the 16S rRNA.

13. The method according to Clause 10 or Clause 11, wherein the 3' region terminates with the nucleotide sequence: 5'-$X^1X^2X^3X^4$GAGGT$X^5X^6$TC-3',
   - wherein:
   - $X^1$=A, C, G, T or Z, wherein Z is the absence of a base at that position;
   - $X^2$=A, C, G, T or Z, wherein Z is the absence of a base at that position;
   - $X^3$=A, T or G;
   - $X^4$=G or T;
   - $X^5$=G or A; and
   - $X^6$=A or T.

14. The method according to Clause 13, wherein the 3' region terminates with the nucleotide sequence: 5'-AAAGGAGGTGATC-3'

15. The method according to any one of Clauses 1 to 14, wherein the 3' region of the oligonucleotide probe is from 5 to 20 nucleotides in length.

16. The method according to any one of Clauses 1 to 15, wherein the oligonucleotide probe comprises one or more non-natural nucleotides.

17. The method according to Clause 16, wherein the oligonucleotide probe comprises one or more non-natural nucleotides in the 3' region of the oligonucleotide probe.

18. The method according to any one of Clauses 1 to 17, further comprising covalently linking the 3' end of the rRNA to the 5' end of the probe complement oligonucleotide.

19. The method according to Clause 18, wherein the linking comprises ligating the 3' end of the rRNA to the 5' end of the probe complement oligonucleotide.

20. The method according to any one of Clauses 1 to 19, further comprising producing a derivative of the nucleic acid complex.

21. The method according to Clause 20, wherein producing a derivative of the nucleic acid complex comprises producing a cDNA from the nucleic acid complex.

22. The method according to Clause 21, wherein producing a cDNA comprises performing a first-strand synthesis reaction from the 3' end of the oligonucleotide probe.

23. The method according to any one of Clauses 20 to 22, wherein producing a derivative of the nucleic acid complex comprises amplifying the nucleic acid complex or a derivative thereof.

24. The method according to any one of Clauses 1 to 23, wherein the oligonucleotide probe, the probe complement oligonucleotide, or both, comprises one or more sequencing adapters or sub-regions thereof.

25. The method according to any one of Clauses 1 to 24, further comprising sequencing the nucleic acid complex or a derivative thereof.

26. The method according to Clause 25, wherein the sequencing is by next-generation sequencing.

27. The method according to Clause 26, wherein the next-generation sequencing is nanopore-based sequencing.

28. The method according to any one of Clauses 1 to 27, wherein the oligonucleotide probe, the probe complement oligonucleotide, or both, comprises a label.

29. The method according to any one of Clauses 1 to 28, wherein the oligonucleotide probe, the probe complement oligonucleotide, or both, comprises a unique identifier.

30. The method according to any one of Clauses 1 to 29, wherein the oligonucleotide probe, the probe complement oligonucleotide, or both, comprises an affinity tag.

31. The method according to any one of Clauses 1 to 30, wherein the 3' region of the oligonucleotide probe and the 5' region of the oligonucleotide probe are contiguous.

32. The method according to any one of Clauses 1 to 30, wherein the 3' region of the oligonucleotide probe and the 5' region of the oligonucleotide probe are separated by one or more nucleotides.

33. The method according to any one of Clauses 1 to 32, wherein the combining comprises:

combining a library of oligonucleotide probes, the oligonucleotide probes of the library comprising:

a 3' region complementary to a 3' region of a rRNA; and a 5' region complementary to a probe complement oligonucleotide, wherein the library comprises a plurality of unique oligonucleotide probes that differ from one another with respect to the nucleotide sequence of the 3' region, the nucleotide sequence of the 5' region, or both, to produce a plurality of unique nucleic acid complexes.

34. The method according to any one of Clauses 1 to 33, wherein the sample comprising rRNA is a medical sample.

35. The method according to any one of Clauses 1 to 33, wherein the sample comprising rRNA is an environmental sample.

36. An oligonucleotide probe, comprising:

a 3' region complementary to a 3' region of a rRNA; and a 5' region complementary to a probe complement oligonucleotide.

37. The oligonucleotide probe of Clause 36, wherein the 3' region of the oligonucleotide probe is from 5 to 20 nucleotides in length.

38. The oligonucleotide probe of Clause 36 or Clause 37, wherein the rRNA is a eukaryotic rRNA.

39. The oligonucleotide probe of Clause 38, wherein the rRNA is an 18S rRNA.

40. The oligonucleotide probe of Clause 39, wherein the 3' region of the oligonucleotide probe terminates with the nucleotide sequence: 5'-TAATGATCCTTCC-3'.

41. The oligonucleotide probe of Clause 36 or Clause 37, wherein the rRNA is a prokaryotic rRNA.

42. The oligonucleotide probe of Clause 41, wherein the rRNA is a bacterial rRNA.

43. The oligonucleotide probe of Clause 41, wherein the rRNA is an archaeal rRNA.

44. The oligonucleotide probe of any one of Clauses 41 to 43, wherein the rRNA is a 23S rRNA.

45. The oligonucleotide probe of Clause 44, wherein the 3' region of the oligonucleotide probe terminates with the nucleotide sequence: 5'-AAGGTTAAGCCTC-3'.

46. The oligonucleotide probe of any one of Clauses 41 to 43, wherein the rRNA is a 16S rRNA.

47. The oligonucleotide probe of Clause 46, wherein the 3' region of the oligonucleotide probe is complementary to a region comprising the anti-Shine-Dalgarno sequence or sub-sequence thereof of the 16S rRNA.

48. The oligonucleotide probe of Clause 46 or Clause 47, wherein the 3' region of the oligonucleotide probe is complementary and hybridizes to a region 5' of the anti-Shine-Dalgarno sequence of the 16S rRNA.

49. The oligonucleotide probe of Clause 46 or Clause 47, wherein the 3' region of the oligonucleotide probe terminates with the nucleotide sequence: 5'-$X^1X^2X^3X^4$GAGGT$X^5X^6$TC-3', wherein:

$X^1$=A, C, G, T or Z, wherein Z is the absence of a base at that position;

$X^2$=A, C, G, T or Z, wherein Z is the absence of a base at that position;

$X^3$=A, T or G;

$X^4$=G or T;

$X^5$=G or A; and $X^6$=A or T.

50. The oligonucleotide probe of Clause 49, wherein the 3' region of the oligonucleotide probe terminates with the nucleotide sequence: 5'-AAAGGAGGTGATC-3'.

51. The oligonucleotide probe of any one of Clauses 36 to 50, wherein the oligonucleotide probe comprises one or more non-natural nucleotides.

52. The oligonucleotide probe of Clause 51, wherein the oligonucleotide probe comprises one or more non-natural nucleotides in the 3' region of the oligonucleotide probe.

53. The oligonucleotide probe of any one of Clauses 36 to 52, wherein the oligonucleotide probe comprises one or more sequencing adapters or sub-regions thereof.

54. The oligonucleotide probe of any one of Clauses 36 to 53, wherein the oligonucleotide probe comprises a label.

55. The oligonucleotide probe of any one of Clauses 36 to 54, wherein the oligonucleotide probe comprises a unique identifier.

56. The oligonucleotide probe of any one of Clauses 36 to 55, wherein the oligonucleotide probe comprises an affinity tag.

57. An oligonucleotide probe library, comprising:

a plurality of oligonucleotide probes according to any one of Clauses 36 to 56, wherein the plurality of oligonucleotide probes comprises a plurality of unique oligonucleotide probes that differ from one another with respect to the nucleotide sequence of the 3' region, the nucleotide sequence of the 5' region, or both.

58. A composition, comprising:

an oligonucleotide probe according to any one of Clauses 36 to 56; or an oligonucleotide probe library of Clause 57.

59. The composition of Clause 58, further comprising a probe complement oligonucleotide.

60. A kit, comprising:

the oligonucleotide probe of any one of Clauses 36 to 56, the oligonucleotide probe library of Clause 57, or the composition of Clause 58 or 59; and instructions for using the oligonucleotide probe, the oligonucleotide probe library, or the composition to produce a nucleic acid complex comprising the oligonucleotide probe, an rRNA, and a probe complement oligonucleotide.

61. The kit of Clause 60, further comprising a probe complement oligonucleotide comprising a region that hybridizes to the 5' region of an oligonucleotide probe.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A method for sequencing ribosomal RNA (rRNA), comprising:

producing a nucleic acid complex by combining a sample comprising rRNA and a probe complement oligonucleotide with an oligonucleotide probe comprising:

a 3' region complementary to a 3' region of a rRNA; and a 5' region complementary to the probe complement oligonucleotide, under conditions in which the 3' region of the oligonucleotide probe hybridizes to the 3' region of the rRNA and the 5' region of the oligonucleotide probe hybridizes to the probe complement oligonucleotide, to produce a nucleic acid complex; and directly sequencing the rRNA of the nucleic acid complex using a nanopore-based sequencing system.

2. The method according to claim 1, wherein the rRNA is a eukaryotic rRNA.

3. The method according to claim 2, wherein the rRNA is an 18S rRNA.

4. The method according to claim 3, wherein the 3' region of the oligonucleotide probe terminates with the nucleotide sequence: 5'-TAATGATCCTTCC-3' (SEQ ID NO:1).

5. The method according to claim 1, wherein the rRNA is a prokaryotic rRNA.

6. The method according to claim 5, wherein the rRNA is a bacterial rRNA.

7. The method according to claim 5, wherein the rRNA is an archaeal rRNA.

8. The method according to claim 5, wherein the rRNA is a 23S rRNA.

9. The method according to claim 5, wherein the rRNA is a 16S rRNA.

10. The method according to claim 9, wherein the 3' region of the oligonucleotide probe is complementary and hybridizes to a region of the 16S rRNA selected from the group consisting of: a region comprising the anti-Shine-Dalgarno sequence or sub-sequence thereof of the 16S rRNA, and a region 5' of the anti-Shine-Dalgarno sequence of the 16S rRNA.

11. The method according to claim 9, wherein the 3' region terminates with the nucleotide sequence: 5'-$X^1X^2X^3X^4$GAGGT$X^5X^6$TC-3', wherein:

$X^1$=A, C, G, T or Z, wherein Z is the absence of a base at that position;

$X^2$=A, C, G, T or Z, wherein Z is the absence of a base at that position;

$X^3$=A, T or G;

$X^4$=G or T;

$X^5$=G or A; and $X^6$=A or T.

12. The method according to claim 11, wherein the 3' region terminates with the nucleotide sequence: 5'-AAAGGAGGTGATC-3' (SEQ ID NO:70).

13. The method according to claim 1, wherein the sample comprising rRNA is selected from the group consisting of: a medical sample, and an environmental sample.

14. The method according to claim 1, wherein the rRNA is a microbial rRNA, and wherein the sample is a human total RNA sample.

15. The method according to claim 14, wherein the rRNA is an *E. coli* 16S rRNA.

16. A method for assessing a ribonucleic acid (RNA) for nucleotide modifications, comprising:

producing a nucleic acid complex by combining a sample comprising RNA and a probe complement oligonucleotide with an oligonucleotide probe comprising:

a 3' region complementary to a 3' region of a RNA; and a 5' region complementary to the probe complement oligonucleotide, under conditions in which the 3' region of the oligonucleotide probe hybridizes to the 3' region of the RNA and the 5' region of the oligonucleotide probe hybridizes to the probe complement oligonucleotide, to produce a nucleic acid complex; and directly assessing the RNA of the nucleic acid complex for nucleotide modifications using a nanopore.

17. The method according to claim 16, wherein the RNA is a rRNA.

18. The method according to claim 16, wherein the nucleotide modifications comprise epigenetic modifications.

19. The method according to claim 18, wherein the epigenetic modifications comprise guanosine N7-methylation (m7G), pseudouridylation, or both.

20. The method according to claim 1, further comprising directly assessing the RNA of the nucleic acid complex for nucleotide modifications.

* * * * *

UNITED STATES PATENT AND TRADEMARK OFFICE
CERTIFICATE OF CORRECTION

| | | |
|---|---|---|
| PATENT NO. | : 11,578,362 B2 | Page 1 of 1 |
| APPLICATION NO. | : 16/607646 | |
| DATED | : February 14, 2023 | |
| INVENTOR(S) | : Andrew M. Smith et al. | |

It is certified that error appears in the above-identified patent and that said Letters Patent is hereby corrected as shown below:

In the Specification

In Column 14, Line 62, below "174" insert -- ATATGAGGTGATC 175 --.

In Column 19, Line 35, below "346" insert -- TCGTGAGGTGATC 347 --.

Signed and Sealed this
Twenty-sixth Day of December, 2023

Katherine Kelly Vidal
*Director of the United States Patent and Trademark Office*